US010384006B2

(12) United States Patent
Perazzo et al.

(10) Patent No.: US 10,384,006 B2
(45) Date of Patent: Aug. 20, 2019

(54) SYRINGE FILLING AND PACKAGING SYSTEM FOR HOSPITAL PHARMACIES

(71) Applicant: National Instrument, LLC, Baltimore, MD (US)

(72) Inventors: Nicholas J. Perazzo, Rosedale, MD (US); Robert A. Rosen, Owings Mills, MD (US); John G. Grosskop, Jr., Ellicott City, MD (US); Mark Bennett, Ellicott City, MD (US); John M. Chopper, Pasadena, MD (US)

( * ) Notice: Subject to any disclaimer, the term of this patent is extended or adjusted under 35 U.S.C. 154(b) by 203 days.

(21) Appl. No.: 15/225,384

(22) Filed: Aug. 1, 2016

(65) Prior Publication Data

US 2017/0028130 A1    Feb. 2, 2017

Related U.S. Application Data

(63) Continuation-in-part of application No. 14/792,047, filed on Jul. 6, 2015, and a continuation-in-part of (Continued)

(51) Int. Cl.
| | |
|---|---|
| *A61M 5/178* | (2006.01) |
| *B65B 3/00* | (2006.01) |
| *B65B 57/02* | (2006.01) |
| *B65B 3/28* | (2006.01) |
| *B65B 3/30* | (2006.01) |
| *B65B 5/04* | (2006.01) |
| *B65B 7/28* | (2006.01) |
| *G06Q 10/08* | (2012.01) |
| *G06Q 50/22* | (2018.01) |

(Continued)

(52) U.S. Cl.
CPC .......... *A61M 5/1782* (2013.01); *B65B 3/003* (2013.01); *B65B 3/28* (2013.01); *B65B 3/30* (2013.01); *B65B 5/045* (2013.01); *B65B 7/28* (2013.01); *B65B 57/02* (2013.01); *B65C 3/02* (2013.01); *B65C 3/10* (2013.01); *B67B 3/2006* (2013.01); *B67B 7/182* (2013.01); *G06Q 10/087* (2013.01); *G06Q 50/22* (2013.01); *G16H 20/17* (2018.01); *A61J 7/0053* (2013.01); *B01L 1/00* (2013.01); *B01L 3/0217* (2013.01)

(58) Field of Classification Search
CPC .......... B67B 7/182; A61J 1/20; A61J 1/2096; B65B 3/003; B65B 59/00; A61M 5/1782
See application file for complete search history.

(56) References Cited

U.S. PATENT DOCUMENTS

| 9,840,343 B2 * | 12/2017 | Tachibana .............. B25J 9/0087 |
| 2008/0114328 A1 * | 5/2008 | Doherty ................ A61J 1/2096 604/414 |

(Continued)

*Primary Examiner* — Timothy P. Kelly
(74) *Attorney, Agent, or Firm* — Royal W. Craig; Gordon Feinblatt LLC

(57) ABSTRACT

A semi-automated system (100) suitable for use in a hospital setting for filling patient-specific liquid medication prescriptions from bulk medicine containers (104) into oral/enteral syringes (S) for administration on a just-in-time basis. The system enables hospital pharmacists to simplify and streamline their task, increasing the number of prescriptions that can be filled in a day, improving patient safety and care by minimizing medication errors and the consequences that ensue.

27 Claims, 42 Drawing Sheets

Related U.S. Application Data application No. PCT/US2015/013217, filed on Jan. 28, 2015, and a continuation-in-part of application No. 13/788,849, filed on Mar. 7, 2013, now Pat. No. 9,466,088.

(60) Provisional application No. 62/294,003, filed on Feb. 11, 2016, provisional application No. 62/020,980, filed on Jul. 3, 2014, provisional application No. 61/607,867, filed on Mar. 7, 2012.

(51) Int. Cl.
| | | |
|---|---|---|
| *B65C 3/02* | (2006.01) | |
| *B65C 3/10* | (2006.01) | |
| *B67B 3/20* | (2006.01) | |
| *B67B 7/18* | (2006.01) | |
| *G16H 20/17* | (2018.01) | |
| *A61J 7/00* | (2006.01) | |
| *B01L 1/00* | (2006.01) | |
| *B01L 3/02* | (2006.01) | |

(56) References Cited

U.S. PATENT DOCUMENTS

| | | | |
|---|---|---|---|
| 2009/0067973 A1* | 3/2009 | Eliuk | B66C 1/42 |
| | | | 414/729 |
| 2012/0048424 A1* | 3/2012 | Giribona | B65B 3/003 |
| | | | 141/311 R |
| 2014/0131534 A1* | 5/2014 | Okuma | B65B 3/006 |
| | | | 248/213.2 |
| 2014/0157731 A1* | 6/2014 | Perazzo | B65B 57/02 |
| | | | 53/473 |
| 2019/0009935 A1* | 1/2019 | Stultz | A61M 5/1782 |

\* cited by examiner

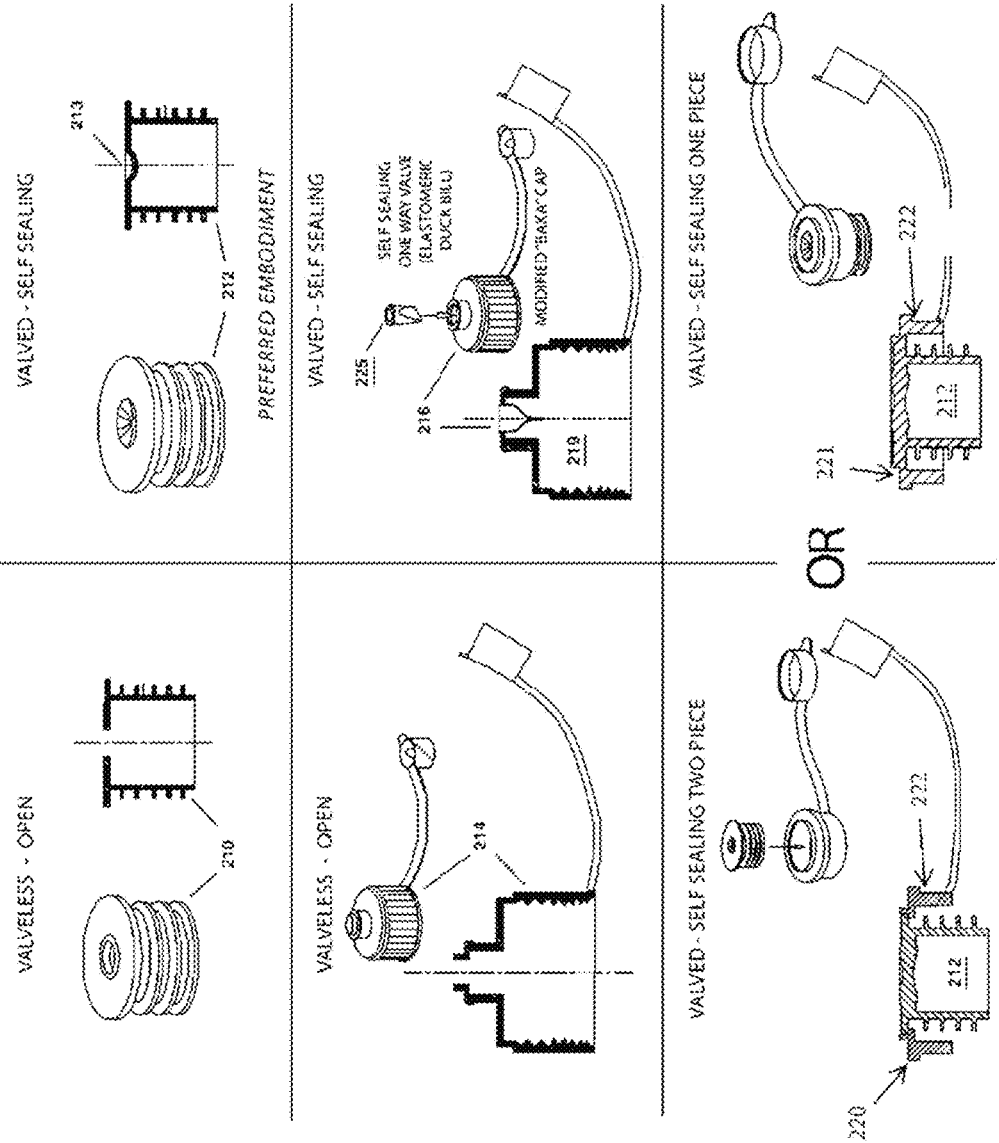

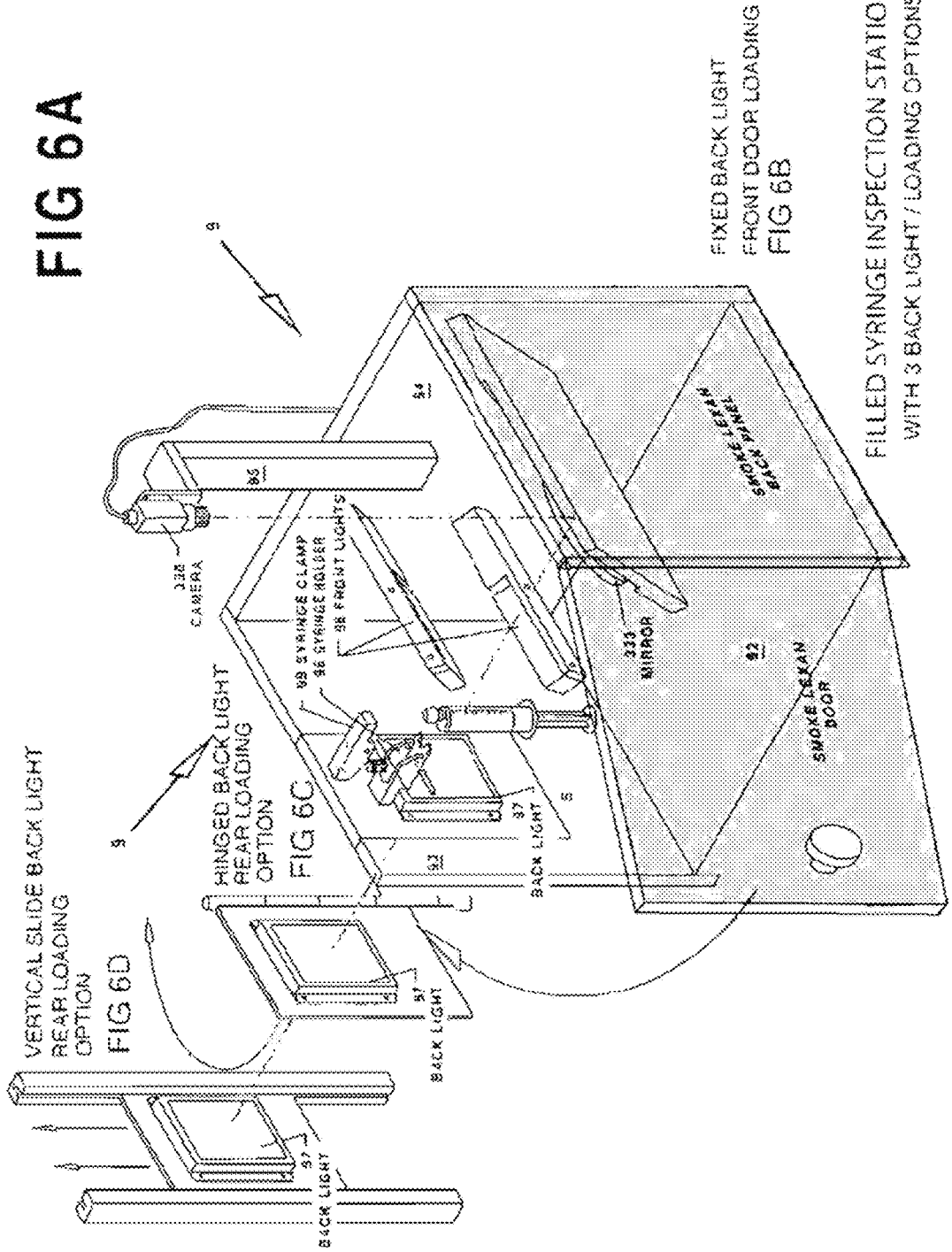

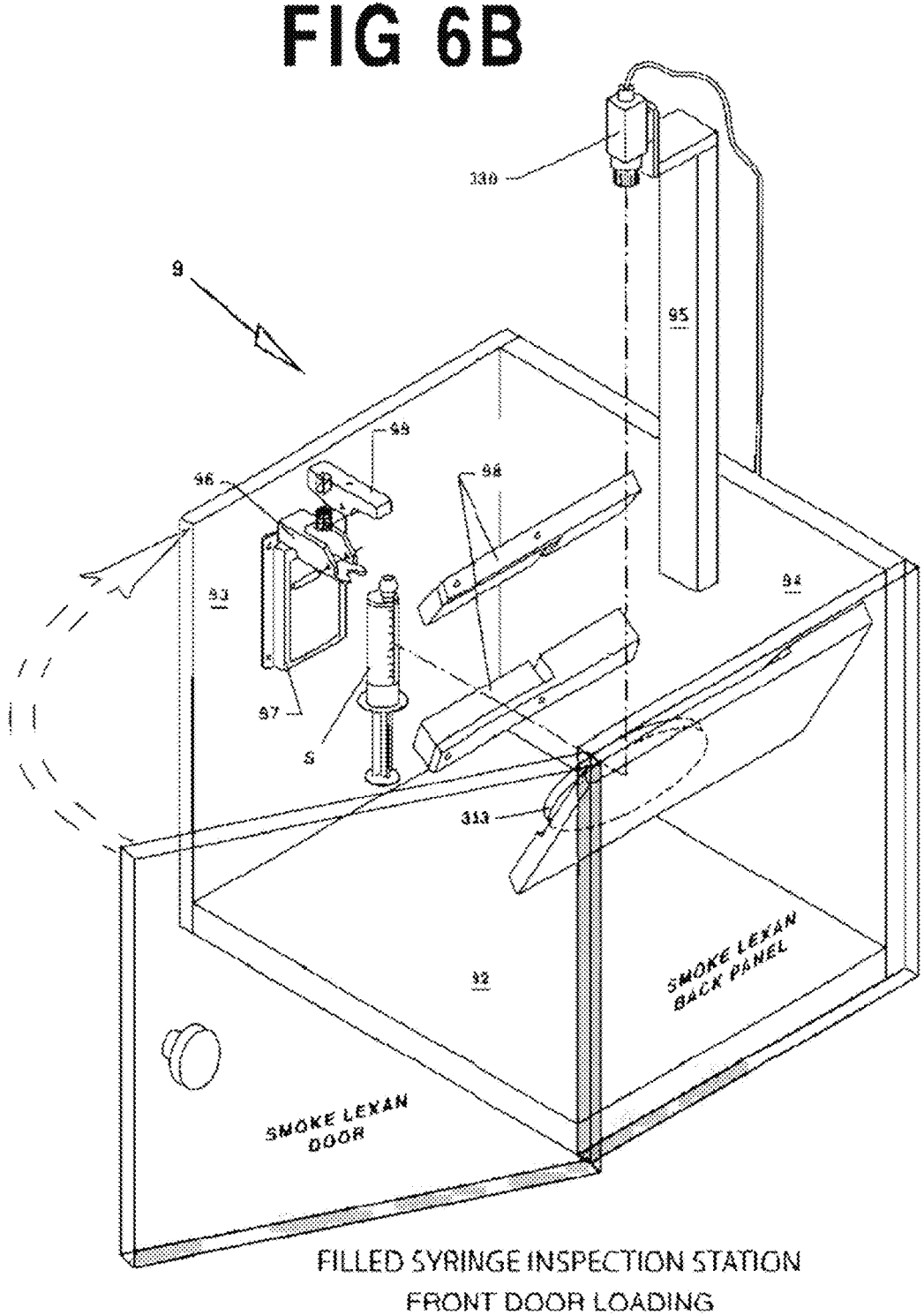

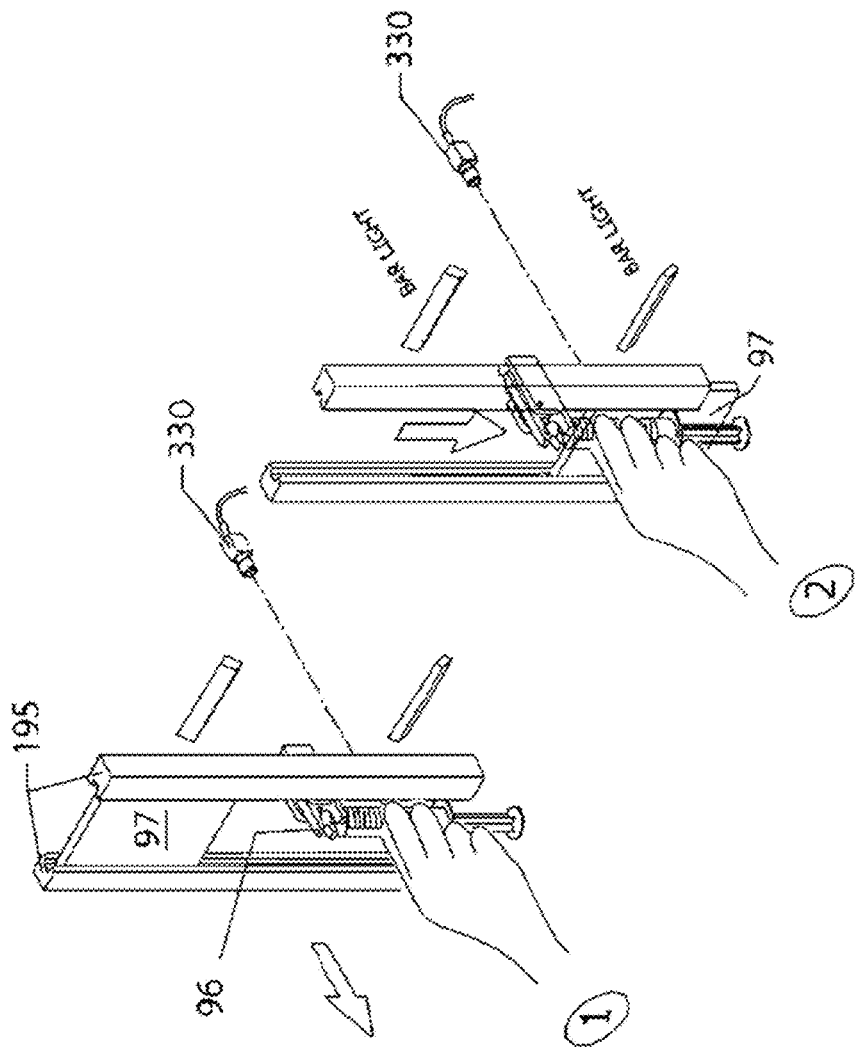

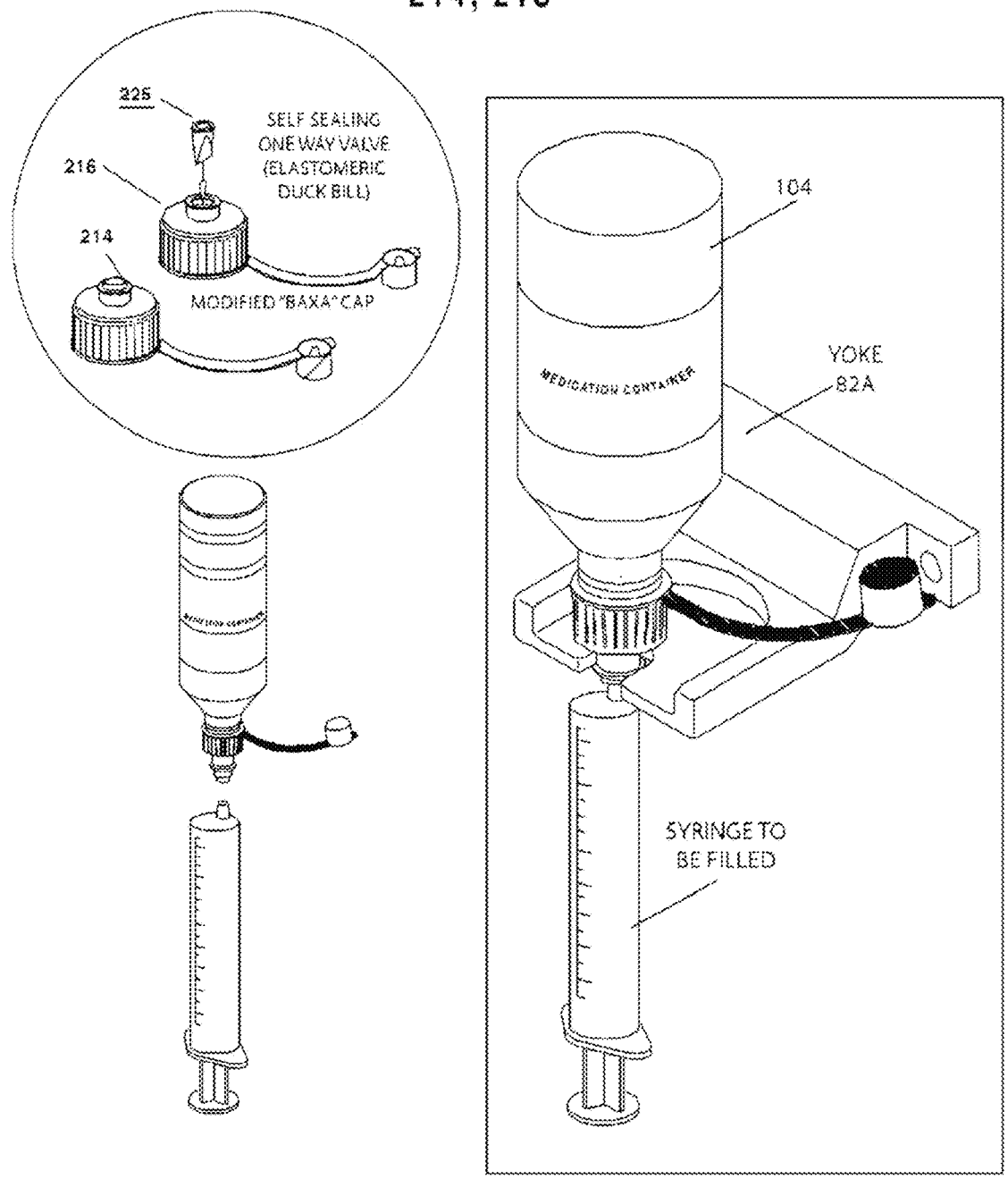

FIG 7C II  FOR: SYRINGE / MEDICATION / INTERFACE 210
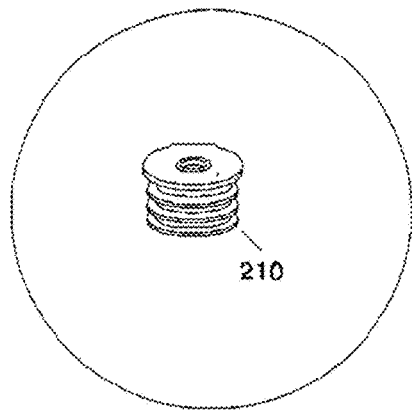
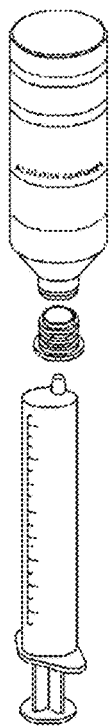
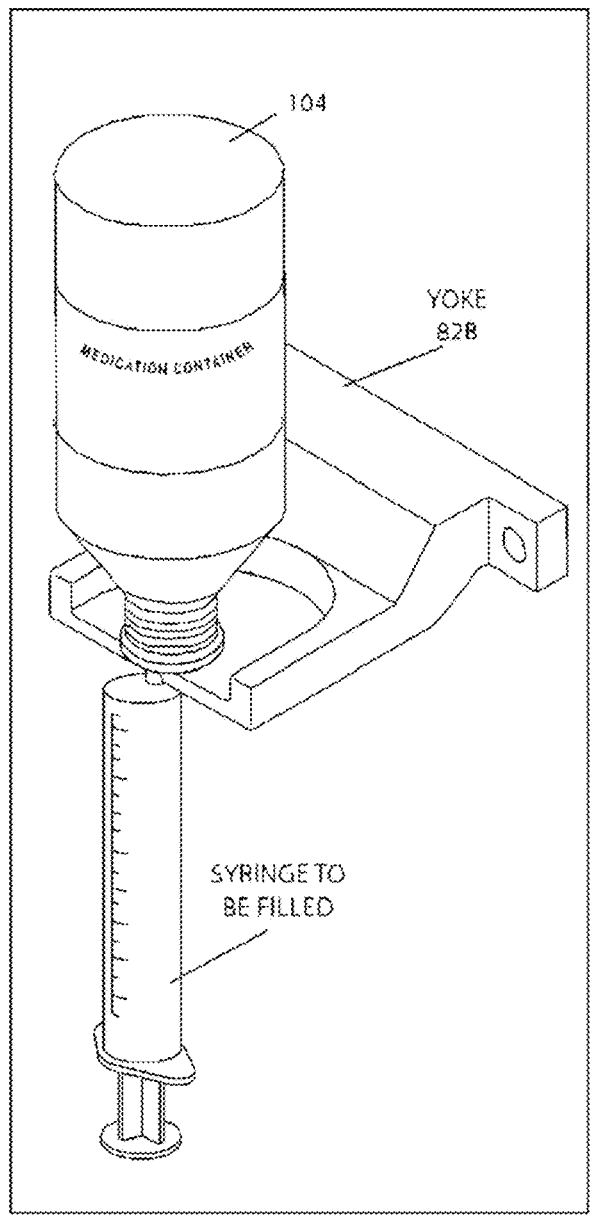

FIG 7C III FOR: SYRINGE / MEDICATION / INTERFACE 212
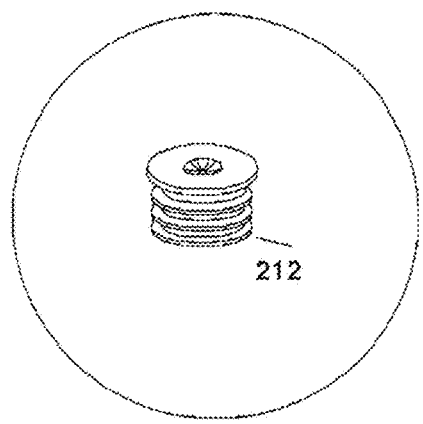
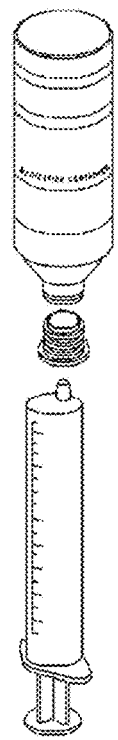
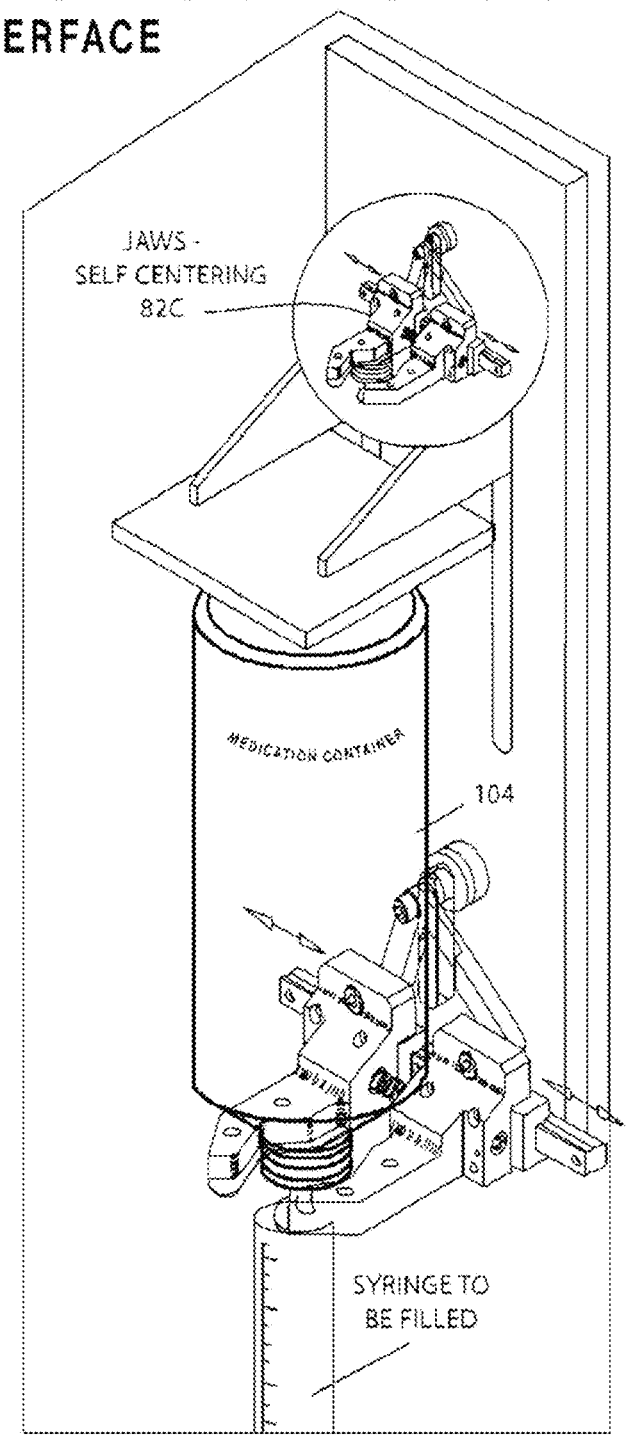

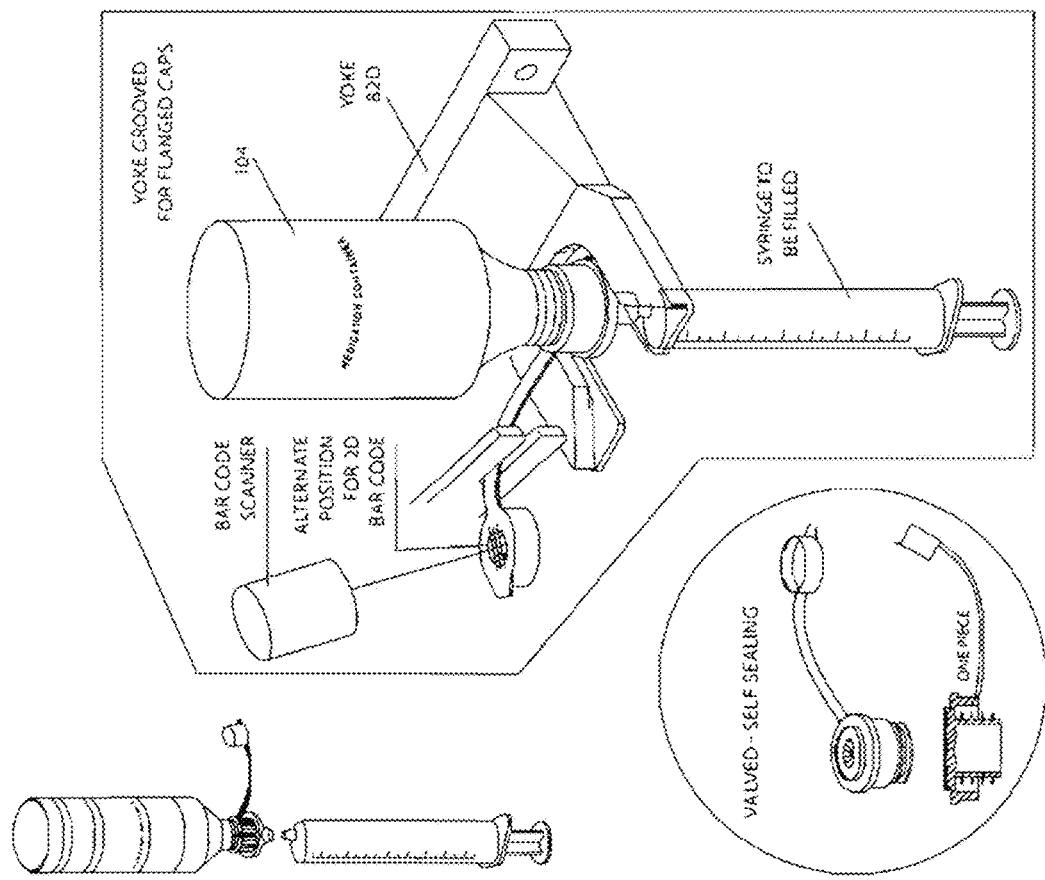

FIG 7D  MEDICATION CONTAINER / SYRINGE GRIPPER DETAIL

ONCE BOTTLE AND SYRINGE ARE IN PLACE AND SENSOR 121 VERIFIES CORRECT BAR CODE, AND START BUTTONS ARE PRESSED: FINGER GRIPPERS CLOSE AROUND SYRINGE AND BOTTLE HOLDER PLATFORM LOWERS TO HOLD MEDICATION BOTTLE TIGHTLY AGAINST YOKE

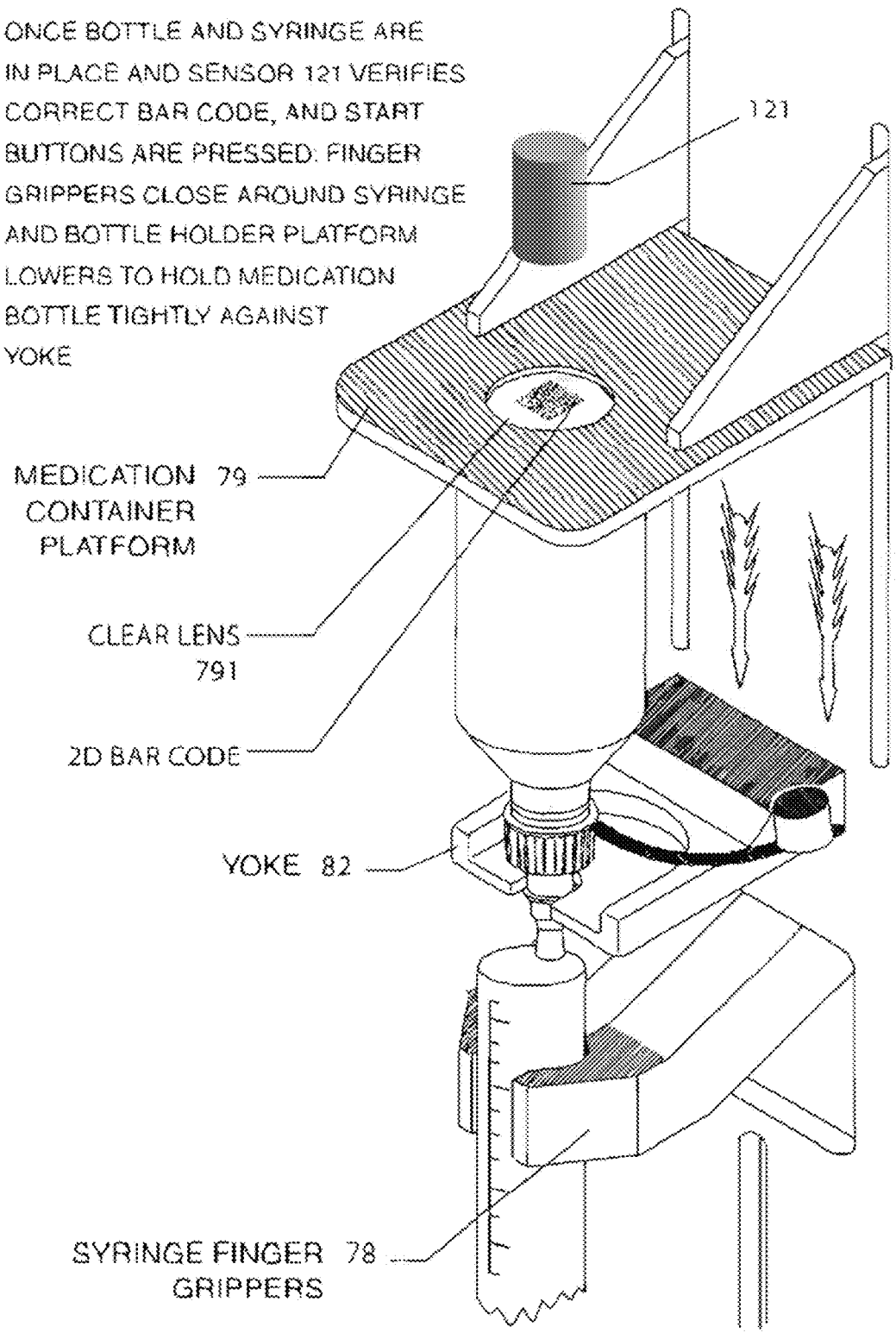

- MEDICATION CONTAINER PLATFORM 79
- CLEAR LENS 791
- 2D BAR CODE
- YOKE 82
- SYRINGE FINGER GRIPPERS 78
- 121

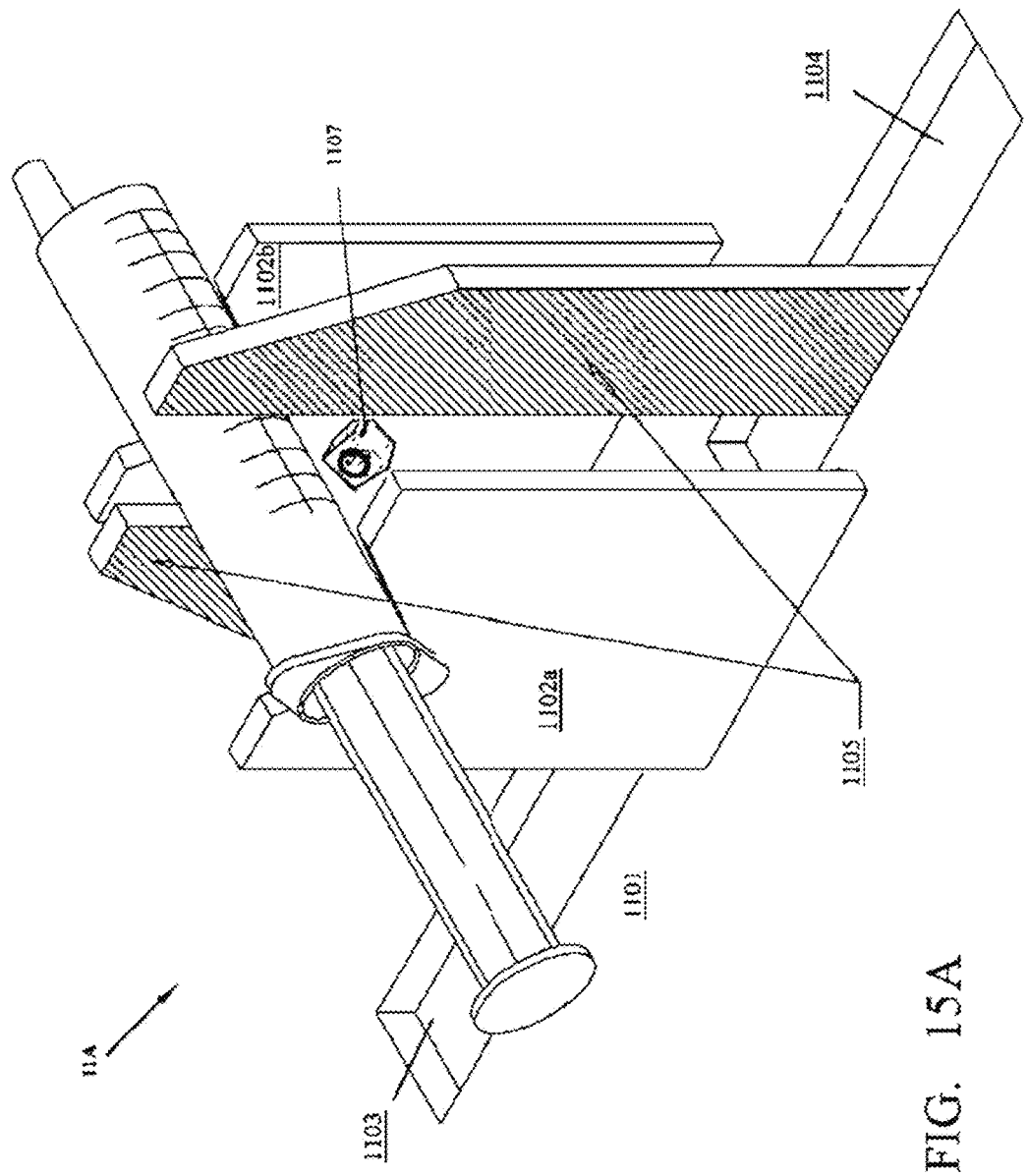

ALTERNATE SIZE / COLOR INSPECTION

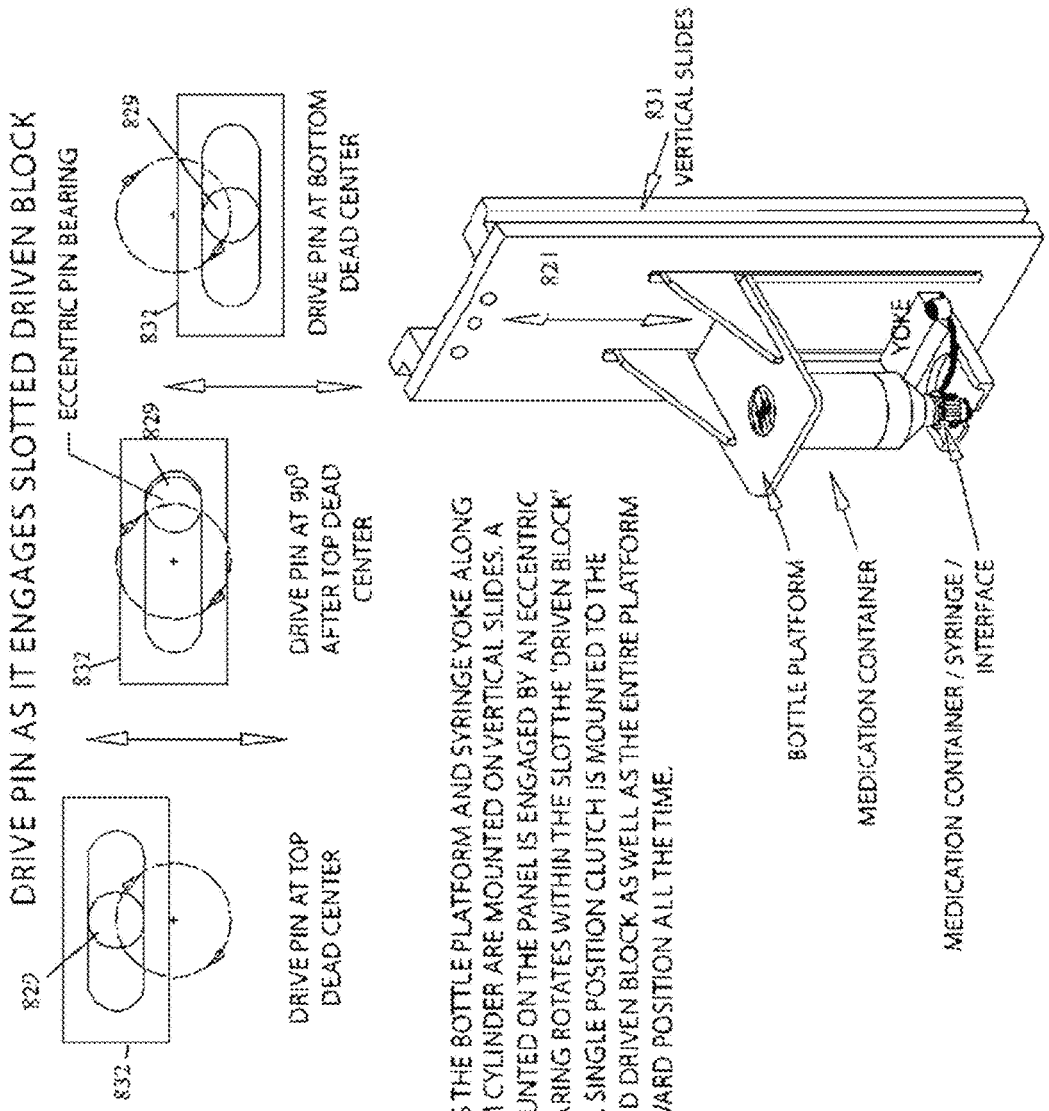

OPTIONAL, STAND ALONE MEDICATION CONTAINER SHAKER STATION

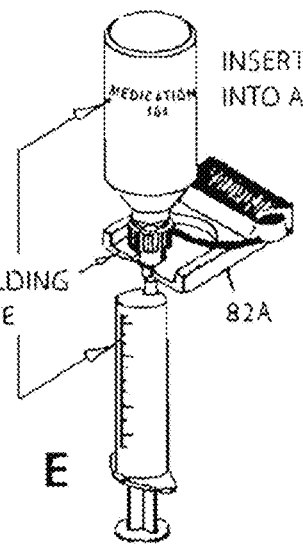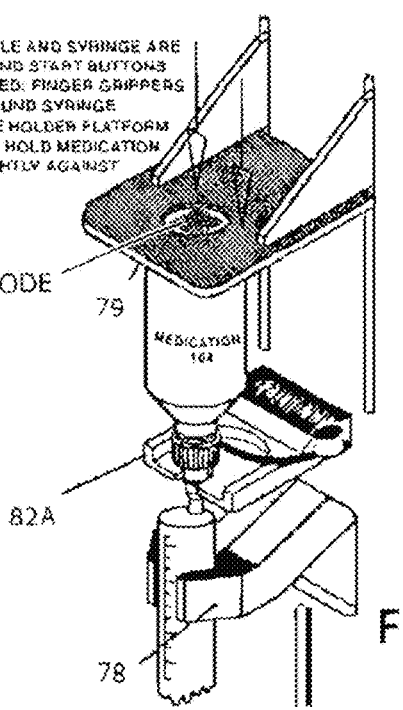
FIG 18

FLOW RESTRICTOR (WITHOUT SELF - SEALING)
REMOVE MEDICINE BOTTLE CAP
A
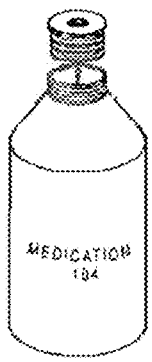
B
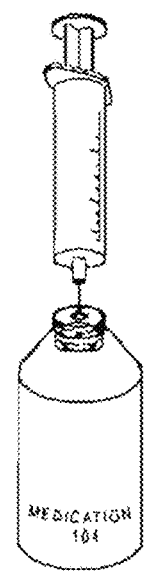
C
MOVE SYRINGE UP INTO HOLE
D
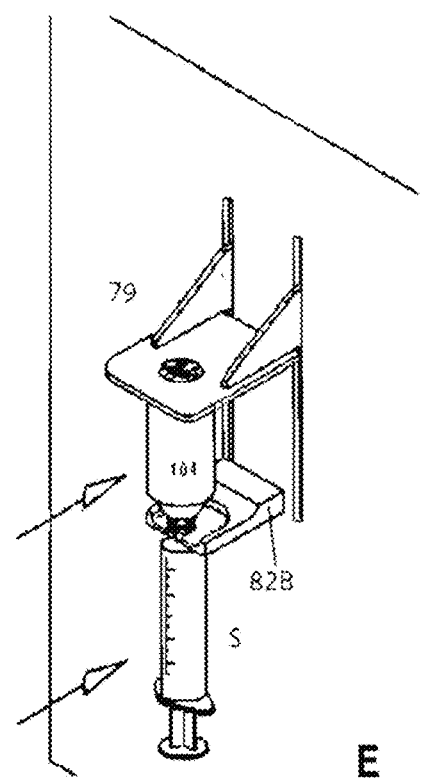
E
FIG 20

FLOW RESTRICTOR (SELF - SEALING)
A
B
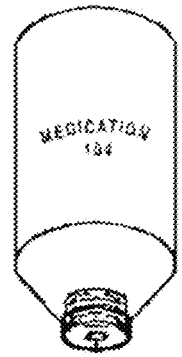
C
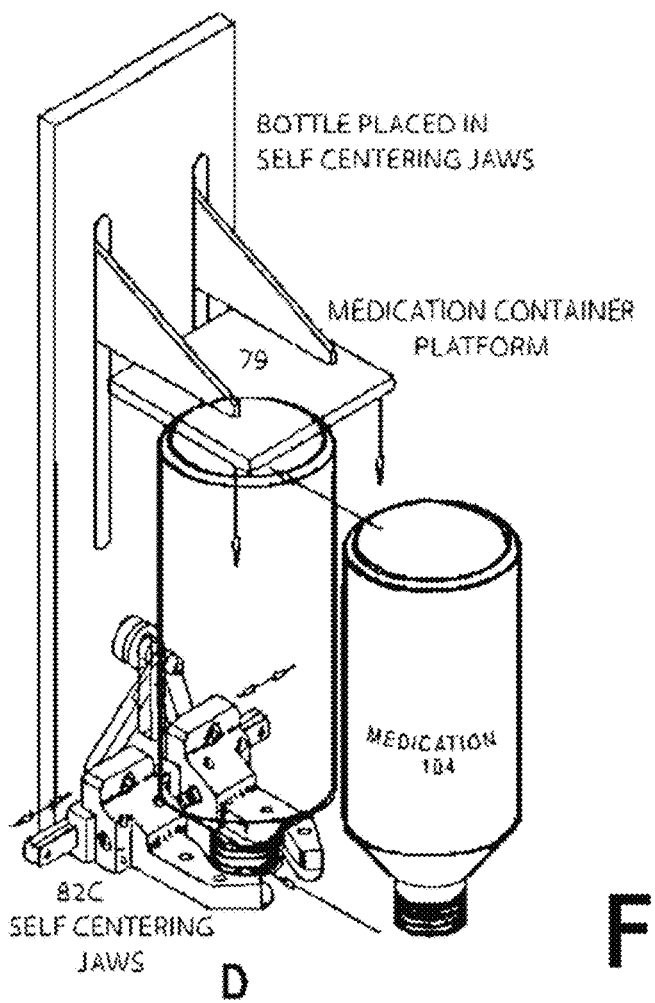
D
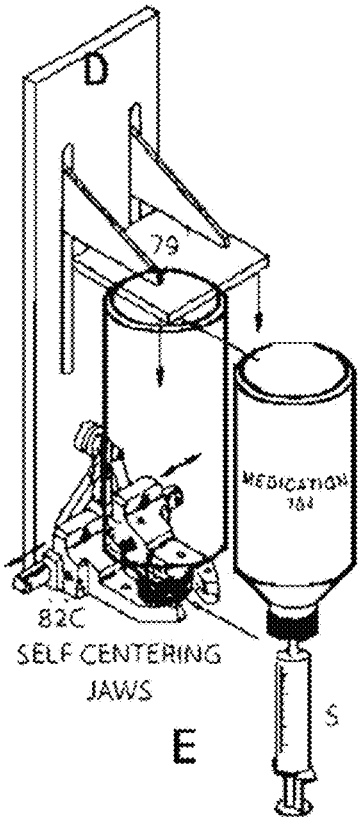
E
FIG 21

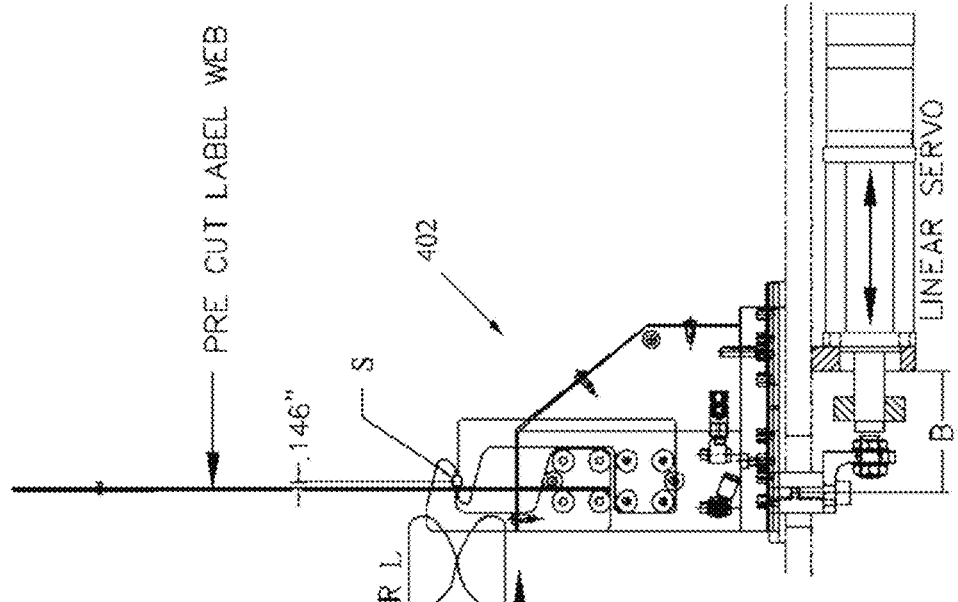
FIG. 32(B)
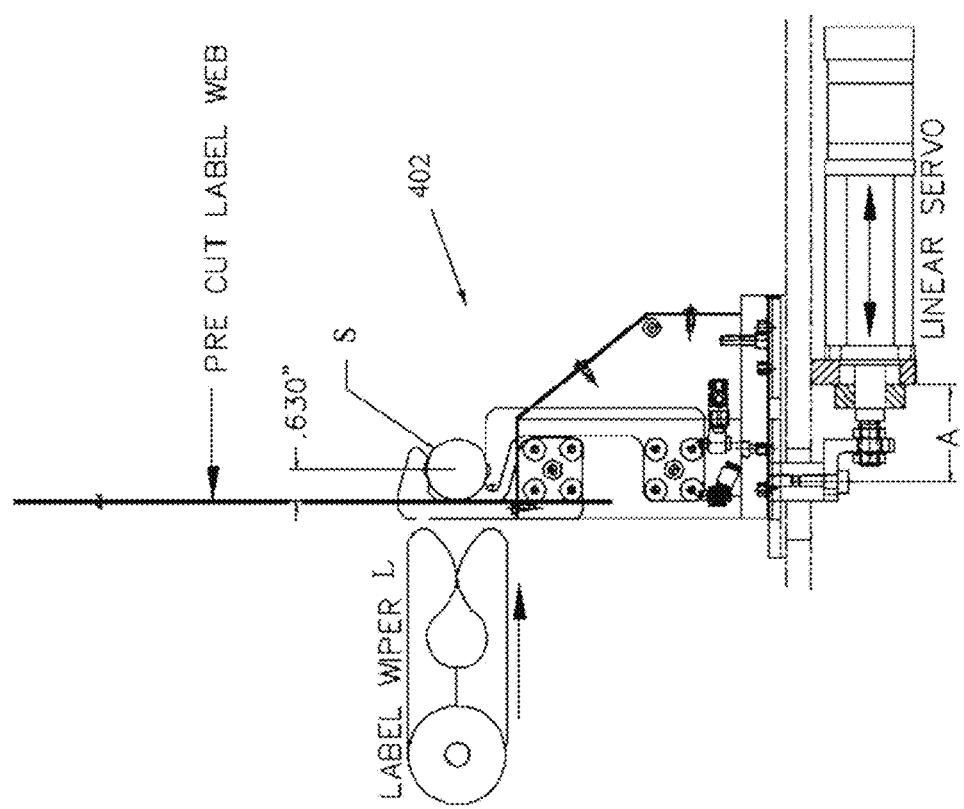
FIG. 32(A)
FIG. 32

SYRINGE FILLING AND PACKAGING SYSTEM FOR HOSPITAL PHARMACIES

CROSS-REFERENCE TO RELATED APPLICATIONS

The present application derives priority from U.S. provisional patent application Ser. No. 62/294,003, filed 11 Feb. 2016, and is a continuation-in-part of U.S. patent application Ser. No. 13/788,849 filed 7 Mar. 2013 (which derives priority from U.S. provisional patent application Ser. No. 61/607,867 filed 7 Mar. 2012), and is a continuation-in-part of PCT application PCT/US15/13217 filed 28 Jan. 2015, and is a continuation-in-part of U.S. patent application Ser. No. 14/792,047 (which derives priority from U.S. provisional patent application Ser. No. 62/020,980 filed Jul. 3, 2014), all of which are incorporated herein by reference.

BACKGROUND OF THE INVENTION

1. Field of the Invention

The present invention relates generally to oral/enteral syringe packaging equipment and more specifically to a partially automated system for preparing patient-specific doses of selected pharmaceutical liquid medication for administration by oral/enteral syringe on a just-in-time basis, for use in a hospital pharmacy.

2. Description of the Background

Enteral syringes are used for tube feeding, irrigation or drug administration into the gastrointestinal (GI) tract. This contrasts with parenteral nutrition or drug administration which occurs from routes outside the GI tract, such as intravenous routes. Oral syringes are used to administer liquid medicine into the mouth, as an alternative to pills which can present a choking hazard or be expectorated, typically for infants/children and uncooperative or geriatric adults. The oral syringe directs liquid medicine to the back of the throat prompting a swallowing response. Parenteral syringes (e.g., injectable syringes) on the other hand, are used to administer medication into the body by injecting its contents through the skin. Injectable syringes utilize a needle on the tip of the syringe. Injectable syringes must be manufactured and packaged in a sterile environment.

Research has shown that the potential for adverse drug events within the pediatric inpatient population is about three times as high as among hospitalized adults. See, Joint Commission, Preventing Pediatric Medication Errors, Issue 39 (2008). According to the Commission Report, the most common types of harmful pediatric medication errors were improper dose/quantity (37.5 percent) and unauthorized/wrong drug (13.7 percent), followed by improper preparation or dosage form. Enteral/oral syringes help to minimize these problems and are considered the gold standard for delivering medicine to children.

Enteral/oral syringes are comprised of a simple piston pump with a plunger that fits tightly in one end of a cylindrical tube (the barrel) and can be pushed or pulled along inside the barrel to create negative or positive relative pressure within the barrel that causes the syringe to take in or expel a liquid or gas through an orifice (terminal discharge) at the opposing end of the barrel. The barrel of an enteral/oral syringe is typically made of plastic and is at least partially transparent along its length with graduated markings to indicate the volume of fluid in the syringe based on the position of the plunger visible within the barrel. Enteral/oral syringes come in a wide range of sizes and with some variation in configuration. For example, some enteral/oral syringes have the terminal discharge located along the central axis while others have the terminal discharge offset from the central axis. This variability makes it difficult to automate the filling process. Enteral/oral syringes are commonly marked in units of milliliters and come in standard sizes ranging from 0.5 to 60 milliliters. An annular flange partially or fully encircling the outside surface of the barrel is typically provided to facilitate compression of the plunger into the barrel. The plunger is also typically plastic as this provides a good seal within the barrel and is inexpensive to produce so as to be disposable, reducing the risk of contamination or transmission of communicable disease.

Pharmacies at in-patient medical facilities and other medical institutions fill a large number of prescriptions on a daily basis including prescriptions for liquid or compounded suspension medicines to be administered by oral/enteral syringe, and must do so accurately for medical safety reasons. For example, the volume of an oral/enteral pediatric prescription's dose is determined by the child's weight. This makes it impractical to stock pre-filled syringes due to the wide range of Fill volumes required. As a result, pediatric enteral/oral liquid doses are prepared in the hospital pharmacy on a patient-specific, just-in-time basis. The process of filling numerous, variously sized single dose prescriptions for delivery by oral/enteral syringe is time consuming, labor intensive and prone to human error. To insure that the medication is packaged error-free, the pharmacy technician must make sure that; (1) the syringe contains the correct medication; (2) the syringe contains the correct amount of medication; (3) the syringe is capped correctly; (4) the medication has not expired; (5) the medication has not been recalled; (6) the medication, when required, is shaken; (7) the medication, when required, has been properly refrigerated; (8) the medication, when required, has been properly protected from exposure to light; (9) the information on the syringe label is correct; (10) the syringe is placed into the correct bag; (11) the information on the bag containing the syringe is correct; (12) the bag is properly sealed; and (13) the syringe is protected from cross contamination from other medications. The process typically requires a pharmacist or pharmacy technician to retrieve the correct medication from a storage cabinet (with or without light protection) or refrigerated storage area. The liquid medications are typically stored in a container sealed with a safety cap or seal. After confirming the contents of the retrieved container and shaking the medication (if necessary), the technician manually opens die cap and attaches the tip of an enteral/oral syringe to the container, withdrawing the plunger to draw the medication into the barrel of the syringe. After filling with a proper amount, the tip of the syringe is covered with a cap for transport to the patient and the syringe is labeled to indicate its content, the intended recipient, and then bagged. Prior to administering the dose, the nurse can determine the amount of the dose by observing where the tip of the plunger or piston is located in the barrel. Oral/enteral syringes are relatively inexpensive and disposable.

Currently, the degree of automation in the hospital pharmacy for the packaging of oral/enteral syringes is very limited. Islands of automation exist, such as automatic labeling of the syringe and bagging of the filled and capped syringe. However, the filling and capping are done manually. Scanners, cameras, bar code readers and track-and-trace technology have not been applied on an integrated, comprehensive basis for the packaging of enteral/oral syringes in the hospital pharmacy. The potential to reduce medication errors using this technology is significant yet largely untapped. Automated systems have been developed by Baxa, Inc., For Health Technologies, Inc., Intelligent Hospital Systems and others for the automated filling of injectable syringes.

For example, U.S. Pat. Nos. 6,991,002; 7,017,622; 7,631,475 and 6,976,349 are all drawn to automated removal of a tip cap from an empty syringe, placing the tip cap at a remote location, and replacing the tip cap on a filled syringe. U.S. Pat. Nos. 7,117,902 and 7,240,699 are drawn to automated transfer of a drug vial from storage to a fill station. U.S. Pat. No. 5,884,457 shows a method and apparatus for filling syringes using a pump connected by hose to a fluid source. U.S. Pat. No. 7,610,115 and Application 20100017031 show an Automated Pharmacy Admixture System (APAS). U.S. Application 20090067973 shows a gripper device for handling syringes of different diameters with tapered or angled gripper fingers. U.S. Pat. No. 7,343,943 shows a medication dose under-fill detection system. U.S. Pat. No. 7,260,447 shows an automated system for fulfilling pharmaceutical prescriptions. U.S. Pat. No. 7,681,606 shows an automated system and process for filling syringes of multiple sizes. U.S. Pat. No. 6,877,530 shows an automated means for withdrawing a syringe plunger. U.S. Pat. No. 5,692,640 shows a system for establishing and maintaining the identity of medication in a vial using preprinted, pressure sensitive, syringe labels.

The foregoing references are for packaging injectable syringes. The packaging process required for injectable syringes is significantly different titan that for enteral/oral syringes. Injectable syringes must be packaged in a sterile environment as the medication is injected into the body. This requirement adds cost and complexity to the machine. Injectable medications, when packaged on a just-in-time basis as with the Baxa, For Health Technologies, and Intelligent Hospital System machines, must typically be prepared by the machine before the medication is filled into the syringe. The medication preparation process involves diluting the medication or reconstituting the medication from a powdered state with water. This process adds expense and slows down the packaging process as well. The Intelligent Hospital Systems syringe packaging system is designed to be used to package cytotoxic medications which are hazardous. To avoid harm to the operator, this machine uses a robot located within an isolating barrier at considerable cost. The Baxa, For Health Technologies, and Intelligent Hospital System machines require the use of expensive disposable product contact parts when a different medication is to be filled. The foregoing machines are not suitable for packaging enteral/oral syringes due to their capital cost, complexity, slow production rates, inability to handle enteral/oral medication containers, and the requirement of expensive disposable contact parts. Consequently, existing automation does not address the needs of medical institutions desiring an affordable pharmacy automation system for patient safety, prescription tracking and improved productivity. The present invention was developed to fill this void.

Oral and/or enteral syringes are manufactured in a variety of sizes with differing tip and plunger configurations. Moreover, oral/enteral medications are commonly provided in bulk form in variously sized bottles or containers having threaded screw caps that must be removed and replaced between uses. Additionally, in-patient medical facilities such as hospitals are moving toward electronic prescription ("e-prescription") systems which use computer systems to create, modify, review, and/or transmit medication prescriptions from the healthcare provider to the pharmacy. Handwritten and facsimile prescriptions are often very difficult to read, and decimal places are sometimes misinterpreted. While e-prescribing improves patient safety and saves money by eliminating the inefficiencies and inaccuracies of the manual, handwritten prescription process, any syringe fill automation system suitable for use in a hospital setting must interface with an existing e-prescription system (which records and transmits prescriptions to the pharmacy), and must be capable of filling prescription orders in a just-m-time environment.

Given the diversity of enteral/oral syringes and medicines available, any semi-automated (or fully-automated) system will need sufficient dexterity to manipulate all the myriad prescription bottles containing the pharmaceuticals to be dispensed as well as variously sized enteral/oral syringes, bringing them together m a controlled environment to quickly and accurately fill and label each syringe and to verify its work as it proceeds in order to avoid errors in the process. Such a system would need to be reliably constructed so as to minimize downtime, quickly take and fill orders, be easy to clean and capable of maintaining an environment free from cross contamination. Such a system would also need to be able to interact with a human operator at multiple points in the operation.

The present inventors herein provide a semi-automated system suitable for use in a hospital setting for filling patient-specific doses of liquid medications to be administered by oral/enteral syringes on a just-in-time basis, as well as an automated alternative. The system enables hospital pharmacists to simplify and streamline their task, increasing the number of prescriptions that can be filled in a day, improving patient safety and care by minimizing medication errors and the consequences that ensue.

BRIEF DESCRIPTION OF THE DRAWINGS

The objects, features, and advantages of the present invention will become apparent from the following detailed description of the preferred embodiments and certain modifications thereof when taken together with the accompanying drawings in which like numbers represent like items throughout and in which:

FIG. 5 is a composite view of the four embodiments of container/syringe interfaces according to the invention. The container/syringe interfaces (closures) include caps, closures and neck inserts meant to facilitate the connection of an enteral/oral syringe to a medication container for the purpose of drawing fluid out of the container.

FIGS. 6A and 6B are perspective views of an exemplary vision inspection station 9.

FIG. 6D shows another alternative articulating design for the backlight panel 97.

FIG. 7C I is an enlarged perspective view of fixed yoke 82A illustrating how it is used.

FIG. 7C II is an enlarged perspective view of fixed yoke 82B illustrating how it is used.

FIG. 7C III is an enlarged perspective view of self-centering jaws 82C illustrating how they is used.

FIG. 7C IV is an enlarged perspective view of fixed yoke 82D illustrating how it is used.

FIG. 7D is a further enlarged perspective view of the loading carriage 70 of FIG. 7A.

FIG. ISA is a perspective view of an embodiment of the syringe size/color station 11A which verifies that the correct syringe has been selected.

Figure 15B:
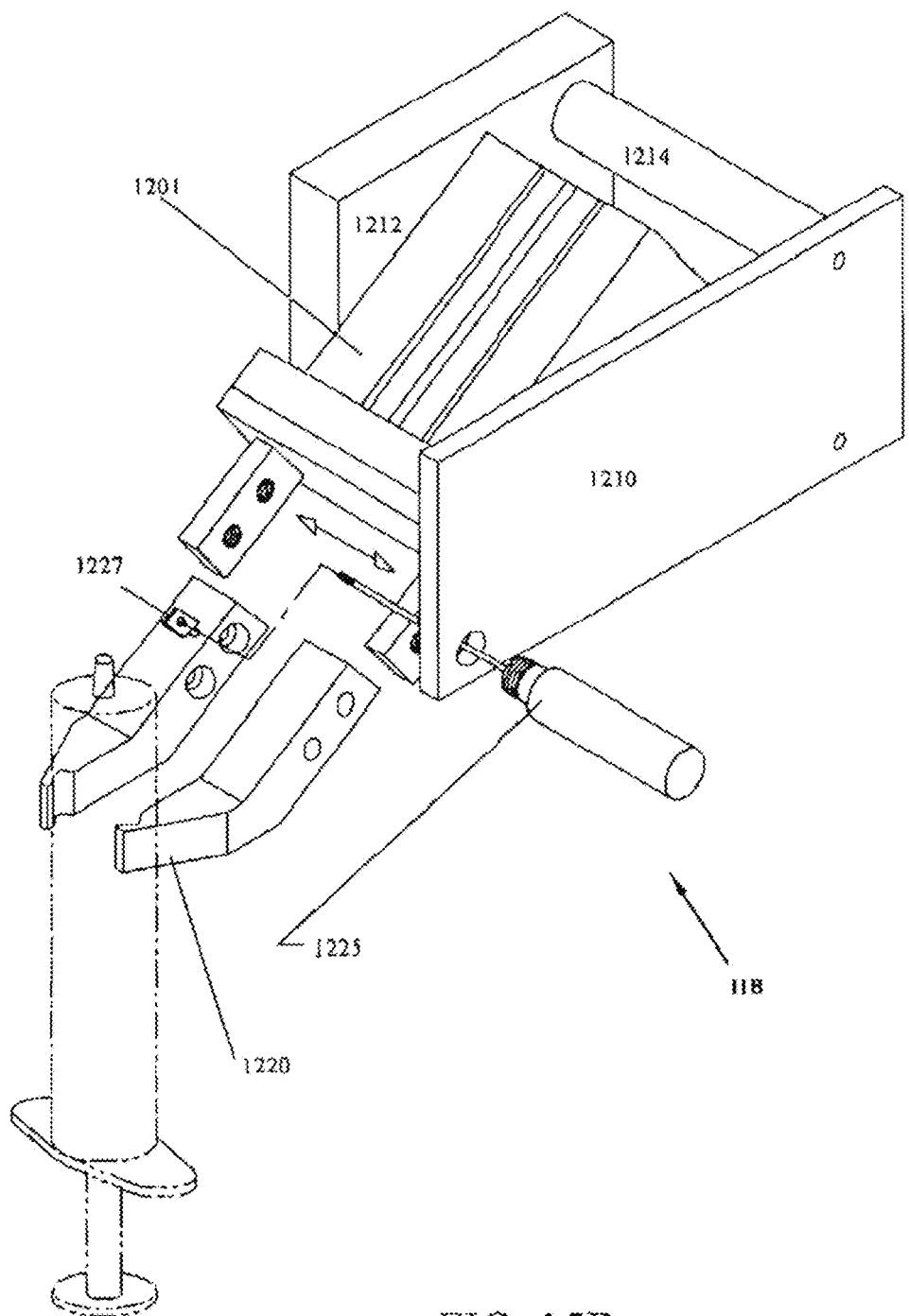

FIG. 15B is a perspective view of an alternate embodiment of the syringe size/color station 11B which verifies that the correct syringe has been selected.

Figure 16A:
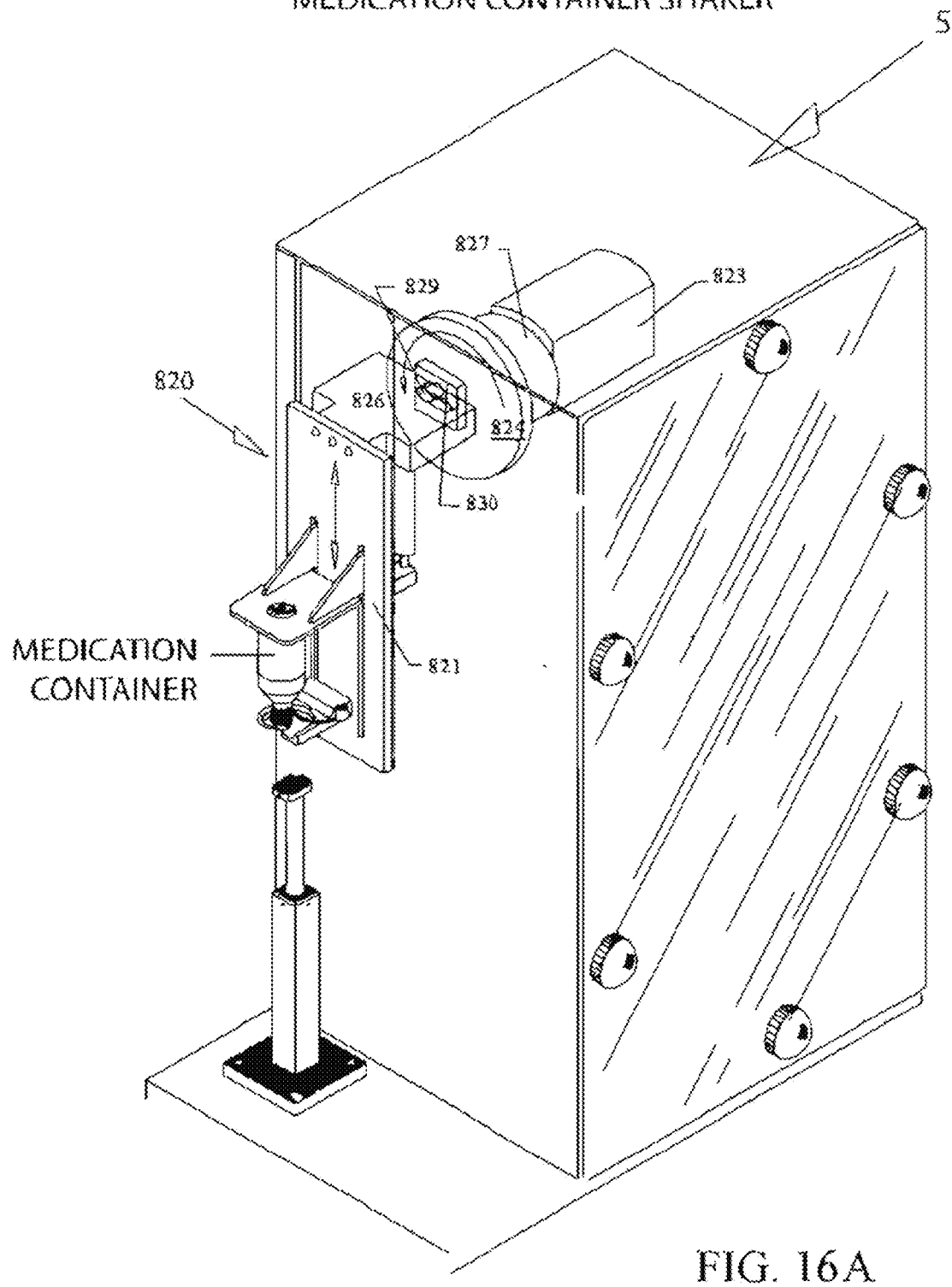

FIG. 16A illustrates an embodiment of a shaking mechanism 820 integral to the filling station 5.

FIG. 16B is a composite operational diagram illustrating the operation of the integral shaking mechanism 820 of FIG. 16A.

Figure 17:
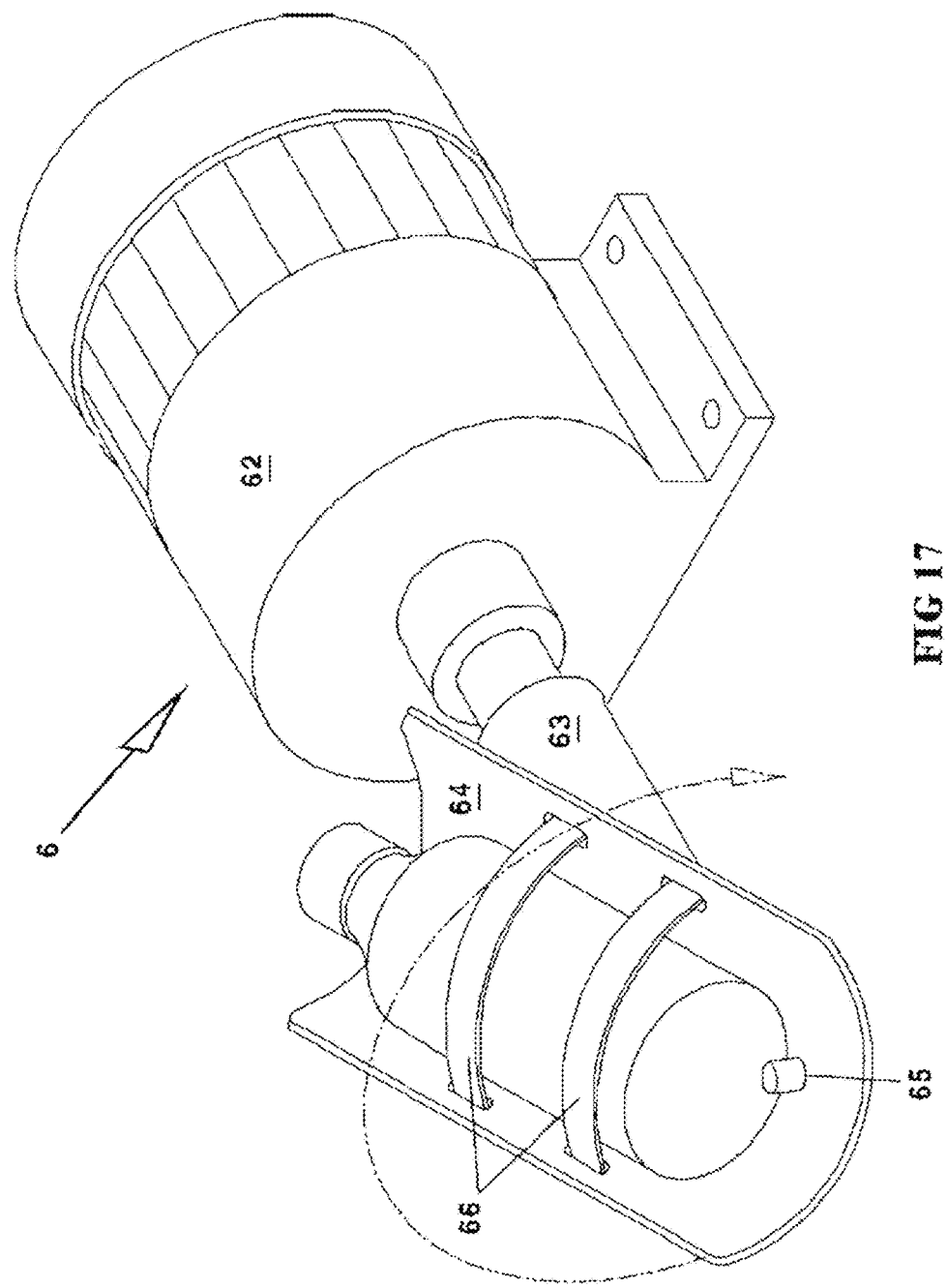
Figure 19:
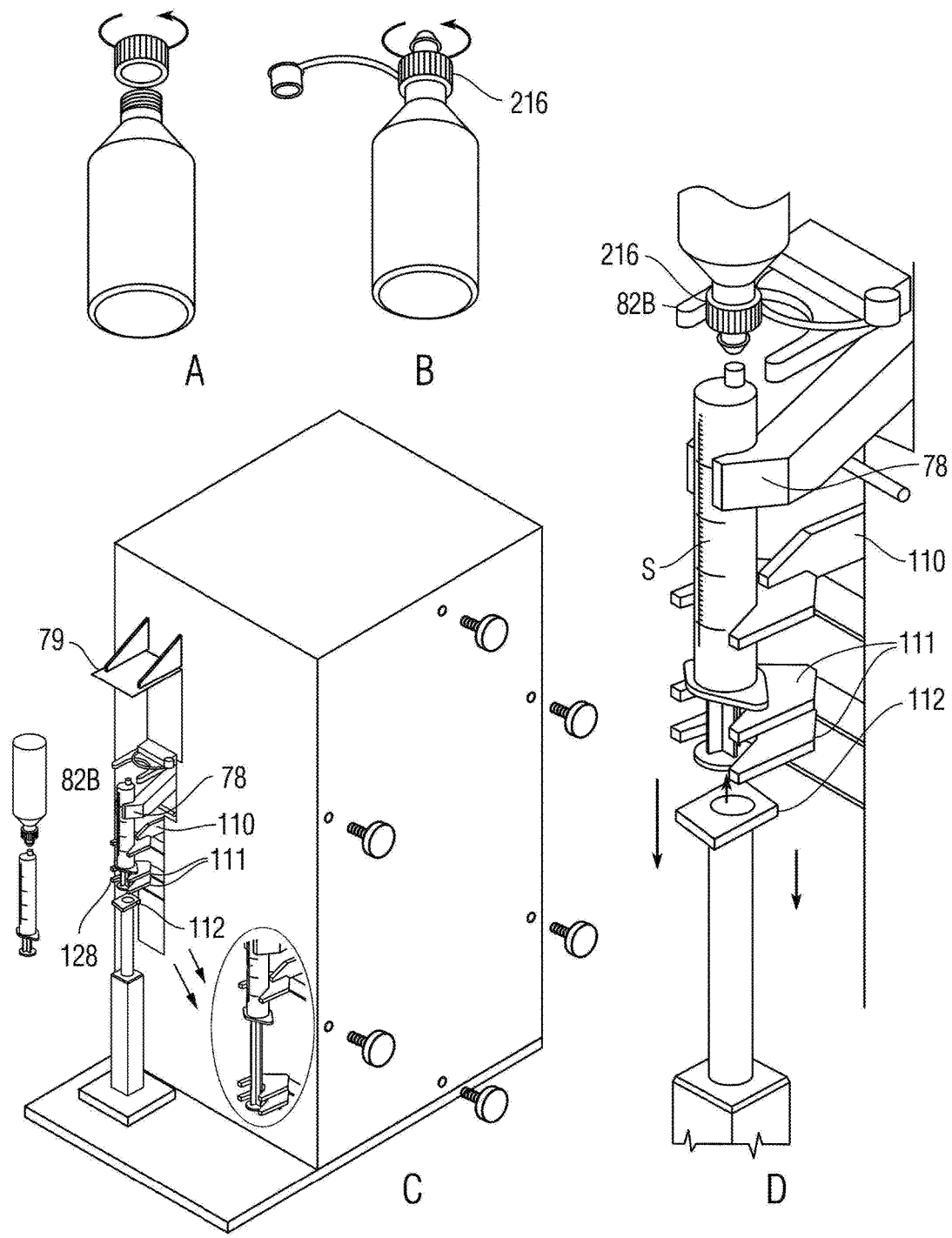

FIG. 17 is a perspective view of an alternative, remote medication container shake station 6.

FIGS. 18A-18F represent sequential illustrations of the process for filling a syringe S using a standard commercially available "Baxa" cap 214;

FIG. 18A shows the original cap being removed;

FIG. 18B shows the Baxa™ cap 214 applied onto the neck of a container;

FIG. 18C shows the syringe S inserted into the Baxa™ cap 214;

FIG. 18D shows the medication container and the syringe S combination rotated up-side-down;

FIG. 18E shows both the medication container and the inserted syringe S inverted and placed into the yoke 82A;

FIG. 18F shows the syringe clamped by the filler finger grippers 78 and platform 79.

FIGS. 19A-19D are sequential illustrations of the process for filling a syringe S using an OEM-Baxa™ Cap with self sealing valve 216.

FIG. 19A shows the original cap removed;

FIG. 19B shows the Baxa™ Cap with Self Sealing Valve 216 tightened onto the neck of the container;

FIG. 19C shows the medication container turned upside down;

FIG. 19D shows the neck of the container held on center by the slotted yoke 82B and properly aligned with the syringe S for filling by pulling the syringe plunger downward.

FIGS. 20A-20E are sequential illustrations of the process for filling a syringe S using a flow restrictor (no valve) 210;

FIG. 20A shows the medicine bottle cap removed;

FIG. 20B shows the valveless flow restrictor 210 inserted into the neck of the container;

FIG. 20C shows the syringe S inserted into the valveless flow restrictor 210;

FIG. 20D shows the syringe S and medicine container inverted;

FIG. 20E shows the inverted syringe S and medicine container inserted into the yoke 82A.

FIGS. 21A-21E are sequential illustrations of the process for filling a syringe S using a flow restrictor (with valve) 212.

FIG. 21A shows the medicine bottle cap removed;

FIG. 21B shows the self sealing flow restrictor insert 212 inserted into the neck of the container;

FIG. 21C shows the medicine container and self sealing flow restrictor insert 212 inverted;

FIG. 21D shows the syringe S and medicine container inverted for insertion to the filling station;

FIG. 21E shows the inverted syringe S and medicine container inverted at the filling station.

Figure 22:
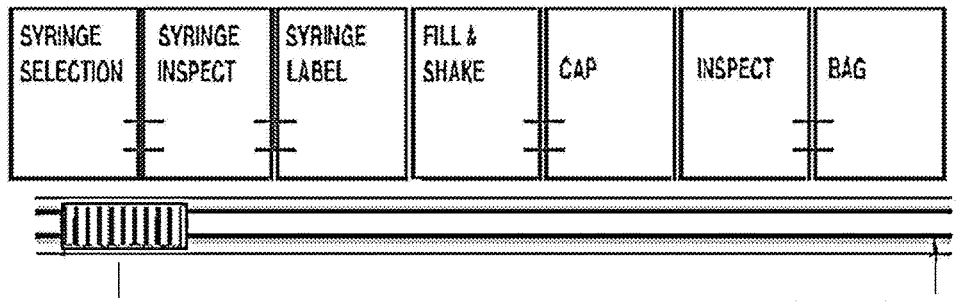

FIG. 22 is a process drawing with one operator and three grouped stations (Option 2).

Figure 23:
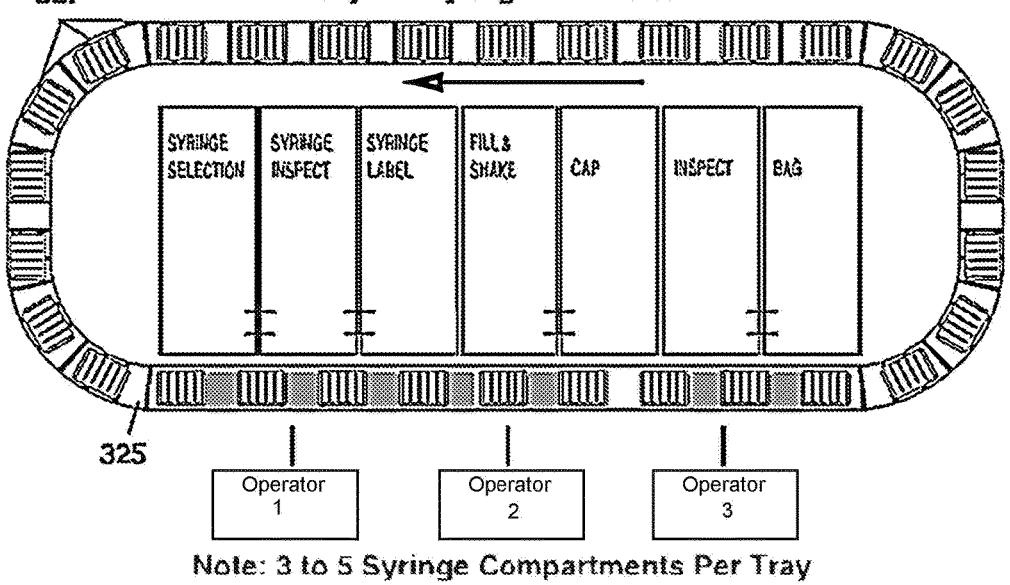

FIG. 23 is a process drawing with three operators and three and three grouped stations (Option 3).

Figure 24:
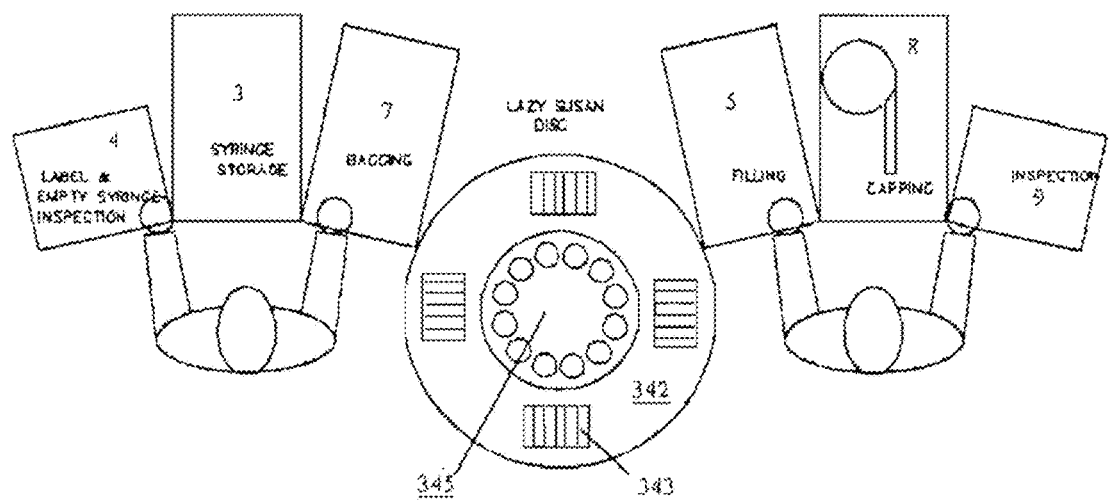

FIG. 24 is a process drawing with two operators situated around a lazy Susan (carousel-like) disc 342.

Figure 25:
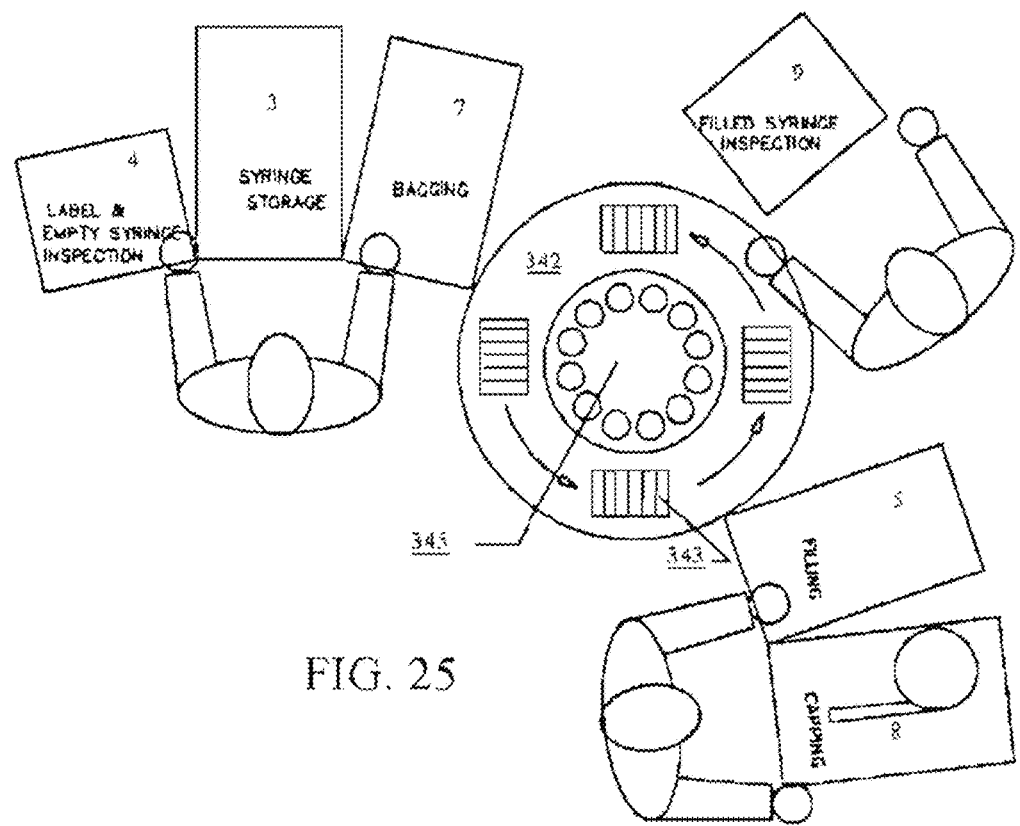

FIG. 25 is a process drawing with three (3) operators situated around a lazy Susan (carousel-like) disc 342.

Figure 26:
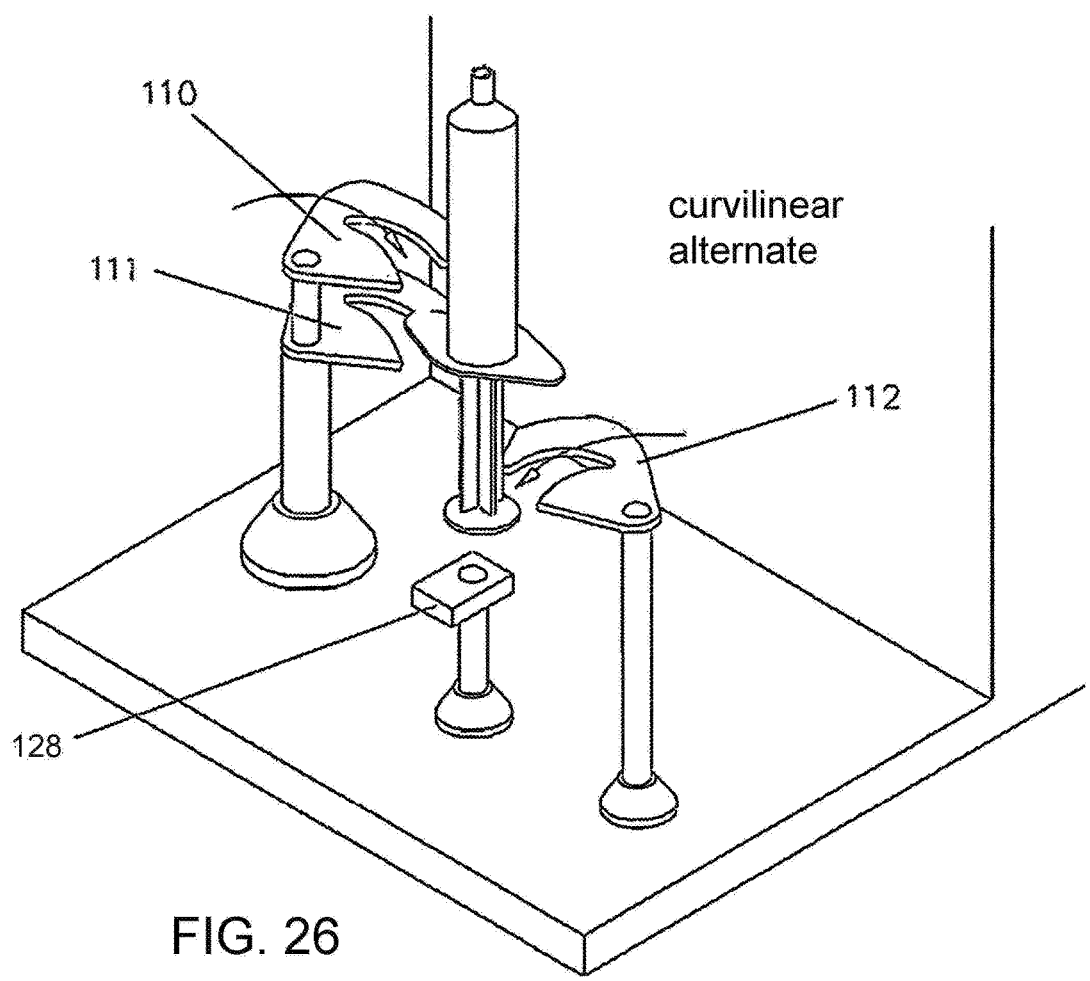

FIG. 26 illustrates an embodiment of a syringe gripping mechanism having curvilinear distal ends.

Figure 27:
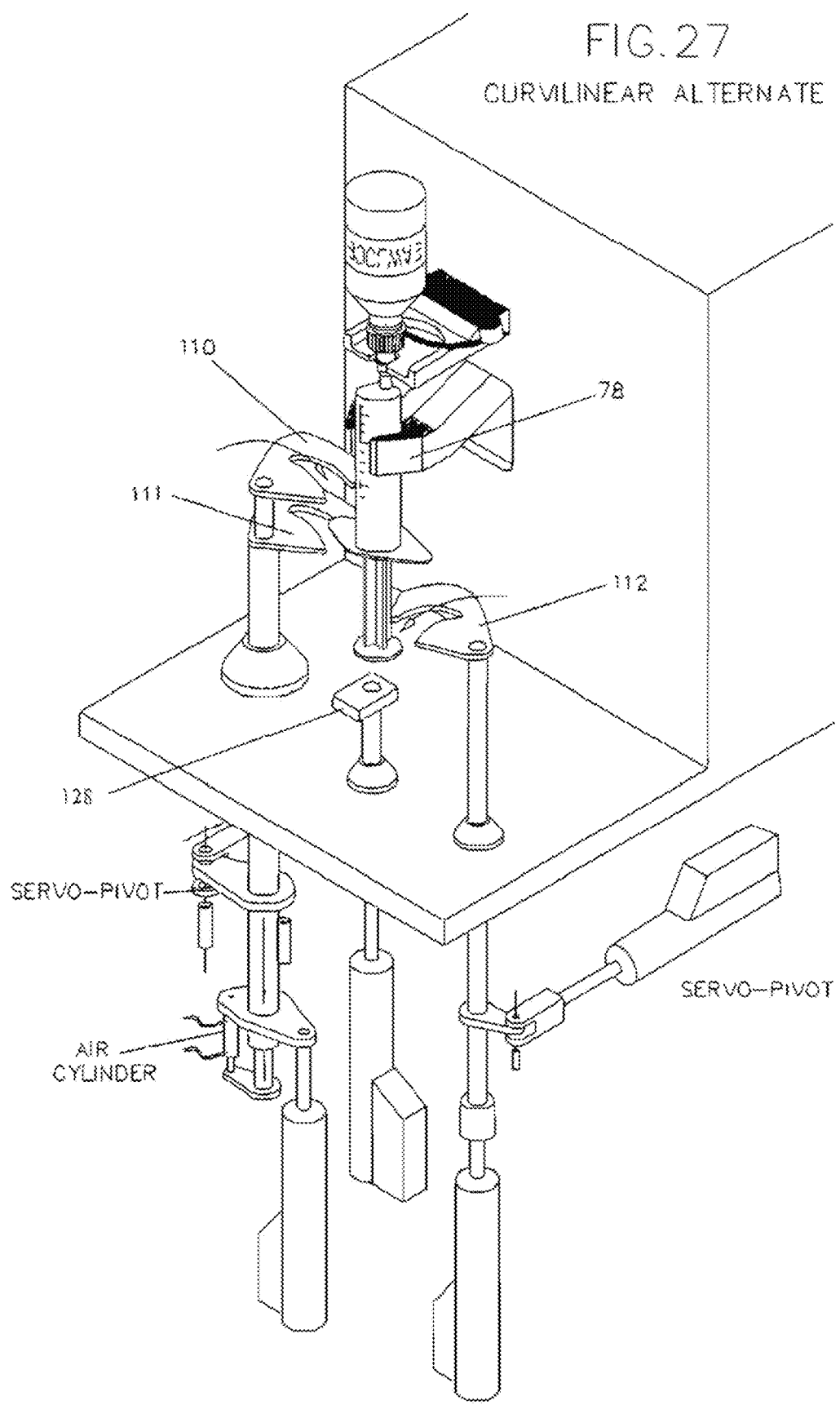

FIG. 27 illustrates an embodiment of a syringe gripping mechanism having curvilinear distal ends along with its drive mechanism.

Figure 28:
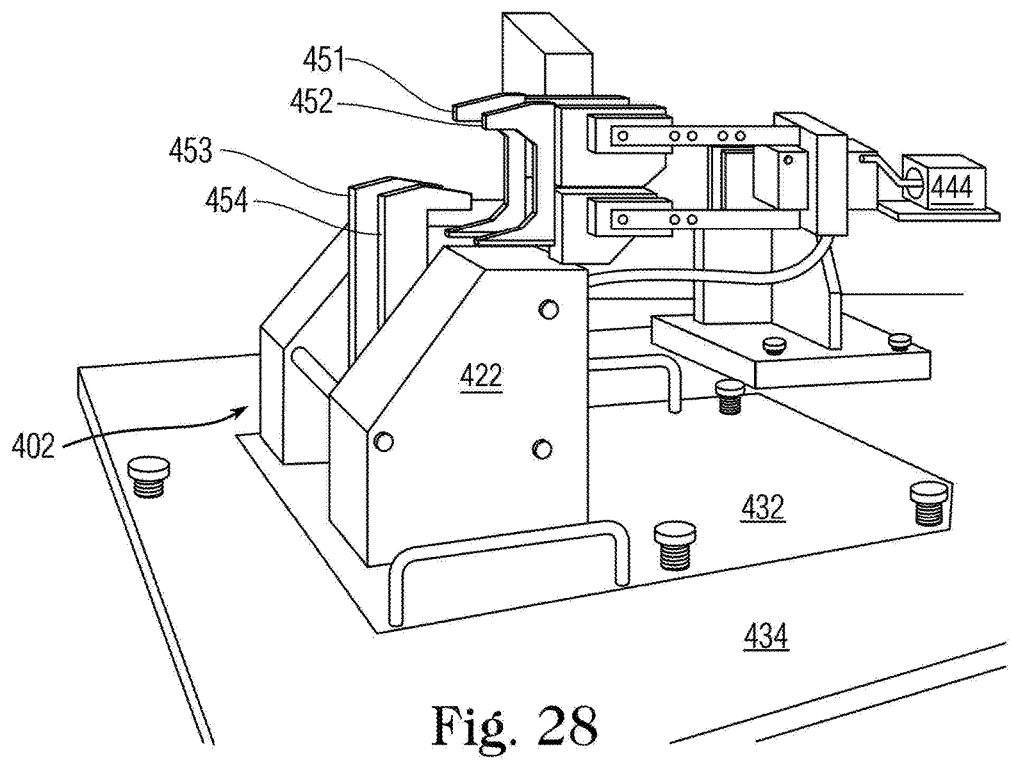

FIG. 28 is a side perspective view of the labeling fixture 402.

Figure 29:
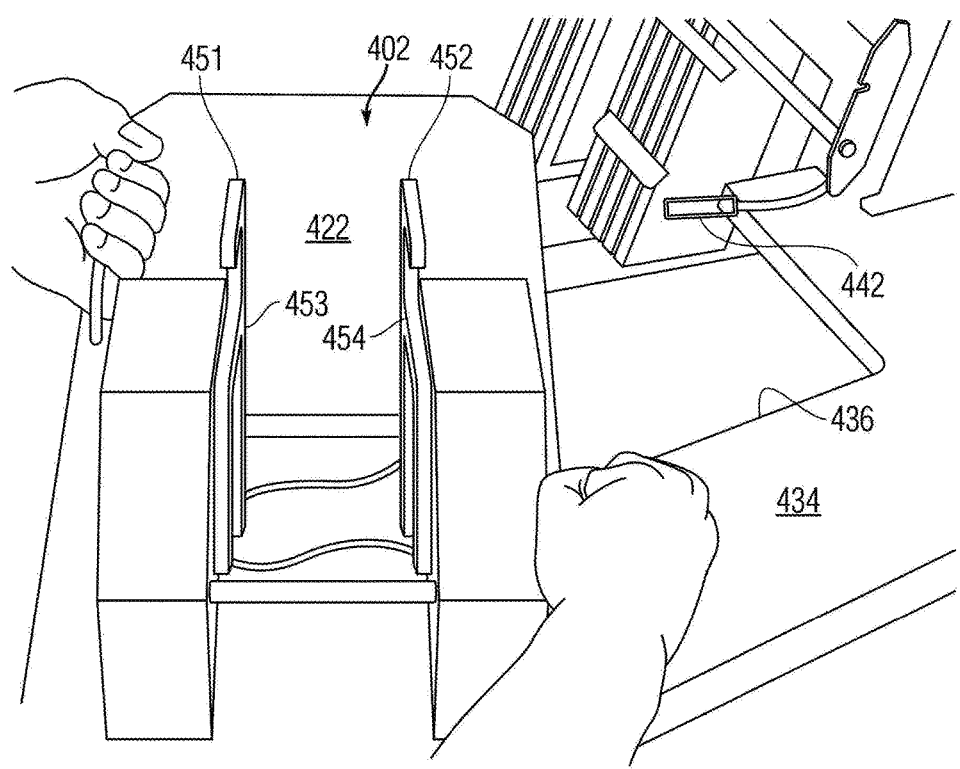

FIG. 29 is a side perspective view of the labeling fixture 402 removed from subplate 432.

Figure 30:
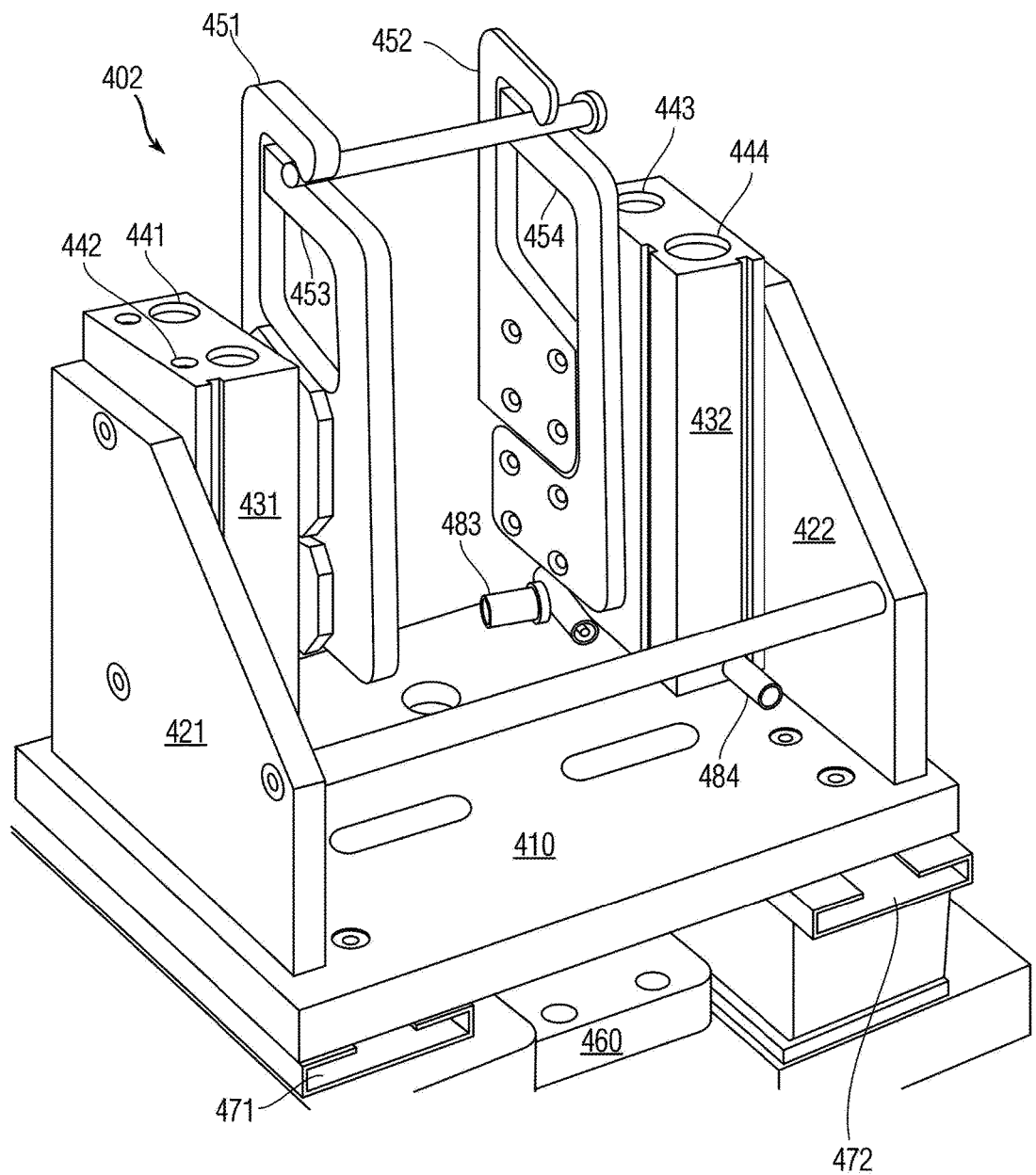

FIG. 30 is a perspective view of a syringe labeling fixture 402 holding a small-size syringe S.

Figure 31:
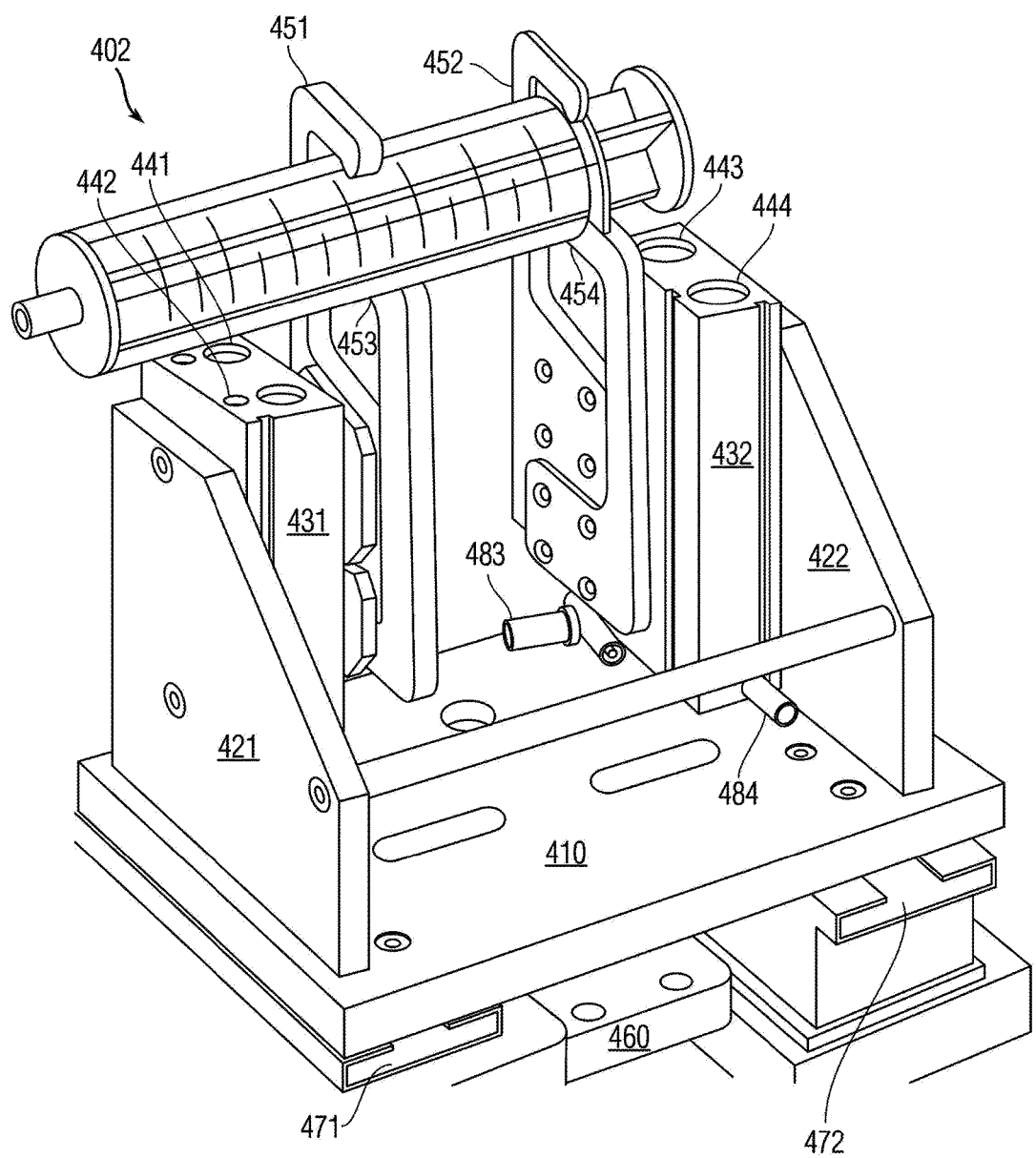

FIG. 31 is a perspective view of a syringe labeling fixture 402 holding a large-size syringe S.

FIGS. 32A and 32B are composite views of the syringe labeling fixture 402 illustrating how it interfaces with the label wiper L of a pressure sensitive label applicator.

FIG. 32A is a side view showing the label wiper L removed.

FIG. 32B is a side view showing the label wiper L advanced.

Figure 33:
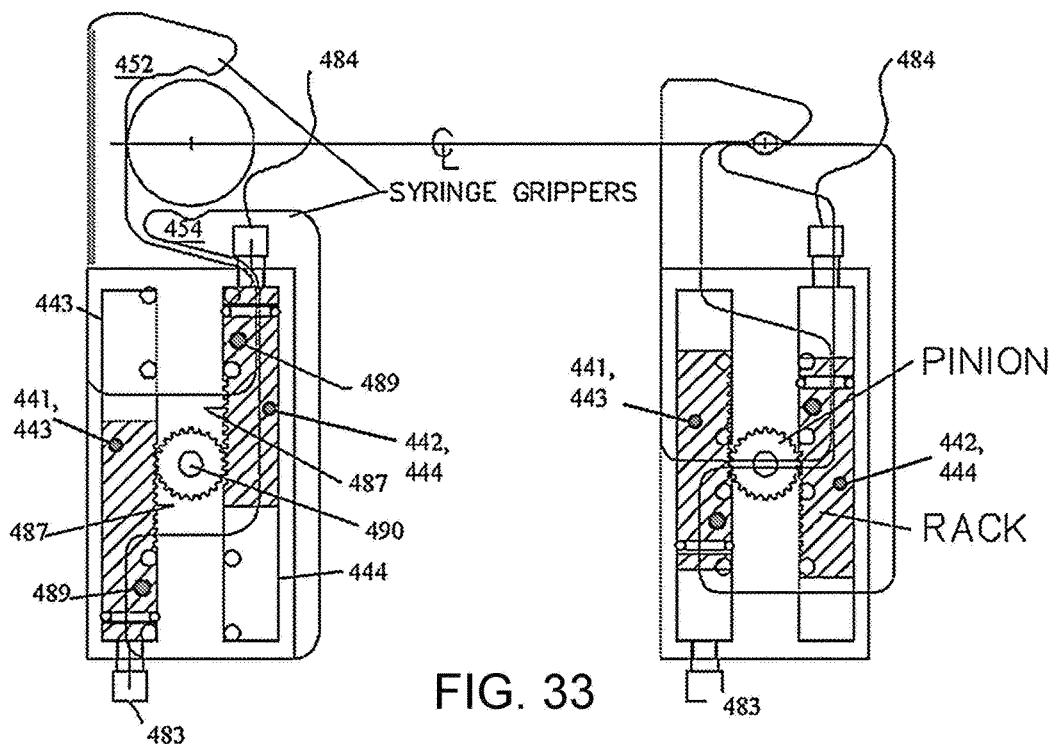

FIG. 33 is a composite cross-section illustrating a rack-and-pinion mechanism to compel synchronous movement of each pair of sled assemblies 441,442 and 443,444.

Figure 34:
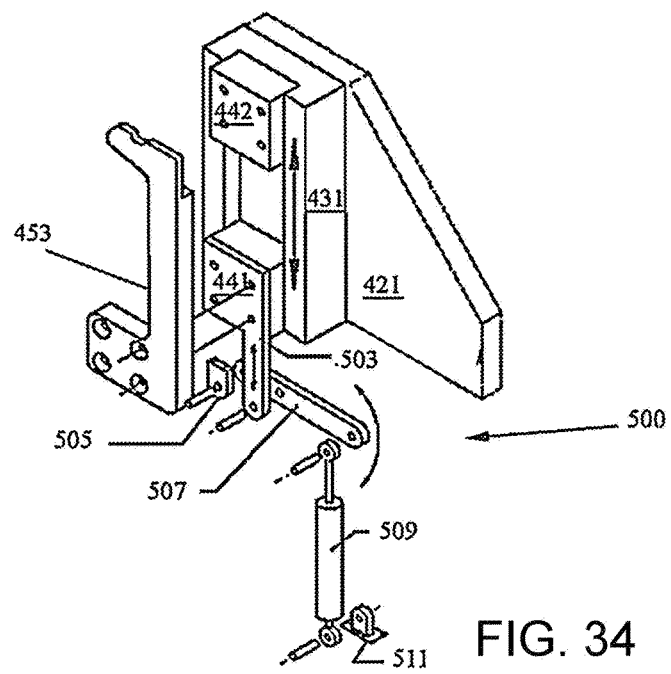

FIG. 34 is a perspective drawing showing the syringe size sensor 500 mounted to lower gripper 453.

Figure 35:
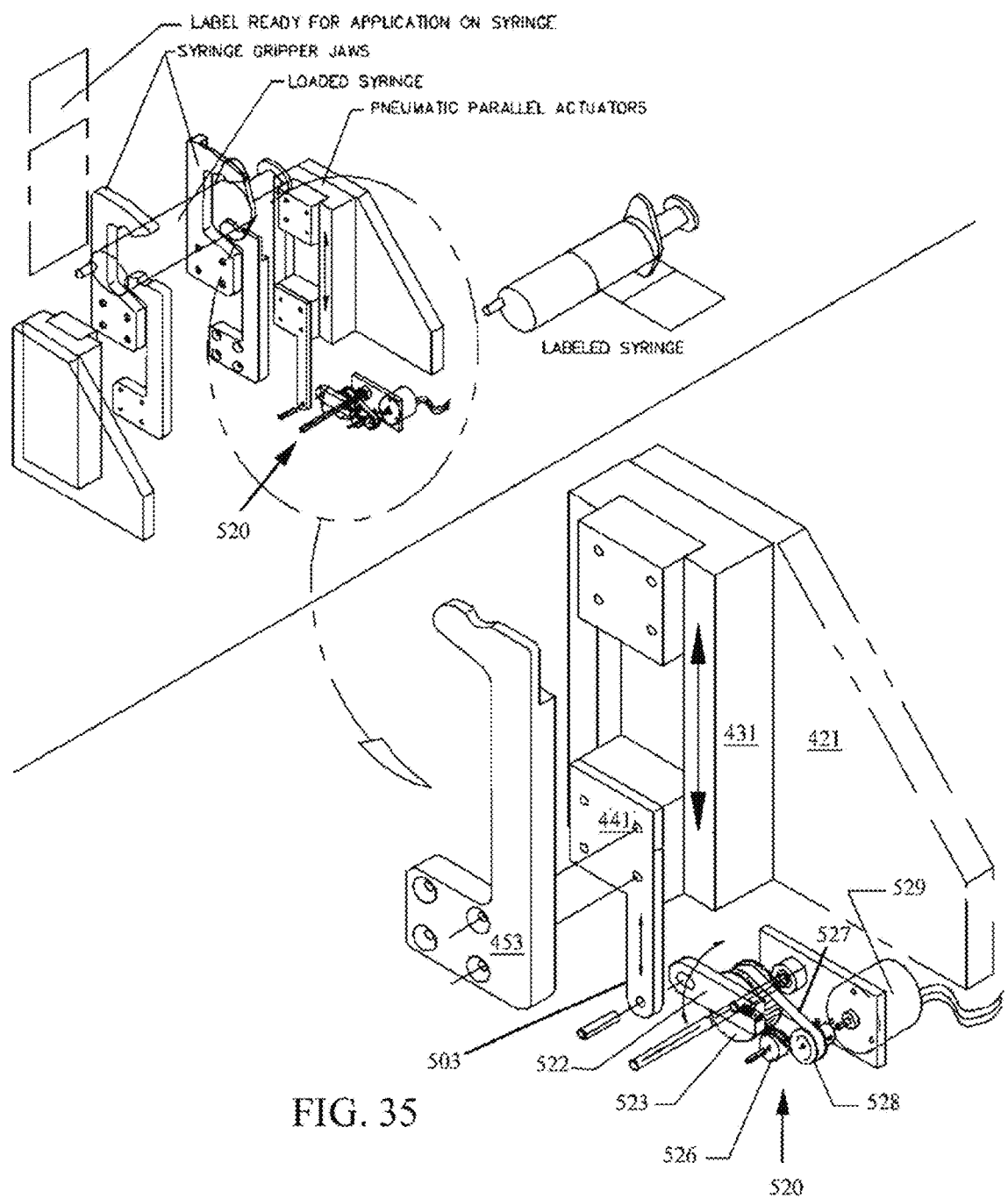

FIG. 35 is a perspective drawing showing an alternative embodiment of a syringe size sensor 520.

DETAILED DESCRIPTION OF THE PREFERRED EMBODIMENT

For the purposes of promoting an understanding of the principles of the invention, reference will now be made to the exemplary embodiment illustrated in the drawings and described below. The embodiment disclosed is not intended to be exhaustive or limit the invention to the precise form disclosed in the following detailed description. Rather, the embodiment is chosen and described so that others skilled in the art may utilize its teachings. It will be understood that no limitation of the scope of the invention is thereby intended. The invention includes any alterations and modifications in the illustrated device, the methods of operation, and further applications of the principles of the invention to oral and/or enteral syringe filling systems as would normally occur to one skilled in the art to which the invention relates. As herein defined the term oral syringe is meant to include enteral syringes, and vice versa, both to the express exclusion of parenteral syringes. The present invention includes both the system hardware as well as the process for preparing and tracking prescriptions of enteral/oral syringes by a series of integrated manual and automated steps with respect to preparing the syringe and the bulk medicine, and subsequently bringing the series together for filling the former from the latter. The bulk medicine is typically supplied in manufacturer-supplied medicine containers with conventional screw-on caps. These conventional caps do not permit penetration by a syringe tip. Consequently, to facilitate processing in the present system specialized caps may need to be provided to specification, or may be replaced or retrofitted with a container/syringe interface (cap, closure or neck insert) to provide a penetrable orifice. As described more fully below, the retrofit may be accomplished in a number of ways. One solution is a flow restrictor, e.g., a press-in plug inserted into the neck opening of a medication container which enables an enteral/oral syringe to enter its center hole and withdraw an amount of liquid from the medication container while the medication container is positioned up-side-down. Another is a modified manufacturer-supplied cap. Specifically, the present invention contemplates six container/syringe interface variations: (1) a standard manufacturer-supplied (Baxa or Baxa equivalent) valve-less medicine container cap with opening, (2) a modified manufacturer-supplied (Baxa or Baxa equivalent) medicine container cap that is retrofit to include an integral valve (typically, a duckbill valve), (3) a valve-less flow restrictor, (4) a flow restrictor with an integral valve (typically, either a linear or a Z-shaped slit), (5) a two-piece, cap comprising an outer portion 220 with a common outer diameter for all three standard sizes of medication container, and a self-sealing insert, and/or (6) a cap 221 comprising a common outer diameter for all three standard sizes of medication container and having an integral self-sealing insert.

FIG. 5 is a composite view of the embodiments of the container/syringe interfaces according to the invention. Two valveless embodiments include the flow restrictor 210 and OEM/Baxa Cap 214 at left, and four valved embodiments include the valved flow restrictor 212, the valved self-sealing flow restrictor 212 integrally formed into, or combinable with, the common diameter outer portion 220 or 221, and a modified/self-sealing OEM/Baxa Cap 216. All may be adapted to fit a variety of medicine bottle types and sizes.

The valved flow restrictor 212, OEM/Baxa Cap 216 and common outer diameter caps 220, 221 all include a self-sealing valve that closes when the syringe terminal discharge is removed to prevent leakage when the medication container is in the inverted position at the fill station.

Both flow restrictors 210, 212 comprise a press-fitted open plug inserted into the neck opening of a medication container. This enables an enteral/oral syringe to enter its center hole and withdraw an amount of liquid from the medication container while the container is positioned up-side-down. This syringe filling procedure must be repeated for each syringe to be filled.

If the medication container with open flow restrictor 210 requires shaking this must be done manually with original screw cap replaced over the neck. The above procedure must be repeated every time shaking is required regardless of whether the same medication is being filled into multiple syringes. Also, the original cap must be placed over the Medication bottle and its press-in insert, during storage, to ensure cleanliness.

OEM/Baxa Caps 214 (see FIG. 5) are the commercially available "Baxa" screw on adapter caps which are applied to the necks of medication bottles to enable them to fill enteral/oral syringes. The standard commercially available "Baxa" cap consists of a female threaded cap to fit over medication bottles and is available in sizes to accommodate most medication containers. It enables an enteral/oral syringe to enter its center hole and withdraw an amount of liquid from the Medication container while the Medication container is positioned upside down. For the syringe to be removed from the medication container, both syringe and medication bottle must be up-righted. Once up-righted, the syringe can be removed from the up-righted medication bottle with no leakage. If the medication bottle requires shaking at any given time, it can be done manually or in a separate shaker by closing the tethered cap and fastening the bottle into the shaking mechanism (see FIG. 17 below).

The valved OEM/Baxa Cap 216 (see FIG. 5) is preferably modified/constructed with an elastomeric check valve member 225 held captive in the plastic cap body 219. Examples of self-sealing valves include check valves and simple diaphragms with a linear or a Z-shaped slit. Again, it is important to remember that valved interfaces 212, 216 can be left inverted at the filling station 5 (FIG. 2) and even shaken without leaking, whereas valveless interfaces 210, 214 (FIG. 5) do not prevent leakage. Thus, valveless interfaces 210, 214 compel removal of the syringe/container combination from the filling station 5 after each filling operation.

The elastomeric seal 225 (see FIG. 5) of the valved OEM/Baxa Cap 216 is fitted within an aperture in the flange of cap 219. In its simplest form the elastomeric seal 225 may be a resilient, penetrable membrane with a small hole or slot (such as a pinhole) punched at its center, and preferably formed of silicone or other rubber. The hole in the seal 225 expands as the tip of a syringe S is inserted to permit pressurization of the container 104 and/or filling of the syringe (by vacuum) as described below. On withdrawal of the syringe tip the resilient elastomeric seal 225 returns to its original shape closing the hole and preventing leakage of the fluid contents of the bottle 104.

FIG. 5 also shows cross-sections of alternative container/syringe interfaces 210, 212 which comprise a flow restrictor fitted as a plug-in insert into the neck of the medicine container. The flow restrictor is an annular body sized to conform to the inside of the medicine container neck and adapted for a friction fit therein, and may be formed with ribs as described above for this purpose. The interface 212 defines a central conduit, and the elastomeric seal 215 is fitted within interface 212 across this conduit to serve as a penetrable seal as described above.

As still another option, any conventional cap, such as Baxa's AdaptaCap™ bottle adapter cap may be used (as shown in U.S. Pat. No. 4,493,348 referenced above) and simply modified or equipped by the manufacturer or after-market with a penetrable elastomeric seal such as check valve 225, or other suitable self-sealing valve. In yet another embodiment of the present invention, a container/syringe interface includes an outer portion 220, 221 that will have the same outer circumference for use on any of the three standard sizes of medication containers. It can be used with a purchased, self-sealing insert, such as valved flow restrictor 212, or the insert can be integrally formed within the outer portion 221. The interface between the medication container and the self-sealing insert will hold the outer portion 220, 221 securely onto the top of the medication container, locating the outer part on center with the opening of the medication container. The cap with outer portion 220, 221 may also include a tethered dust cap similar to the Baxa type cap, as shown in FIG. 5. In one preferred embodiment, the 2D bar code, described in further detail below, is affixed to the top of the tethered cap. The common outer diameter of outer portion 220, 221 for all standard sizes of medication container caps can serve as a common means of locating the medication container on center with the yoke at the fill station. The common size of the flange 222 of the outer portion 220, 221 of the instant cap embodiment may also facilitate transportation of the medication containers when used with a carousel designed to hold a single diameter syringe/container interface.

For purposes of definition, the invention described herein may be used with any of the foregoing and the term "container/syringe interface" means any of the foregoing and/or their equivalents that permit penetration by the terminal discharge of an oral/enteral syringe. A preferred embodiment of the invention is herein described below with reference to the flow restrictor with valve interface 212 of FIG. 5. Process and system configuration variations specific to each of the container/syringe interfaces are also described below.

Figure 7A:
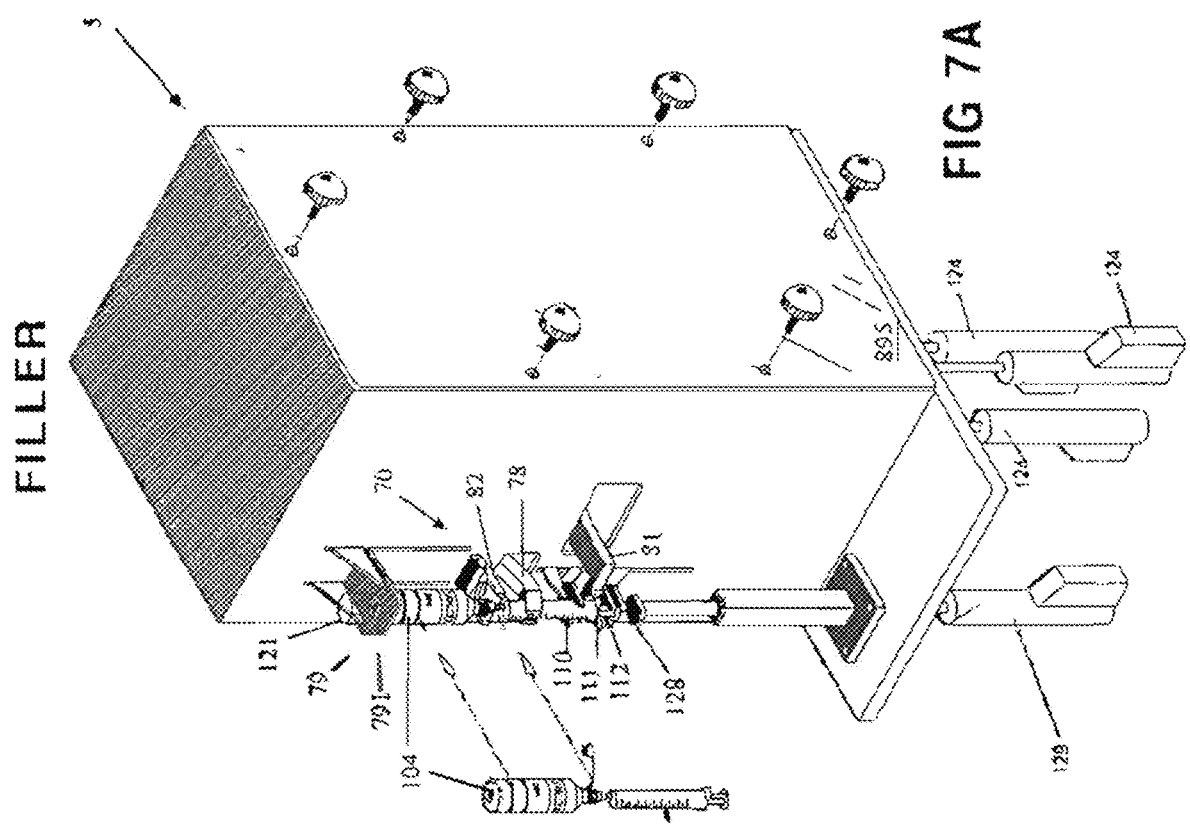
FIG. 7A is an enlarged perspective view of a semi-automated syringe fill station 5 for filling die syringes S.

The support fixture illustrated in FIG. 7A comprises a fixed-position container holding yoke 82 that engages the container/syringe interface 210, 212, 214, 216 (see FIG. 5) suspending the assembly. Note that the four syringe-filling closure variations container/syringe interlaces 210, 212, 214, 216 suitable for use with the present system necessitate differently sized/shaped container holding yokes 82, and for this reason yoke 82 may be removably-mounted to filling station 5 by thumb-screws or the like, allowing replacement with different sizes and shapes. For example, FIG. 7C I shows a container holding yoke 82A with aperture configured to seat the protruding stem of an interface 214, 216, while FIG. 7C II shows a container holding yoke 82B with aperture sized to seat the neck of a container in which an interface 210, 212 has been inserted. The platform thickness of yoke 82 is also important as valved versus valveless closures may require differing degrees of syringe terminal discharge insertion and so some yokes 82 may need to be very thin. The operator can choose the appropriately-configured yoke 82, and in all such cases the yoke 82 facilitates easy frontal insertion of the container/syringe combination and stably supports the container.

Figure 7B:
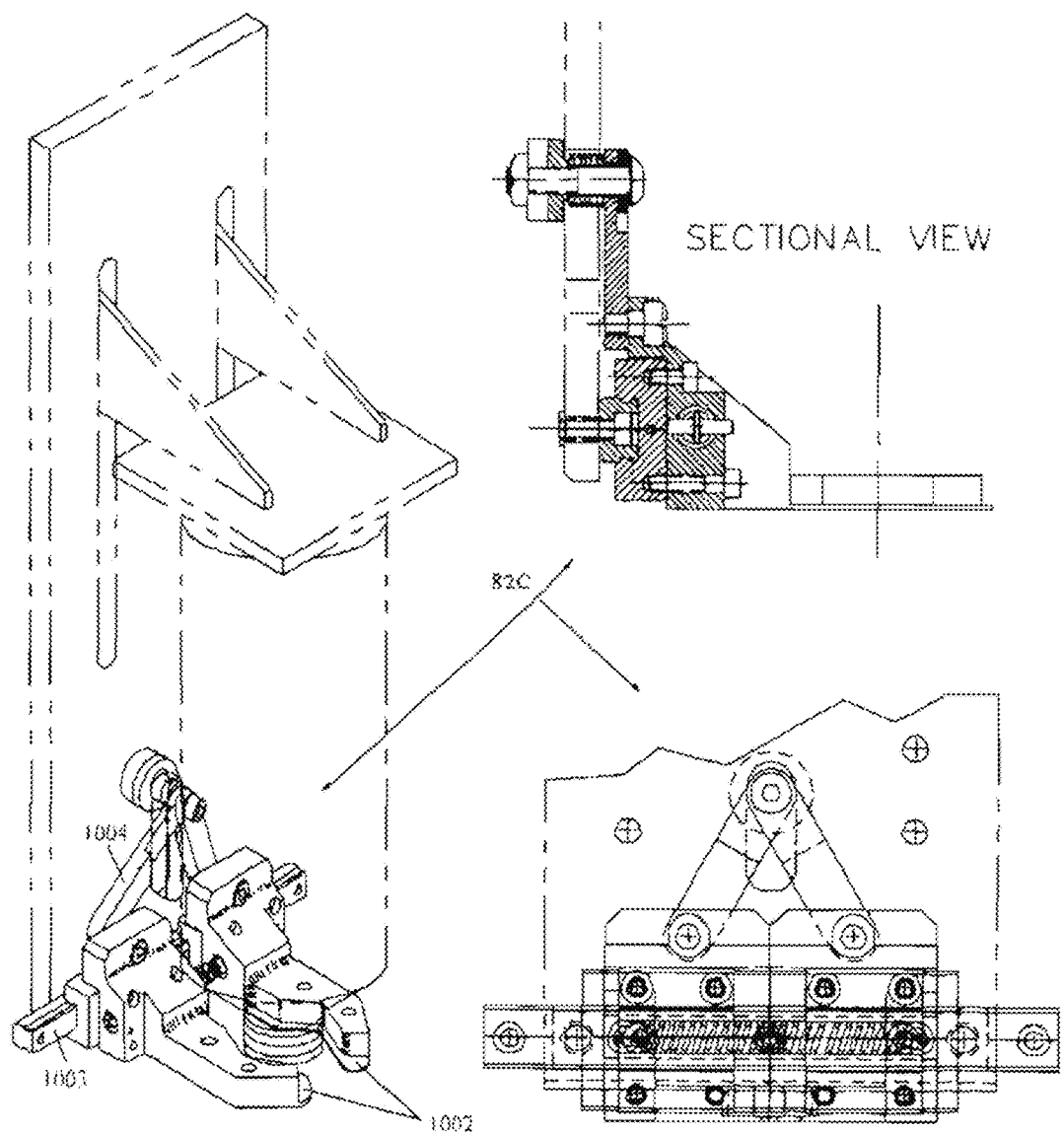
FIG. 7B is a composite view of a self-centering spring loaded bottle gripper assembly 82C used as an alternative to fixed yokes 82 of FIG. 7A.

FIG. 7B is a composite view of a self-centering spring loaded bottle gripper assembly 82C used as an alternative to fixed yokes 82 of FIG. 7A. While the yoke 82 may suffice to align the syringe S on-center with the filler, yoke 82 makes it difficult to leave the medication container in place whilst replacing the syringe with another, for batch filling. Yoke(s) 82 tend to interfere with the path to inserting a new syringe. It would also be advantageous to provide a fixture better able to withstand the shaking cycle and which can fit into the limited space available. For this purpose the self-centering spring loaded bottle gripper assembly 82C of FIG. 7B employs an adjustable clamping device.

Specifically, FIG. 7B employs a pair of spring-loaded jaws 1002 slidably mounted on a ball-slide track 1003 for slidable separation. A pair of trammel arms 1004 are coupled from each jaw 1002 to a common pivot and thereby maintain symmetry of the jaws 1002 as they separate. The operator rests the container onto the lips of jaws 1002 and pushes the container straight back, separating the spring-loaded jaws, until the jaws spring tight about the container and it is gripped. Note that the jaws 1002 are formed to hook around the container and have a lowermost flange to serve as a reference to ensure that all syringes are uniformly located in the vertical dimension.

The following table maps the container/syringe interface variations to requisite variations in the filling station 5 (FIG. 2 III 5) and points out the advantages of utilizing the self-sealing valve in the Baxa cap or flow restrictor:

| Container/ Syringe Interface | Filling station 5 container neck positioning device | Need to invert container and syringe 180° and then rotate 180° after filling syringe? | Able to shake at fill station? | Able to fill multiple syringes at one time without removing container from fill station? |
| --- | --- | --- | --- | --- |
| OEM/Baxa cap 214 | Yoke 82A (FIG. 7C I) | Yes | No | No |
| OEM/Baxa cap with self sealing valve 216 | Yoke 82A (FIG. 7C I) | No | Yes | Yes |
| Flow restrictor 210 | Yoke 82B (FIG. 7C II) | Yes | No | No |
| Flow restrictor with self sealing valve 212 | Adjustable clamping device 82C (FIG. 7C III) | No | Yes | Yes |
| Valved self-sealing two-piece 220 | Yoke 82D (FIG. 7C IV) | No | Yes | Yes |
| Valved self-sealing one-piece 221 | Yoke 82D (FIG. 7C IV) | No | Yes | Yes |

With reference to FIGS. 7A and 7D, upper, middle, and lower syringe gripping arms 110, 111 and 112 are staged in a vertical orientation that will allow the selected syringe S to be easily slid into the fill zone, with plunger lifting arm 128 fully retracted. As different syringe sizes have different exterior dimensions, the vertical orientation of syringe gripping arms 110, 111 and 112 may be adjusted prior to syringe insertion to ensure that the syringe body can easily fit between the medication container and middle arm 111, which, as will be described, rests below the hilt or flange of the syringe. The syringe S is connected to the medication container and both are held by yoke 82. Once the medicine container and syringe S are in place, and the start button is pressed, a guard is closed around the filling station, or by some other signal from the processor, a pair of syringe finger grippers 78 close about the syringe S and hold it securely. Syringe finger grippers 78 are air operated for opening and closing, or may optionally be servo-driven, and have a servo-operated mount which moves the finger's to the center of the body of the syringe. This feature advantageously ensures that the syringe tip is exactly on center with the yoke, as syringe tip to body eccentricity varies on syringes sized from 10 mL to 60 mL. For syringe sizes between 10 mL and 60 mL, the tip of the syringe is eccentric to the body diameter, whereas on syringe sizes from 0.5 mL to 5 mL, the tip is concentric on the body diameter. The in and out motion of the servo mount locates the grippers 78 to grip the center of the syringe body so that the center of the tip is always on center with the yoke, regardless of its eccentricity to the body of the syringe. Additionally, a bottle holder platform 79 lowers to sandwich the medicine container against the container holding yoke 82. The bottle holder platform 79 has an aperture 791 through it and a scanner 121 is mounted above the aperture 791 to read the machine readable label on the bottom of the container 104. An articulating syringe locator guide 81 (FIG. 7A) comprises a pair of offset Fingers on a bracket that push against syringe finger flanges, effectively rotating the syringe to a known orientation. This ensures that all offset-tip syringes (terminal discharge offset from center axis) are in proper orientation for filling. One skilled in the art should understand that the syringe locator collar 81 is not required for concentric tipped syringes and may be articulated out of the way.

Once in the fill position in loading station 70 with syringe finger grippers 78 closed around it, the syringe S is engaged by the upper 110, middle 111 and lower 112 arms, and a plunger lifting arm 128 that extends upward from below, all of which collectively grip and operate die syringe S in order to effectuate the filling process as described below.

The syringe locator guide 81 withdraws to its home position. Upper arm 110 lowers and middle arm 111 raises to close on the syringe body hilt or flange (see FIG. 19 for detailed view). This creates a sandwiching effect to hold the body of syringe S securely. Lower arm 112 then moves downward onto the upper side of the syringe plunger disc and plunger lifting arm 128 rises to a position just under the syringe plunger, thus working in concert with lower arm 112 to create a sandwiching effect on the syringe plunger disc captured between them. Upon command from the operator or programmer, arm 112 and arm 128 work in concert to perform priming and/or filling of the syringe S. The use of both arm 112 and arm 128 allow the filling station to exert both a pushing and a pulling effect on the syringe plunger as the program dictates, thus allowing better control of the plunger location during both priming and filling. Upper and middle arms 110 and 111 may also work m concert to push syringe S further upward towards the medication container as necessary to ensure that the closure of the medication container hasn't relaxed its fit with the tip of syringe S. The priming sequence is determined by syringe size and viscosity of medicine to be filled. After priming is complete and with the piston ail the way up, the piston is then pulled downward to fill with the correct dose.

As stated in the foregoing Table the yoke 82 will vary depending on the syringe interface variation. Specifically, the OEM/Baxa cap 214 will require yoke 82A (FIG. 7C I), the OEM/Baxa cap with self-sealing valve 216 will require Yoke 82A (FIG. 7C I), the valveless flow restrictor 210 will require yoke 82B (FIG. 7C II), and the flow restrictor with self sealing valve 212 will require the adjustable clamping device 82C (FIG. 7C III).

The invention relies on a conventional network architecture which includes a local O/ESPS (oral/enteral syringe packaging system) computer. The O/ESPS computer is interfaced to a hospital host computer and receives enteral/oral syringe prescription instructions therefrom (however, the O/ESPS system may be used as a stand-alone unit independent of any interface with another computer). In the majority of circumstances, physicians submit prescriptions for enteral/oral syringes electronically to the hospital host computer and these prescriptions are communicated to the O/ESPS computer for fulfillment. The interface serves to parse/extract those enteral/oral medication prescriptions from all prescriptions submitted.

The local O/ESPS computer is programmed to know what must occur at each station and monitors to ensure that each step of the process is completed satisfactorily and that all decision rules are complied with. The local O/ESPS computer software implements a Medication Container Orientation and Log-In Process for semi-automated preparation and storage of bulk medicine containers to be used in filling and packaging enteral/oral syringes, and a Batch Fulfillment Process for semi-automated filling and packaging of enteral/oral syringes using the stored bulk medicine containers. In general terms, the semi-automated Medication Container Orientation and Log-In Process comprises the following steps:

a. Pharmacy technician (operator) removes the manufacturer's cap from bulk medicine container received from the pharmaceutical manufacturer and installs one of several possible container/syringe interface variations (to be described), in all such cases facilitating insertion of an enteral/oral syringe terminal discharge into the container. The present system is adaptable to filling syringes with each interface variation. The system may include an optional motorized capper/decapper station to assist with the removal of the manufacturer's cap and the application of a threaded interface.

b. Variable information such as container fill size, manufacturer's expiration date, and product lot number are entered into the O/ESPS computer automatically as much as possible by bar code scan, or manually by the Pharmacy Technician under the supervision of the Pharmacist. First, software guides operator to scan the manufacturer's barcode label. However the barcoded information is often incomplete. Any missing variable information such as container till size, manufacturer's expiration date, and product lot number can be derived and manually entered into the O/ESPS computer by the Pharmacy Technician.

c. If needed, the O/ESPS computer instructs the Pharmacy Technician which of the container/syringe interfaces to select for recapping the medication container. The O/ESPS obtains this information from the medication database. In addition the storage location of the correct size container/syringe interface will illuminate.

d. The O/ESPS computer auto-assigns an expiration date to the medication container based on either the manufacturer's expiration date or the expiration date defined by pharmacy-policy. The pharmacy expiration date policy is determined by the date the container is opened at the medication container log in station plus the number of days the Pharmacist determines that the medication should expire. The O/ESPS computer uses the date that is the soonest to determine the effective medication container expiration date.

e. Software automatically prints a new unique 2D barcode label.

f. The 2D barcode label is placed on the center of the base of the container.

g. Software guides the operator to rescan the manufacturer's barcode on the container label and the 2D barcode on the base of the container;

h. If scanning checks, software guides operator to place medication container in a particular (logged) storage facility location.

The semi-automated Batch Fulfillment Process for the valved flow restrictor 212 (see FIG. 5) comprises the following steps:

a. Software guides operator to retrieve medication container from particular (logged) storage facility location;
b. Operator loads medication container into fill station;
c. The 2D barcode on die medicine container bottom is scanned to make sure that all medication issues relating to that medicine container have been addressed, including correct medication, refrigeration, expiration and light-sensitive storage;
d. Software guides operator to pick a syringe of proper color and size;
e. Software automatically prints label for the syringe;
f. The label is rescanned to ensure that the information is correct;
g. Operator places the syringe in a syringe size/color station at the labeling station that verifies that the proper size and color syringe has been selected. The syringe size/color station may also check for proper orientation. If the syringe size/color station passes, the pre-printed label is attached to the syringe;
h. Operator scans the 2D barcode on the syringe at the filling station.
i. If needed, the medication container is shaken for the duration and intensity required by the shaking mechanism to which the container is attached;
j. Operator positions the syringe at the filling station;
k. System/software automatically fills the syringe from medicine in medication Container
l. Operator caps filled syringe at semi-automatic capper;
m. Operator scans the syringe at the fill inspection station;
n. System automatically inspects the syringe at a visual inspection station for proper weight and/or volume;
o. System/software automatically prints bag that the syringe will be packaged in;
p. Software automatically scans the printing on the bag to make sure that it is correct;
q. Operator places the syringe in the bag at the bagging station, and the system confirms that the syringe was placed in the bag, and seals the bag with the syringe in it.

All medication containers and medicines in those containers that have been logged in, each size syringe, each size container/syringe interface, the syringe labels, syringe bags, print media, etc. are automatically inventoried. As an item is used or consumed, an accounting of the amount of that item remaining is maintained.

Track, Trace and Validation software monitors and documents the entire process from the prescription approval by the pharmacist, log-in of the medication container through each step of the packaging process.

Figure 1:
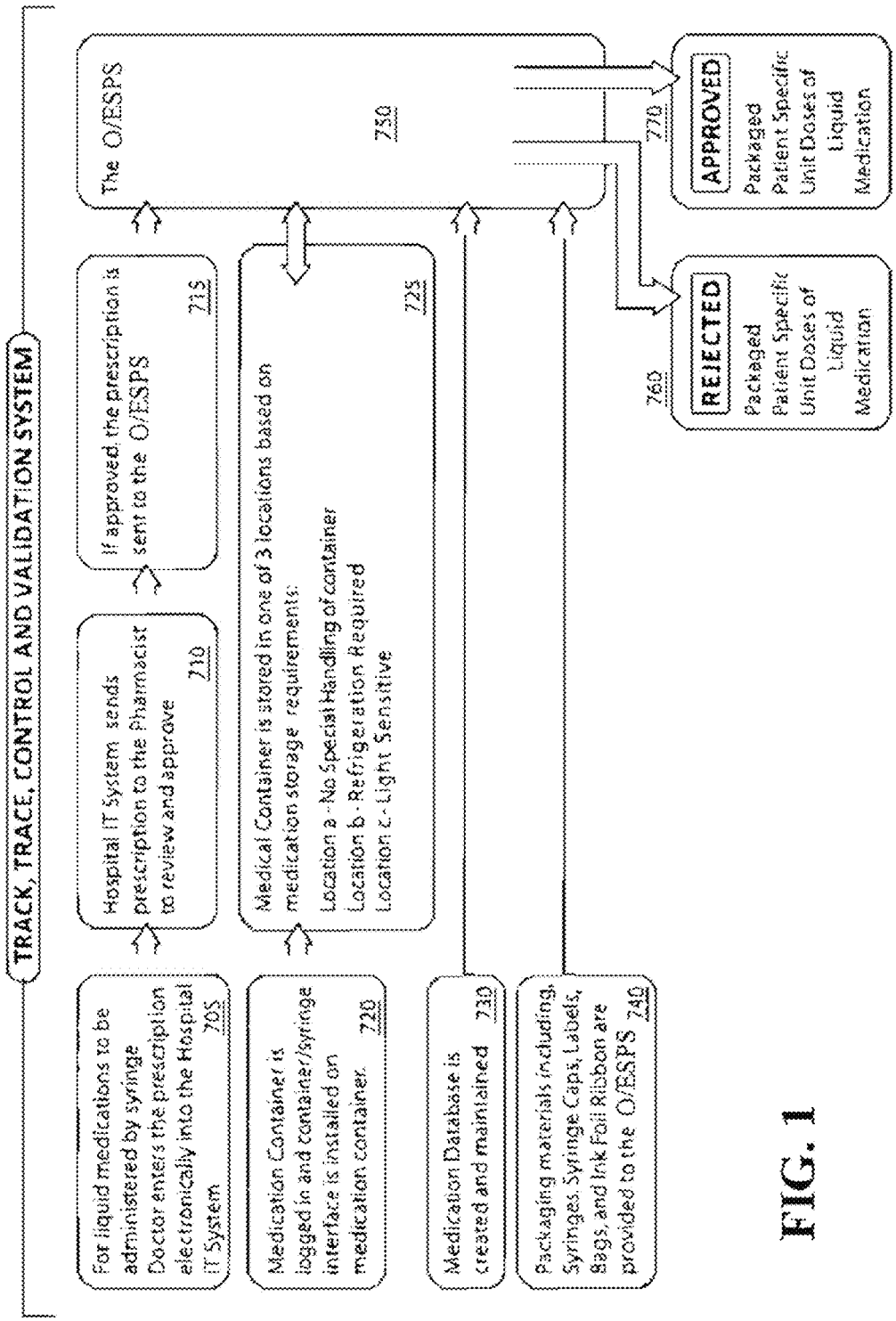
FIG. 1 is a flow chart of the overall method of the invention.

FIG. 1 is a high level flow chart of the overall method of the invention. The following method steps are performed semi-automatically with some manual intervention by or interaction with an operator for filling patient-specific enteral/oral syringes on a just-in-time basis. Note that "semi-automatic" necessarily entails manual intervention/interaction which has a propensity for introducing mistakes. The present method and apparatus is specifically designed to avoid mistakes and maintains comprehensive track-and-trace validation of each manual step:

At step 705 a physician writes an enteral/oral medicine prescription which is electronically entered into existing hospital host computer (as all prescriptions are so logged).

At step 710 the existing hospital host computer communicates the enteral/oral medicine prescription to the hospital pharmacy for approval. A pharmacist will typically review it.

If approved, then at step 715 the prescription is transmitted the local computer of the O/ESPS (oral/enteral syringe packaging system) of the present invention. The enteral/oral syringe prescription is added to a batch fulfillment queue at the local O/ESPS computer. As described below the queue is multi-soiled so that all prescriptions for a particular type of medicine (e.g., Acetaminophen, cough syrup, etc.) can be fulfilled together, and at periods throughout the day an operator may run a batch fulfillment queue (typically batches are run a few times each day).

At commencement of batch fulfillment, the O/ESPS system preferably guides the operator in retrieving the appropriate medication container from O/ESPS storage (as will be described). Such guidance presupposes that a library of medicine containers is maintained and that each such medicine container be logged into the O/ESPS system so that, its location and contents are known to the local O/ESPS computer. Consequently, as a precursor to batch fulfillment each new medication container is logged into O/ESPS storage by a barcode, RFID scan or similar identification scan (e.g., of the manufacturer's barcode). The manufacturer-supplied medicine container cap must be replaced, retrofit, or supplied by the manufacturer in a form that enables an enteral/oral syringe to enter a center hole and withdraw an amount of liquid from the medication container while die medication container is positioned upside down, and the syringe S then removed from the container without leaking. There are four container/syringe interface variations suitable for use with the present system (see FIG. 5 and the detailed descriptions associated with it). All this occurs at step 720.

At step 725 based on the medication container login, the O/ESPS system guides the operator in properly storing the new medication container. The O/ESPS system (as described below) includes separate storage locations for three types of medication containers: Location 1—No Special Handling of container; Location 2—Refrigeration Required; Location 3—Light Sensitive medication container (refer to FIG. 2 II, refs a-c). Each storage compartment within each location may be enclosed by a magnetically-actuable door so that access to each location may be electronically controlled by the local O/ESPS computer. Alternately, each storage compartment within each location may be illuminated by an LED light, so that access to the proper location may be electronically guided by illumination of the proper LED. As another alternative, each storage compartment within each location may be equipped with a light curtain so that the local O/ESPS computer can monitor access to the proper location. All these and other suitable forms of user-guidance/selection are considered to be within the scope and spirit of the present invention. In all such cases, the end result is an O/ESPS storage library of different enteral/oral medicines in their bulk containers, each properly logged in and stored in its corresponding storage location a-c.

Similarly, at step 740 an inventory of packaging materials is maintained, including empty syringes in an array of sizes, syringe caps, labels (for barcodes), and ink foil printer ribbon.

In support of the O/ESPS system, at step 730 a comprehensive medication database is maintained at the O/ESPS computer. The O/ESPS medication database includes the following:

1. Medication Information.
   a. Medication name.
   b. Manufacturers barcode number.
   c. Written information that corresponds to manufacturer's barcode number.
   d. Whether medication needs to be shaken, if so, the frequency, intensity, and duration.

e. Whether the medication needs to be refrigerated, if so refrigeration policy required
f. Whether the medication is light sensitive, if so light sensitive protection required.
2. Product information (pertaining to individualized medication containers logged in).
   a. The O/ESPS 2D barcode number assigned to that specific container. The label containing this information is placed on the base of the container.
   b. Fill size of that container in cubic centimeters (cc) or milliliters (ml).
   c. Current amount of product remaining in that container after deducting for previous fills extracted by the syringes.
   d. Manufacturer's Expiration Date
   e. Date the medication container is logged-in at the Medication Container Log-In Orientation System.
   f. Pharmacy Policy Expiration Date: Container open date plus number of days before container expires (determined by pharmacist).
   g. Effective Expiration Date. This is the soonest of the manufacturer's expiration date or the date that die container is open plus the number of days that the open container will expire. (Pharmacy Policy Expiration Date).

Given all of the foregoing, at step 750 an operator may at any convenient time commence the batch fulfillment process. The detailed substeps of the batch fulfillment process 750 are described below and illustrated in the block diagram of FIG. 3.

Referring back to FIG. 1, after each enteral/oral syringe has been filled and packaged during batch fulfillment 750, it is inspected and either rejected at step 760 or approved at step 770.

The above-described method is herein implemented in several detailed embodiments of a system suitable for preparing patient-specific enteral/oral syringe doses. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated.

A presently-preferred embodiment of the physical system componentry is described below with reference to FIG. 2.

Figure 2:
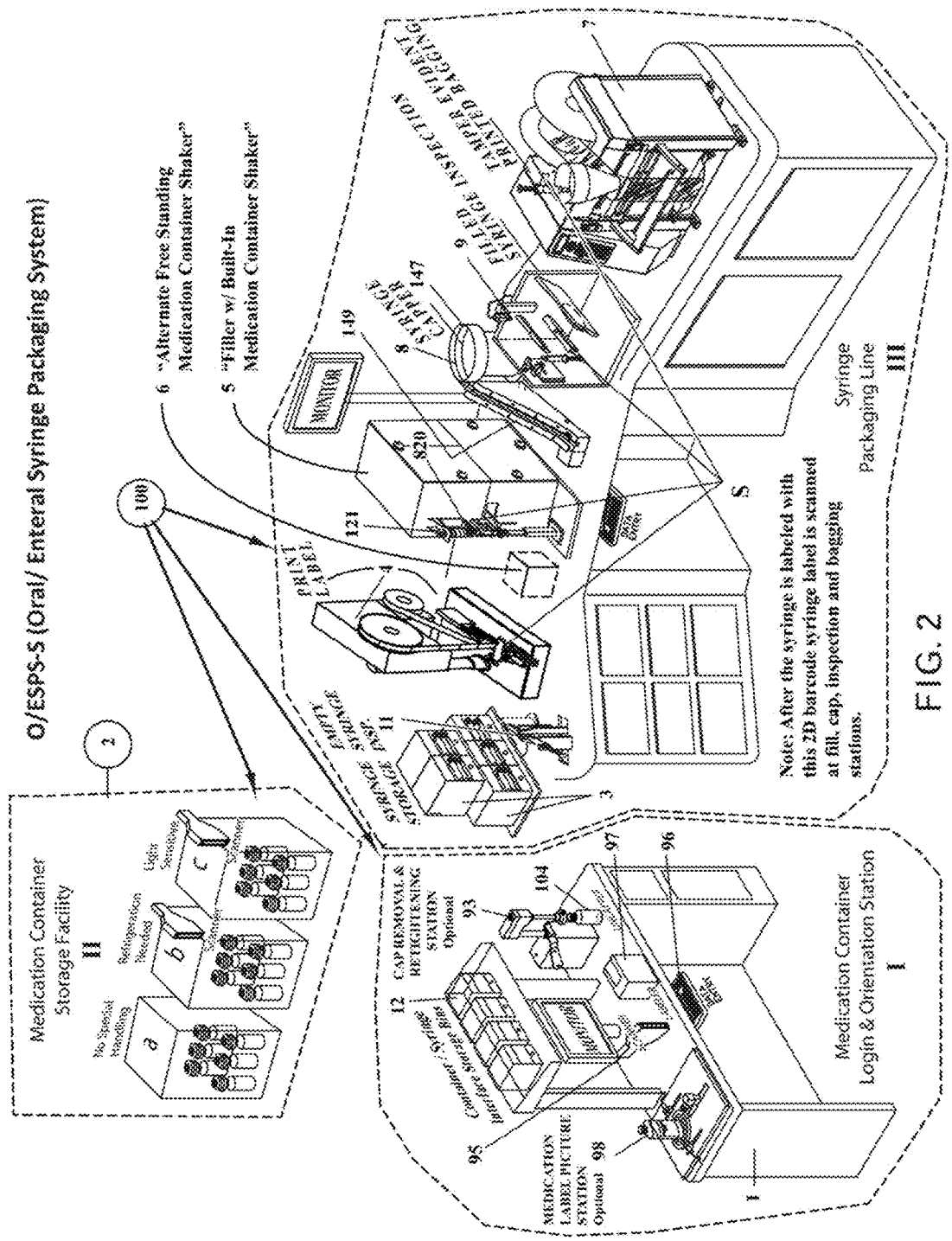
FIG. 2 is a perspective view of the entire pharmacy automation system 100 according to an embodiment of the invention.

As seen in FIG. 2, the pharmacy automation system 100 for packaging enteral/oral syringes generally comprises a standalone Medication Container Login & Orientation Station 11, with an included array of container/syringe interface storage bins 12. In addition, a proximate or remote Storage Facility II is provided for storing all logged in medication containers, with separate locations for the three types of medication containers: (a) Location 1—No Special Handling of container; (b) Location 2—Refrigeration Required; (c) Location 3—Light Sensitive medication container. The final component of the system includes the syringe packaging line III.

In an alternate embodiment of the present invention, Storage Facility II of FIG. 2 may be substituted with an automated medication storage cabinet (AMSC) with rotary shelves, such as the commercially available MedCarousel® sold by McKesson Automation Solutions, or similar models sold by TALYST, OMNICHLL, SAPIENT AND US MEZZANINES. AMSC units such as these are currently being utilized in hospital pharmacies. These systems automate the medication management process from ordering the medication, stocking the medication on the system's rotating shelves, and presenting the medication to the pharmacy technician at the time the medication needs to be utilized to fill the prescription on the O/ESPS system. Therefore, the accuracy and efficiency of medication dispensing and inventory management is increased. Aided by rotating shelves, pick to-light, bar code scanning and comprehensive integrated workflow software, the AMSC systems guide the pharmacist to medication storage locations, improving picking speed and accuracy. AMSC systems such as the MedCarousel® can handle storage of refrigerated as well as non-refrigerated medicines.

In conjunction with the O/ESPS, an AMSC system would operate as follows:
1. Two AMSC systems would be utilized, one for non-refrigerated medications and the other for refrigerated medications. The containers that require light protection would be stored on the non-refrigerated AMSC system.
2. After the medication container was oriented and logged in to the O/ESPS, the AMSC would assign a location to store that medication.
3. The 2D bar code on the container would be scanned.
4. The shelf that the medication was to be stored on would be positioned in front of the pharmacy technician. A light would appear over the location on the shelf on which the medication was to be stored.
5. The pharmacy technician would place the medication at that location.
6. At the start of the next O/ESPS production run, the O/ESPS would list the prescriptions to be filled by medication. This information would be sent to the AMSC(s).
7. The pharmacy technician would then remove the medication containers that are presented and scan them. The medication containers would be kept in the same order in which they are removed by the technician. This order corresponds to the order in which rite medication will be used to fill syringes on the O/ESPS system.
8. After the production run, the medication containers would be returned to the AMSC(s) in the same order in which they were removed therefrom. The pharmacy technician would scan the medication containers. The AMSC(s) would present the pharmacy technician with the proper shelf and light the position to which the medication container should be returned. The pharmacy technician would return the medication container to the indicated location in the AMSC(s).

A syringe storage bin 3 (see FIG. 2 III) is provided for storage of empty syringes, and a syringe label printer and labeler station 4 (see FIG. 2 III) is provided next. Next, a syringe size/color inspection station 11 is provided. These are followed by a syringe filling station 5 with integrated medication container shaker assembly 820 (as described below). An alternative embodiment is a stand-alone shaking station.

At the filling station 5 the medication container with container/syringe interface 212 or 216 (see FIG. 5) is manually inverted and inserted. An overhead clamp lowers against the topside base of the medicine container to clamp the container against its holder. This provides an opportunity to inspect the medication container's 2D barcode (located in the center of the container's bottom) via the Lexan™ disc found in platform 79 (see FIG. 7A) to verify that it is the correct medication. The medication container is shaken if necessary. The syringe's 2D barcode is inspected and, if correct, the syringe is inserted into the medication container via the container/syringe interface. A plurality of servo-driven fingers (to be described) grip and stabilize the syringe S. The fingers manipulate the syringe plunger to prime and fill the syringe. When all syringes have been filled with the medication, the medication container is returned to storage. This process continues until all syringes for that prescription production run have been filled.

Next, a semi-automated capping station 8 is used to place a cap (fed from an inclined capping chute 149) on the open tip of the filled syringe.

After each syringe S is filled and capped it is loaded into a vision inspection station 9 which verifies the presence of the cap, the piston position within the syringe, that the syringe is filled with medication, and that an excessive number of air bubbles are not present.

Lastly a bag printing and sealing station 7 bags the filled syringe in a barcoded bag.

The purpose and function of each of the foregoing stations 1-5, 7-9, and 11 (see FIG. 2 I, II, III) will become clearer in the context of a detailed description of the Medication Container Orientation and Log-In Process (step 720), and Batch Fulfillment Process 750.

Medication Container Orientation and Log-In Process (step 720)

The O/ESPS system guides the operator in properly equipping and storing each bulk medication container. As described above, the manufacturer-supplied medicine container cap must be replaced, retrofit, or supplied by the manufacturer in a form that enables an enteral/oral syringe to enter a center hole and withdraw an amount of liquid from the medication container while the medication container is positioned upside down, and the syringe S then removed from the container without leaking. Thus, at step 720 (FIG. 1) the manufacturer-supplied medicine container cap may need to be provided to specification, or replaced or retrofitted with a container/syringe interface to provide a penetrable orifice. As described more fully below the retrofit may be accomplished in a number of ways. Thus, the present invention contemplates four container/syringe interface variations: (1) a standard manufacturer-supplied (Baxa or Baxa equivalent) valve-less medicine container cap with opening, (2) a modified manufacturer-supplied (Baxa or Baxa equivalent) medicine container cap that is retrofit to include an integral valve (typically, a duckbill valve), (3) a valve-less flow restrictor, and/or (4) a flow restrictor with an integral valve (typically, either a linear or a Z-shaped slit). Again, all four variations as shown in FIG. 5 are described below in detail.

It is envisioned that medication containers may be provided to the hospital pharmacy for use with the present system in such a way that will minimize or possibly eliminate any need for the Medication Container Orientation and Log-In Process (step 720). For example, medication containers may be provided for use with one or more of the following features:

1) standardized caps with self-sealing valve (such as, for example, the above-referenced Baxa™ or Baxa-equivalent) medicine container cap with penetrable opening);

2) standardized containers; and/or 3) barcoded or RFID-coded containers that already contain the information that a pharmacy technician would otherwise need to input during the Medication Container Orientation and Log-In Process (step 720).

A combination of all three features listed above would minimize or eliminate the need for the Medication Container Orientation and Log-In Process (step 720). However, for purposes of complete description it will be assumed that such features are lacking in OEM-supplied medication containers and so the Medication Container Orientation and Log-In Process (step 720) will herein be described in detail.

Figure 4:
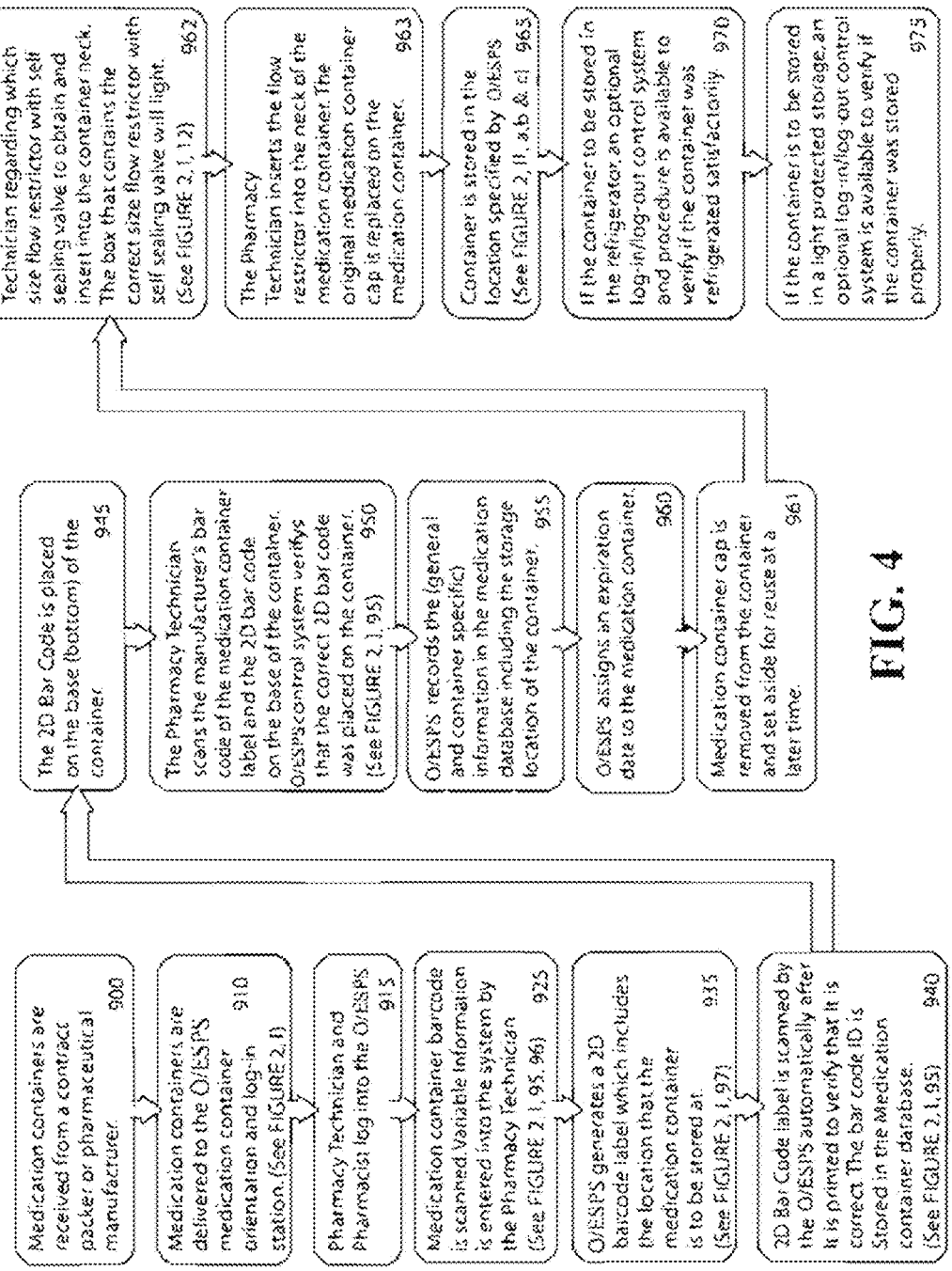
FIG. 4 is a more detailed block diagram of the medication container orientation and log-in process 720 of FIG. 1.

Referring now to FIG. 4 which is a flow diagram of the Log-In process for the valved flow restrictor 212 (see FIG. 5), at step 900, medication containers are received from a contract packager or pharmaceutical manufacturer.

At step 910, medication containers are delivered to the O/ESPS Medication Container Login & Orientation Station 1 (FIG. 2).

At step 915 the pharmacist and operator logs into the local O/ESPS computer.

At step 925 the manufacturer-provided medication container barcode is scanned. Variable information is entered into the system by the pharmacy technician.

At step 935, the labeler shown at the Medication Container Login & Orientation Station 1 (see FIG. 2 I) generates a 2D barcode label which includes the location that the medication container is to be stored at. The 2D bar code is manually placed on the bottom of the container (or on the container/syringe interface) at step 945.

At step 940, the bar code label is automatically scanned/inspected immediately after printing to verify that its contents are correct and the bar code ID is stored in the O/ESPS database.

At step 945, the bar code label is adhered to the base (bottom) of the container.

At step 950, both the 2D bar code placed on the base of the container and the pharmaceutical manufacturer's barcode are scanned using a scanner resident at the Medication Container Login & Orientation Station 1 and the manufacturer's bar code on the medication container label are scanned to verify that the correct 2D bar code was placed on the base of the container.

At step 955 all general and container specific information, inclusive of Product Information and label photograph, is recorded in the local O/ESPS computer database, including the storage location of the bulk container.

At step 960, the O/ESPS local computer assigns an expiration date to the medication container. The expiration date is predetermined by pharmacy policy. The pharmacy policy expiration date is determined by the date the container is opened at the Medication Container Log In Station 1 plus some number of days the Pharmacist determines that the medication should expire.

At step 961, the medication container cap is removed from the container by the operator and is set aside for later reuse.

At step 962, the O/ESPS local computer instructs the pharmacy technician regarding which size flow restrictor with self-sealing valve to obtain and insert into the container neck. To guide the operator, the box 12 containing the correct size flow restrictor with self-sealing valve is preferably illuminated as shown in FIG. 2.

At step 963, the pharmacy technician inserts the flow restrictor with self-sealing valve into the neck of the medication container. The original medication container cap from step 961 is replaced on the medication container.

At step 965, the operator manually stores the medication container in the location specified by the O/ESPS local computer (see FIG. 2 II).

At step 970 if the container is to be stored in the refrigerator, an optional log-in/log-out control system and procedure is available to verify if the container was refrigerated satisfactorily (see FIG. 2 II b). This way, if the container is outside of the refrigerated storage area more than a specific number of minutes the O/ESPS local computer will not permit the syringe to be filled from that container, and will alert the Pharmacy Technician to remove and discard that container.

At step 975 if the container is to be stored in a light protected storage area, an optional log-in/log-out control system and procedure is available to verify if the container was stored appropriately (see FIG. 2 II c). This way, if the container is outside of the light protected storage area more than a specific number of minutes the O/ESPS local computer will not permit the syringe to be filled from that container, and will alert the Pharmacy Technician to remove and discard that container.

Figure 3:
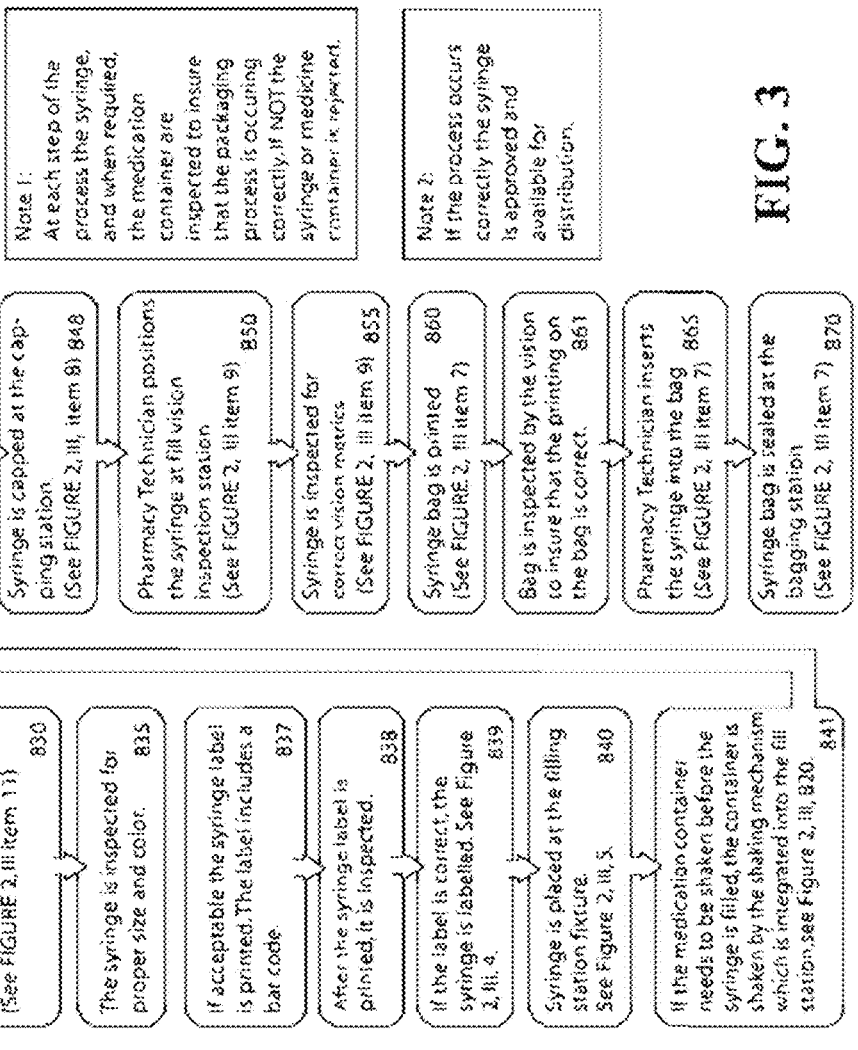
FIG. 3 is a more detailed flowchart of the substeps of the batch fulfillment process 750 of FIG. 1.

Batch Fulfillment Process 750 (FIGS. 1-3)

With reference both to FIGS. 2-3, at step 800 a pharmacist must log into the O/ESPS local computer to use the system.

At step 810, the pharmacist selects the desired O/ESPS operational mode. Currently four modes of operation are envisioned:

1. Patient Specific—Hospital Directed
   a. The Doctor writes the prescription and enters it into the Hospital Host Computer System.
   b. The prescription is reviewed by the Pharmacist. If it is okay, the prescription is sent to the Local O/ESPS Computer where it is batched. Batches will typically be run 2-3 times a day.
   c. The Local O/ESPS Computer first sorts all the batched prescriptions in alphabetical order by name.
   d. The prescriptions are then sorted by size of fill from smallest to largest. The total amount of each medication required for that batch run is totaled. The Local O/ESPS Computer checks to ensure that there is a sufficient amount of product for each medication required to complete the batch.
   e. If a doctor orders, for a single patient, multiple same doses of the same medication to be administered at different times, all doses can be filled together during a single production run or in separate production runs at the discretion of the Pharmacist.
2. STAT (Rush Order)—Hospital Directed
   a. The Doctor writes the prescription and enters it into the Hospital Host Computer System.
   b. The prescription is reviewed by the Pharmacist.
   c. The prescription order indicates that the prescription needs to be administered soon to the patient.
   d. If the O/ESPS System 100 is currently being used, the Pharmacist can decide to either stop all current prescriptions being packaged or wait until completion. Either way, the Local O/ESPS Computer processes the singular rush order.
3. Medication Specific—Pharmacy Directed
   a. This mode allows production-scale filling of a large number of syringes with the same medicine and the same fill volume. Some medication will need to be inventoried in advance of the Doctor's prescription. This mode provides the pharmacist with the opportunity to package certain liquid enteral/oral products such as vitamins and popular standard dose medications on a more cost-effective basis than buying them already pre-packaged.
   b. The Pharmacist will manually enter in a production order for the medication into the Local O/ESPS Computer.
   c. The Pharmacist will specify the medication name, size of fill, the information that will go onto the syringe label, the information that will go onto the bag that the syringe is packaged in, and the amount of syringes that are to be packaged for that production run.
4. Manual—Pharmacy Directed
   a. Not all hospitals have an existing electronic prescription system installed that permits the electronic transmission of the Doctor's prescription to the hospital pharmacy. Consequently, the O/ESPS can be operated on a manual basis whereby the prescriptions are entered into the system under the Pharmacist's supervision.

One skilled in the art should understand that other operational modes include a Patient Priority mode in which all medications/oral prescriptions for a specific patient are processed sequentially before moving on to the next patient. The invention is herein described in the context of Patient Specific—Hospital Directed Mode which is the most typical mode of operation.

At step 811, by way of example. Patient Specific—Hospital Directed is selected and the process is herein described accordingly.

At step 815 an operator (pharmacy technician) logs in.

At step 820 the O/ESPS local computer directs the operator to select the appropriate medicine container from Storage Facility 2 (see FIG. 2 II), and an appropriate syringe from storage bin 3 (FIG. 2 III).

At step 825, the operator retrieves the appropriate medicine container from Storage Facility 2 (see FIG. 2 II) (under system guidance) and inverts and installs it at the syringe filling station 5 (see FIG. 2 III).

At step 826, the barcode on the bottom of the container is scanned to make sure that all medication-related issues have been satisfied (refrigeration, shaking, light-sensitive storage, expiration, etc.).

At step 830, the pharmacy technician places the syringe S on the labeling station cradle (see FIG. 2, ref. 11).

At step 835, the system automatically inspects the syringe for proper size based on a syringe body measurement (described below), to verify that the correct syringe has been selected. Proper color of color-coded syringes is also verified.

At step 837, the operator prints a syringe label at syringe label printer and labeler station 4 indicating in both human and machine readable forms (i.e. text, barcode or RFID tag) the type, concentration, expiration, etc. of the medication it will contain. The label includes a bar code (preferably a 2D barcode though other labels such as RFID may be used). The label is adhered to the syringe barrel.

After printing the label per step 837, at step 838 the label is inspected to ensure that its content is correct.

At step 839, the label is affixed to the syringe S.

At step 840, the operator manually places the syringe at the syringe filling station 5 (FIG. 2).

At step 841 (if required), the shaking mechanism 820 (FIG. 2 III) shakes the medication container before any medication is drawn from it into the syringe.

At step 845, the syringe is filled at the filling station 5. The O/ESPS system automatically primes and fills the syringe with the medicine by insertion and withdrawal of the plunger.

At step 848, the syringe is capped at the semi-automatic capping station 8. The capping station caps the syringe and presents it to the operator.

At step 850, the operator positions the filled syringe S at the vision inspection station 9 (FIG. 2, III) and at step 855 the syringe is inspected for correct vision metrics. These actions are logged.

At step 860 a syringe bag is printed/barcoded at bag printing and sealing station 7 (FIG. 2, III), and at step 861 the system verifies the bag is printed correctly. If so, the operator is permitted to insert the filled/capped syringe S into the barcoded/labeled bag.

At step 865 the pharmacy technician inserts the syringe S into the bag (FIG. 2, III).

At step 870 the syringe bag is sealed at the bag printing/sealing station 7. The packaged syringe can then be distributed to the patient.

As mentioned at Note 1 (FIG. 3), at each step of the above-described process the O/ESPS system employs comprehensive track-and-trace inspection/validation of the syringe and, when required, the medication bulk container, to insure that the packaging process is occurring correctly and to compile an audit trail of the current and past locations (and other information) for each syringe. If all process steps 800-870 occur correctly, the syringe S is approved and made available for distribution to the patient (see FIG. 1, step 770).

If a process step fails then as seen at step 760 of FIG. 1 the syringe or medicine container is rejected (and barred from distribution to the patient).

The core method and possible variations are herein implemented in several detailed embodiments of a system suitable for preparing patient-specific doses of liquid medications into enteral/oral syringes on a just-in-time basis. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated. For example, the syringe S handling can be accomplished in numerous ways, the simplest option being described above in regard to FIGS. 2-3. In this instance, one operator packages one syringe at a time sequentially from syringe selection through bagging that syringe S until each of the syringes S that need to be filled with a specific medication are packaged (see FIG. 2). However, several syringe handling variations are given below.

Alternative Syringe Handling Options

As mentioned above the handling of the syringes S on the packaging line can be accomplished in numerous ways, the simplest option (Option 1) being described above with regard to FIG. 3. However, productivity of the packaging line can be increased using other syringe handling variations. Some of the alternate syringe handling options are as follows:

Option 2—Similar to Option 1 but one operator processes/packages some or all of the syringes S at one time as a group, at each of three grouped stations before proceeding to the next grouped station. As shown in FIG. 22, for Option 2 a first group of stations includes syringe selection from the syringe storage 3 location, inspecting the syringe for size and color, and labeling the syringe. A second group of stations comprises filling and capping the syringe at syringe filling station 5 and capping station 8. A third group of stations comprises inspecting and bagging the syringe at vision inspection station 9 and bagging station 7. All of the syringes S that are to be filled with the same medication would be processed collectively at the first group of stations 3, 4, then all of the syringes would be processed at the second group of stations 5, 8, and then all of the syringes would be processed at the third group of stations 7, 9 until all of the syringes are packaged with the specific medication. Then the next medication would be packaged. To facilitate this grouped approach, FIG. 22 also shows a ten syringe compartment tray which slides along a track to shuttle ten syringes S back and forth to successive grouped stations.

Option 3—Similar to Option 2 but three operators are utilized, one at the first group of stations 3, 4, one at the second group of stations 5, 8, and one at the third group of stations 7, To facilitate this, a carousel conveyor 325 is shown in FIG. 23 with multiple trays 327, each containing 3-5 syringe compartments per tray. The trays 327 rotate around the carousel 325 past three operators positioned one per each group of stations.

Option 4—Similar to Options 1, 2 and 3 but two operators are situated around a lazy Susan (carousel-like) disc 342, as shown in FIG. 24. Operator One selects, labels and inspects empty syringes S for size and color and places them in trays 343 located radially arranged on the disc 342. Additionally Operator One collects the medication bottles and either stages them, or an upper tier 345 of the disc 342 retains them for the second operator.

Operator Two receives the syringes S and medication bottles via the rotating disc 342 and performs the filling and capping at stations 5, 8, respectively, Operator Two may also do the filled syringe inspection at station 9. At this point it may be necessary to opt for an Operator Three to do the filled syringe inspection at station 9. Operator Two or Operator Three may then place the Filled, Capped and Inspected syringe S onto the rotary disc 342 to be indexed back to Operator One for bagging at station 7.

Option 5—Similar to Option 4 however this system utilizes three (3) operators. As seen in FIG. 25, Operator One inspects empty Syringes for size and color, applies a flag label to syringe S and places it on the lazy Susan disc 342 in trays 343. Operator Two places the empty inspected syringe S into the filling station 5 and fills, caps and places them onto the disc 342 for transport to Operator Three. Operator Three inspects the filled syringe for correct dosage. The syringes S are then conveyed back to Operator One for bagging at station 7.

Referring back to FIG. 2, each station of the pharmacy automation system 100 for enteral/oral syringes is described below in more detail.

Medication Container Login & Orientation Station 1

The first station in the process of the present invention is Medication Container Login & Orientation Station 1 (see FIG. 2 I) at which the bulk medicine is prepared for use in the overall system 100. Medication Container Login & Orientation (MCLO) Station 1 is a standalone desk unit that provides a facility for inputting needed information into the O/ESPS database via scanner 95 and data entry terminal 96, apply barcodes as needed via label printer 97, decap bulk containers 104 at optional capping/decapping station 93, refit and/or retrofit them as necessary with a container/syringe interface (as will be described) at capping/decapping station 93, and optionally photograph them using a label photographing station 98. All of the scanner 95, data entry terminal 96, and label printer 97 are commercially available components. MCLO Station 1 is standalone so that it can be positioned as desired. Medicine for enteral/oral syringes is provided in liquid form in a container with a manufacturer-applied safety cap. An object of the present invention is to be able to insert a syringe terminal discharge into the containers to withdraw a proper dose of medicine into the syringe. To be able to do this manufacturers must supply a specialized cap or insert, or the pharmacy technician must replace or supplement the manufacturer-supplied cap with a container/syringe interface.

Referring back to FIG. 2 I, at MCLO Station 1 a number of bins 12 are provided for storing various sizes and configurations of container/syringe interfaces 210, 212, 214, 216 (see FIG. 5) as needed to fit all standard container sizes. As described above in steps 910 through 965 (FIG. 4), O/ESPS system 100 guidance for the manual container 104 selection process and return process (along with the container/syringe interface 210, 212, 214, 216 and syringe S selections) may be "system-guided" as described above. Each container/syringe interface storage compartment 12 (see FIG. 21) may be enclosed by a magnetically-actuable door so that access to each location may be electronically controlled by the local O/ESPS computer, or illuminated by an LED light, or equipped with a light curtain so that the local O/ESPS computer can monitor access to the proper location.

O/ESPS system 100 guidance for the manual container 104 selection process employs a software module that relies on all three of the information components stored in the O/ESPS system database: 1) product information from the manufacturer or other external sources describing the medicines and their containers (size, dose, handling requirements, etc.); 2) prescription-specific information from the hospital identifying the prescription details and patient to receive it; and 3) O/ESPS runtime information such as the amount of medicine previously taken from a given bulk container. The exact container 104 location is provided to the operator via O/ESPS system 100 guidance who retrieves the container from the Storage facility 2. Again the Storage facility 2 may be fitted with magnetic doors, LED lamps or light curtains either to compel the proper selection, draw the operator's attention to it, or provide an alarm in case of a wrong selection.

In operation, and as described above with regard to FIG. 4 (medication container orientation and log-in process steps 961-963), the OEM caps on medication containers 104 are manually removed and replaced with a valved flow restrictor 212 (see FIG. 5). The O/ESPS local computer instructs the operator which of the valved flow restrictor sizes in storage bins 12 (FIG. 2) to select for insertion into the medication container 104 (step 963). The labeler 97 generates a 2D barcode label which includes the location of Storage facility 2 (see FIG. 2 II) that the medication container 104 (see FIG. 2 I) is to be stored at. The operator places the 2D bar code on the bottom of the medicine container, and the 2D barcode is scanned by scanner 95, and optionally photographed using a label photographing station 98. Ail general and container specific information derived by scanning or supplemental data entry at data entry station 96 is recorded in the local O/ESPS computer database, including the storage location of the bulk container 104 in Storage facility 2 and the expiration date of the medication container. The operator then manually stores the container in the Storage facility 2 assigned by the O/ESPS computer. If the container is to be stored in light protected storage 2 II c or refrigerated storage 2 II b the track-and-trace software ensures compliance. Later, when needed to fulfill a batch of enteral/oral syringe prescriptions an operator will select (with system guidance) a container 104 of the desired medicine from the Storage facility 2 with container/syringe interface 210, 212, 214, 216 (see FIG. 5) applied and load it into the filling station 5 where the 2D bar code label on its base is automatically scanned by scanner 121 at the filling station 5. The medicine is verified by the scanning as to proper content, available fluid volume and other attributes before being filled at filling station 5.

A second station in the packaging process according to the present invention is a storage bin 3 (see FIG. 2 III) for storage of empty syringes. The syringe storage 3 preferably incorporates a separate syringe compartment for each size of syringe that the system anticipates needing in the course of a production run. Again, this manual selection process (along with other manual selections) is "system-guided" as defined above in respect to syringe S selection as well. As with medicine container 104 selection, the software module ascertains from the patient-specific information the appropriate dose of medicine to determine the specific syringe S size to retrieve. The location of that syringe S is ascertained from the database, and the exact syringe S location in syringe storage 3 is presented to the operator who retrieves it from the syringe storage 3. Again the syringe storage 3 may be fitted with magnetic doors, LED lamps or light curtains either to compel the proper selection, draw the operator's attention to it, or provide an alarm in case of a wrong selection. In still other embodiments the syringe storage 3 selection may be semi-automated so that the appropriate syringe S is ejected to the operator under control of the local O/ESPS computer. The selection software module calculates the most appropriate syringe S size based on the required prescription information dosage, the known volume of the syringe selections (the following standardized enteral/oral syringe sizes: 0.5 ml, 1 ml, 3 ml, 5 ml, 10 ml 20 ml, 35 ml, 60 ml), identifies the syringe size to accommodate the fill volume of the prescription, and presents the syringe storage 3 location to the operator who retrieves the syringe from the proper magazine (with help of LED indicator, magnetic door, light curtain, ejection mechanism or otherwise).

A third station in the filling and packaging process is the syringe size/color inspection station 11 which verifies that the correct syringe S has been selected. The syringe size/color inspection station 11 is described more fully below with regard to FIG. 15A.

The fourth station is a flag label printer/applicator 4. After determining that the syringe S is the proper size and color, the operator inserts the syringe into syringe label printer/applicator 4. As described above relative to FIG. 3 (step 837), the operator prints a syringe label at syringe label printer 4. The labeler is in communication with the local O/ESPS computer and automatically prints self-adhesive labels bearing information regarding the prescription such as the eventual contents of the syringe (medicine type, concentration, dosage, expiration, scheduled administration, etc.) and its intended recipient (name, room number, etc.) along with a bar code identifying a central record of this information in the O/ESPS database. The label includes a 2D barcode though other labels such as RFID may be used. The label is inspected to verify the accuracy of the printed information before it is attached to the syringe S. The label is supported by hinged arms of the applicator and held by vacuum pressure while the applicator advances to envelope the syringe barrel with the hinged arms coming together to join the label as a flag to the barrel of syringe S. A portion of the label around the barrel must be transparent to permit dosage markings of the syringe to be clearly visible.

A fifth (optional) station is a medication container shake station for automatically shaking the medicine container when necessary. A shaking mechanism 820 integral to the filling station 5 is described below. An alternative, remotely-positioned medication container shake station 6 is described more fully below with regard to FIG. 17.

The sixth station is the syringe filling station 5 for filling the syringes S. The operator positions the empty syringe S (step 840) at the syringe filling station 5. A scanner 121 is resident at the syringe filling station 5 to automatically scan the machine readable label on the bottom of the container 104 to again verify that the selected item is correct. The hand-held scanner at the fill station 5 scans the label attached to the syringe to verify that the appropriate syringe is being used. The medicine container 104 and the syringe S are loaded into the filling station 5 in various ways dependent upon the container/syringe interface that is used. The four container/syringe interfaces and associated procedures for use are discussed below. The system automatically fills the syringe S with the medicine by calibrated withdrawal of the plunger.

The seventh station is a visual inspection station 9 which comprises optical inspection to optically determine if the syringe is filled correctly. On this basis the System 100 accepts or rejects the weighed/inspected syringe.

FIG. 6A is a perspective view of an exemplary vision inspection station 9 in which syringe fill volume is inspected by a CCD imager 330 that optically detects by image analysis if the syringe S plunger is at the correct location, the volume above the plunger and below the syringe tip is filled with product, and also checks for bubbles in the product.

With respect to FIGS. 6A and 6B, the illustrated embodiment of the vision inspection station 9 generally comprises a flat base 92 with vertical syringe-mounting plate 93 at one end, caddy-corner to a vertical camera mounting plate 94. CCD imager 330 is mounted overhead on a camera-mounting bracket 95 extending upward from the camera mounting plate 94. A syringe holder 96 protrudes from the vertical syringe-mounting plate 93 and suspends a syringe by its cap (two yoke fingers under the cap). An optional syringe clamp 99 may be provided opposite the syringe holder 96 for clamping the syringe therein. In its simplest form (shown), syringe clamp 99 is a spring-biased jaw that clamps against holder 96 to secure the syringe. A backlight panel 97 resides directly behind the syringe S (beneath syringe holder 96). Two side-mounted lights 98 provide frontal illumination.

In operation, the vision inspection station 9 establishes and maintains a 'Reference Point" on each syringe which is consistent for all syringes despite size, terminal discharge offset and other variables. In accordance with the invention the reference point is selected to be just below the syringe tip at its intersection with the top of the syringe body. Since the syringe cap covers most of the syringe tip, and that tip volume is never dispensed, the tip can be ignored from any vision reading taken. The filled and capped syringe S is preferably held stationary in the spring-loaded yoke fingers of syringe holder % by its cap, while the backlit camera CCD 330 measures from a reference point to the seal ring of the syringe S plunger. Since the syringes are hung by their caps within a common yoke they will all have the same zero reference point, despite varying sizes. The reading from the 'Reference Point' downward to the seal ring of the plunger comprises a numerical dimension for the specific syringe S size relative to the prescribed dose (the size selected being the next larger size in excess of the dose). Once taken, the O/ESPS computer compares the reading to a predetermined value associated with that syringe size and every increment on the syringe. For example, if a 10 ml dose is prescribed the O/ESPS computer will recommend a 20 ml syringe, in which case the distance from the 'Reference Point' downward to the seal ring of the plunger (when fully inserted) should be 32.75 mm or 1.289". This way, given knowledge of the prescribed dose and the syringe size, the system can accurately determine if the fill dose is correct. Otherwise it will be rejected. The accuracy of fill should be +/−5% of target. In addition, the vision inspection may also include phase-contrast imaging to measure bubbles in the syringe. Phase contrast imaging exploits differences in the refractive index of the contents to differentiate bubbles. Some bubbles are tolerable, but too many are not. The vision inspection may employ phase-contrast imaging as a bubble check. This same process is used to determine if the syringe is "short filled" based on differences in shading. Any voids or bubbles are interpreted as a mixed pixel count in either light or dark depending on the opacity of the medication derived from the O/ESPS computer database. If the syringe volume inspection device 9 determines that the syringe S is filled to the correct volume with an acceptable amount of bubbles and no voids, it will be accepted. An acceptable bubble/void percentage is +/−2%. Optionally, a digital photograph of the filled syringe may be taken and archived for track and trace purposes.

The illustrated embodiment reduces the footprint (size) of the vision inspection system 9 using a mirror to break up focal distance into shorter lengths (here two, though additional mirrors may be used). Specifically, the overhead camera 330 view is reflected off a mirror 333 mounted to wall 94, and is then focused on the syringe S being inspected.

Figure 6C:
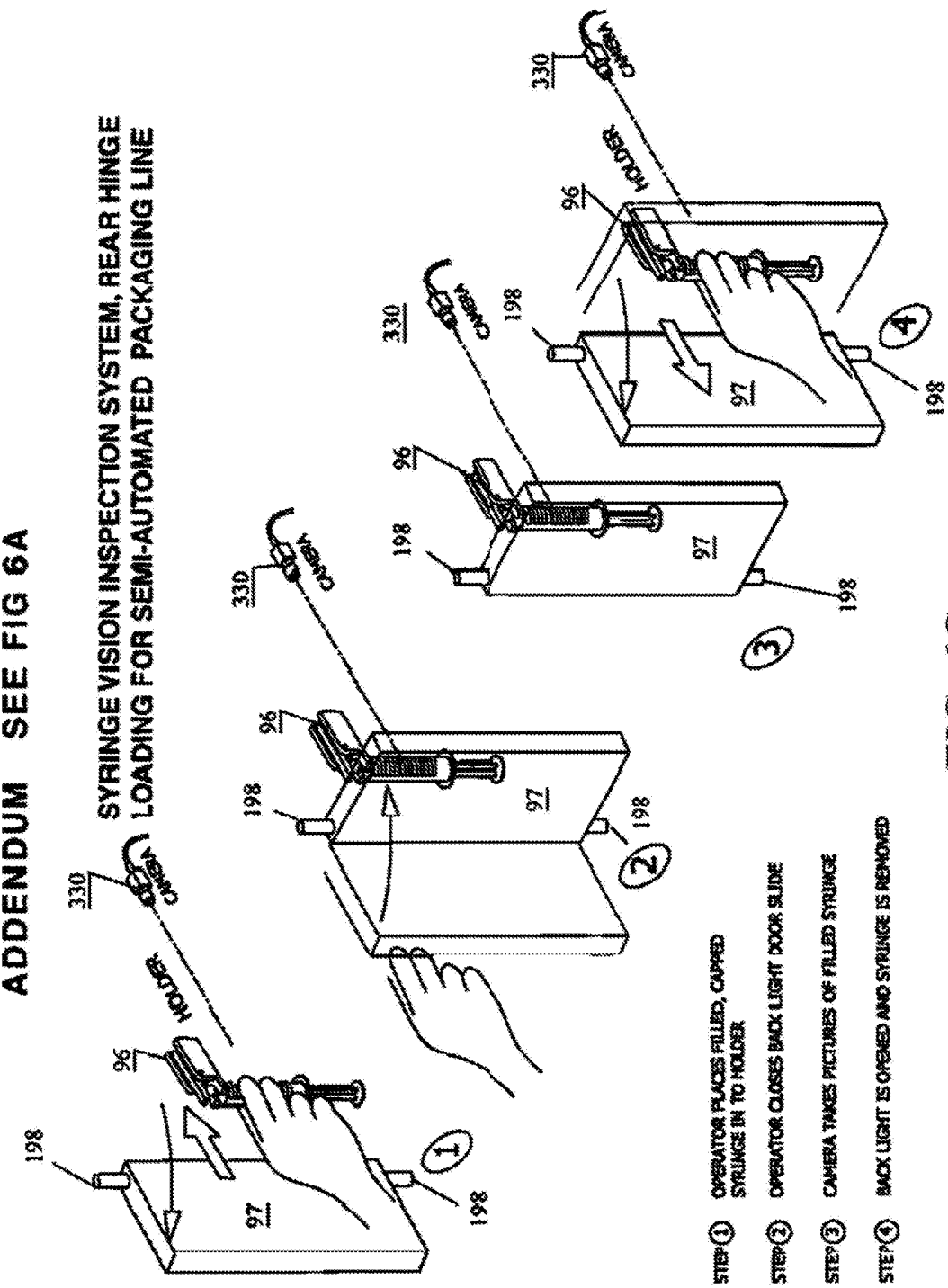
FIG. 6C shows an alternative articulating design for the backlight panel 97.

FIGS. 6C and 6D show two alternative articulating designs for the backlight panel 97 which resides directly behind the syringe S (beneath syringe-holder 96), both perspective sequential views, which facilitate easier loading of the syringe S from behind. In FIG. 6C, the syringe-holder 96 is mounted from a suspension or other non-obtrusive bracket to facilitate rearward access. The backlight panel 97 is mounted behind the syringe-holder 96 on hinges or pivots 198 as shown, to allow the backlight panel 97 to be opened or closed like a door. As shown in the sequence, the operator places the filled, capped syringe S into the syringe-holder 96 at (1), closes the backlight panel 97 at (2), the CCD imager 330 images the syringe S against the backlight panel 97 at (3), and the backlight panel 97 is reopened at (4) and the syringe S removed.

FIG. 6D shows a guillotine-style backlight panel 97 slidably mounted on a pair of spaced-apart vertical rails 195. Backlight panel 97 moves up and/or down within rails 195. As shown in the sequence, the operator places the filled, capped syringe S into the syringe-holder 96 at (1), and closes the backlight panel 97 whereupon the CCD imager 330 images the syringe S against the backlight panel 97 at (2). The backlight panel 97 is then reopened and the syringe S removed.

As still another alternative, the inspection may be accomplished with a check-weigh scale to weigh and/or inspect the filled syringe S to verify the syringe is as labeled. In this case, the O/ESPS software calculates target weight based on the fill size in cc's and multiplies by the specific gravity to derive weight. The specific gravity of each medication is stored in the O/ESPS database along with the percentage +/−% deviation that is acceptable for the actual fill weight. If the actual fill weight is in the target range, it is accepted. If not it is rejected.

The O/ESPS software calculates the target weight based on the fill size in cc's and multiplies by the specific gravity to derive weight. The specific gravity of each medication is stored in the O/ESPS database along with the percentage (+/−%) deviation that is acceptable for the actual fill weight. If the actual fill weight is in the target range, it is accepted. If not, it is rejected.

An eighth station 8 is the semi-automatic syringe capping station described below in detail with regard to FIG. 10. The syringe capping station 8 facilitates accurate placement of syringe caps onto filled syringes S.

The ninth station is a bag printing and sealing station 7 (see FIG. 2 III). The bagging station 7 is a commercially available Hand Load Printer/Bagger for hand load labeling and bagging applications. It is networked to the local O/ESPS computer to automatically print the bag that the syringe S will be packaged in. The bag is printed with information regarding the prescription such as the eventual contents of the syringe (medicine type, concentration, dosage, expiration, scheduled administration, etc.) and its intended recipient (name, room number, etc.) along with a bar code identifying the same content. After printing a bag the system inspects the print on the bag to make sure that it is correct. If so, the operator is permitted to place the filled-capped syringe S in the bag, the system confirms that the syringe was placed in the bag, and the bag is then sealed.

If all the steps are completed correctly the syringes are distributed for administration to the patient.

One skilled in the art will recognize that certain steps may be completed in various alternate sequences to achieve die same result, and features may be modified or eliminated as a matter of design choice.

At initial MCLO Station 1 an operator prepares bulk medicine containers for use at the automated syringe filling station 5. Preparation entails applying one of the above-described container/syringe interfaces. Again, each medicine container is pre-labeled with a unique identifying number, for example, in barcode format adhered to the bottom of the container. Preparation of the container 104 also includes scanning, verification, optional photographing, and recordation of container 104 label information including content information (name, manufacturer, foil volume, concentration, etc.), batch or production information, and expiration information with its assigned container 104 in a medication track and trace database. Various other parameters for each medicine can be associated with each record in the database such as the maximum flow rate at which a certain medicine can be withdrawn from its storage container (i.e. to prevent cavitation/inaccurate fills), the storage temperature (ambient or refrigerated), the required frequency of shaking/agitation of each medicine to keep any particulate matter properly suspended/distributed (e.g. between each syringe fill dispense cycle or only at the start of a series of syringe fill dispense cycles).

Each barcode (or possibly RFID tag or other label) preferably references the following information:
  Batch number
  Expiry date
  Storage instructions
  Product name
  Strength
  Name of the active ingredient(s)
  Dose form
  Warning statements
  FDA number
  Product need to be shaken before use? If so, how often?
  Product need to be refrigerated before use? If so, temp?
  Protection from light
  Volume of original bulk medication container?

The information available from the pharmaceutical manufacturer's barcode on the medication container varies from manufacturer to manufacturer. The operator is prompted to enter any missing data directly into the computer data entry terminal 96 at MCLO Station 1. The information from the pharmaceutical manufacturer's barcode label plus the variable information is stored in the medication container database which is linked to the medication container by the barcode label on the base of the container, which includes the container identifying number assigned to the container 104 in the medication track and trace database. It is also important that each container 104 is marked in both human and machine readable forms (i.e. text, barcode or RFID tag) as to the type and concentration of the medication it contains along with various other information, to enable visual inspection.

The containers/bottles 104 are typically manufacturer-supplied although custom containers/bottles may be used for purposes of the present system. If the storage containers or bottles 104 are provided by the manufacturer, 20 mm, 24 mm, and 28 mm neck diameters are typical. The bulk containers may be provided in a specified, standardized format by the manufacturer, or the medicines may be refilled into standardized containers onsite.

With regard to filling station 5 in FIG. 2, the enteral/oral syringe may be entirely evacuated such that its plunger is advanced all the way into its barrel or the enteral/oral syringe may have a calibrated amount of a gas (such as air) in front of the plunger in the barrel. The syringe plunger may be withdrawn to draw the fluid into the barrel. Where a gas is present in the syringe, the plunger may be first advanced so as to force the gas into the container 104. The plunger is then withdrawn to draw the fluid into the syringe, Introduction of the gas into the container 104 slightly pressurizes the container initially and prevents the development of negative pressure within the container which would inhibit fluid flow. When the syringe is filled to the proper volume it is withdrawn.

Referring back to FIG. 2, the operator returns the prepared medicine container 104 with its container/syringe interface 210, 212, 214, 216 in the medicine Storage Facility 2 where it remains until called for. The system software monitors the contents of the medicine Storage facility 2 in terms of both identity of the prepared medicines available to be dispensed and the quantity of each medicine. The content of the Storage facility 2 is continually updated as the medicine is dispensed and the system is able to predict based on current pending prescription and historical dispensing information when the current available container of any given medication will be empty so as to advise the operator to prepare a replacement quantity of such medicine prior to emptying the existing container. Medicines exceeding their expiry dates are also identified by the system to be discarded by the operator.

After retrieving the syringe from syringe store 3 (see FIG. 2 III) of empty syringes S to be filled as described above, the operator inserts the syringe into a station that includes a syringe color/size inspection device 11 and a syringe label printer/applicator 4.

FIG. 15A is a perspective view of an embodiment of the syringe size/color station 11A which verifies that the correct syringe size (0.5 ml, 1 ml, 3 ml, 5 ml, 10 ml, 20 ml, 35 ml, and 60 ml)) has been selected by the operator. One skilled in the art should understand that syringe size/color inspection station 11A may be placed anywhere but is best placed proximate the filling station 5. The illustrated syringe size/color inspection station 11A essentially comprises a set of automatic electronic calipers connected to the O/ESPS Computer. More specifically, a support surface 1101 is formed with a pair of aligned slots 1103, 1104. A stationary cradle comprises a pair of spaced-apart yokes 1102a, 1102b fixedly mounted on the support surface 1101 on opposite sides of the slots 1103, 1104 for supporting the syringe S in a horizontal position. A pair of articulating caliper fingers 1105 protrude upward through the slots 1103, 1104 to embrace the syringe S on both sides. Caliper fingers 1105 are driven by an underlying caliper drive mechanism connected to the O/ESPS Computer which moves fingers 1105 into contact with the syringe S after the shuttle 5s has deposited the syringe S onto the yokes 1102a, 1102b. The caliper fingers 1105 rise to a height higher than the center of the largest syringe size, and in operation the fingers 1105 close around the body of the syringe S until a force is sensed (indicating contact with the syringe). At this point a measurement of the syringe body is taken (the distance between fingers 1105 is calculated) to verify that the correct syringe S has been selected. Enteral/oral syringes are often color coded in translucent colors for ease of identification. For example, enteral/oral syringes may be a highly visible amber color to distinguish its contents as an orally administered medication. To verify color, a color inspection camera 1107 is also connected to the O/ESPS computer and may be mounted in either of yokes 1102a, 1102b to image the color of the syringe S. A 3-CMOS imager is preferred for this application to capture RGB pixel data, which is compared by O/ESPS Computer to a color lookup table or subjected to another color-matching algorithm to verify the proper syringe color. If size and/or color are correct, labeling and/or further processing of the syringe S will take place.

FIG. 15B is a perspective view of an alternate embodiment of a syringe size/color station 11B which verifies that the correct syringe has been selected. Embodiment 11B comprises a parallel pneumatic gripper 1201 fixedly mounted at a downward incline within a supporting structure here comprising opposing vertical plates 1210, 1212 connected by a cross-bar 1214. There are a variety of commercially-available pneumatic grippers available in parallel, angular, radial and concentric versions, and in this instance a parallel version is used, such as a Rexroth™ GSP precision parallel pneumatic gripper. Opposing syringe gripper jaws 1220 are attached to the existing gripper 1210 arms, each jaw 1220 comprising a downward extension to a horizontally-disposed finger. The opposed horizontal fingers 1220 are formed with inwardly-disposed vertical grooves to provide a proper grip on the syringe barrel, while holding it vertically. A mechanism is provided for measuring syringe size. In one embodiment, this is a linear variable differential transformer (LVDT) 1225 (also called a differential transformer) mounted m plate 1210, and its sensing piston is threaded into a collar 1227 secured to the opposing jaw 1220 for measuring linear displacement (position). The LVDT 1225 is connected to the O/ESPS Computer and measures the distance traveled by the jaw 1220 as it closes around a syringe S. The LVDT 1225 takes monitors an input voltage differential from a starting position to a final position after gripping the syringe S, and calculates syringe size from distance traveled by the jaw 1220. In another embodiment, an alternate or redundant mechanism for measuring syringe size may be provided on a labeling fixture 402 for interfacing with the label wiper L of a conventional pressure sensitive label applicator described below, the labeling fixture 402 shown below in FIG. 35. As above, to verify color a color inspection camera 1107 may be mounted in either of plates 1210, 1212 to image the color of the syringe S and thereby ensure that size and color are correct, such that labeling and/or further processing of the syringe S may take place. One skilled in the art should understand that the syringe measurement system 11B may be integrated as part of the syringe filling station 5 (see FIG. 2 III) rather than as a standalone station as shown in FIG. 15B, thereby consolidating the size/color inspection function with the filling operation.

The labeler 4 is in communication with the central controller and prints self-adhesive labels bearing information regarding the prescription such as the eventual contents of the syringe (medicine, dosage, scheduled administration, etc.) and its intended recipient (name, room number, etc.) along with a bar code identifying a central record of this information. As stated above the different syringes have different exterior dimensions, and the labeler 4 must accommodate the different sizes. Commercially available pressure sensitive label applicators tend to use a label wiper that serves more or less as an anvil. A continuous sheet of pressure sensitive labels is incrementally printed extracted such that the next label to be applied faces the label wiper/anvil (adhesive outward). The article to be labeled is then pressed against the label and label wiper to secure the label. Existing label wipers tend to be fixed or limited to single-axis motion, and so for cylindrical syringes of different syringe sizes the syringe itself must be articulated and indexed in from of the labeler 4. As the syringe labeler 4 will handle different syringe sizes on demand (depending on the size of syringe the prescription requires), it is important to automate the alignment of the syringe to the label wiper. Otherwise, the operator would need to do this each time the size of the syringe changed which would add a considerable amount of time to label the syringe. This is herein accomplished with a servo-driven syringe labeling fixture 402 for holding and positioning the syringes S during 'flag labeling'. The syringe labeling fixture 402 is present at tire fourth station 4 (flag label printer/applicator 4), and may be used with any suitable flag printer (semi-automatic or automatic) such as, for example, the model 276S available from Labeling Systems of Oakland, N.J., which is pre-configured for labeling syringes, tubing or other cylindrical products.

An aspect of the present invention is an improved syringe labeler station 4 inclusive of a labeling fixture 402 for interfacing with the label wiper L of a conventional pressure sensitive label applicator, and dual syringe label inspection scanners including a first scanner head for scanning labels for accuracy just after printing and a second scanning head for scanning labels for accuracy just prior to the labels being applied by the labeling fixture 402.

FIG. 28 is a side perspective view of the labeling fixture 402. Labeling fixture 402 comprises an open-faced open-bottom pentagonal housing 422 from which two overhand grippers 451, 452 contact a syringes S from above, and two underhand grippers 453, 454 contact the syringes S from below. Overhand grippers 451, 452 and opposed underhand grippers 453, 454 articulate vertically as described below, grip the syringe S, and position syringe S at the proper vertical position in front of the label wiper L. As described below the labeling fixture 402 also translates back and forth to position syringe S at the proper horizontal position in front of the label wiper L. This ability accommodates variations in syringe size. For convenience, the labeling fixture 402 housing 422 is mounted atop a flat rectangular sub-plate 432, and the subplate 432 removably mounts to a flat rectangular base plate 434 as seen in FIG. 29 by captive panel screws or the like, base plate 434 likewise being a larger rectangle with a cutout 436 sized to accommodate the labeling fixture 402. FIG. 29 is a side perspective view of the labeling fixture 402 removed from subplate 432. This mourning configuration provides easy removal of the labeling fixture 402 and access to any of the internal or underlying components within housing 422.

As indicated above the labeling station 4 includes dual syringe label inspection scanners. These include a first scanner head 444 proximate the label prim head as seen in FIG. 29 for scanning labels for accuracy just after printing. In addition, a second scanner head 442 is positioned proximate the wiper for scanning labels for accuracy just prior to the labels being applied by the labeling fixture 402. Both scanners 442, 444 are helpful for redundant verification. The first scanner head 444 proximate the label print head as seen in FIG. 29 will scan the label prior to application for label print accuracy, while the second post-wipe scanner 442 scans the label in reverse after application to ensure label adhesion accuracy after printing.

FIG. 30 is a perspective view of the syringe labeling fixture 402 holding a small-size syringe S, while FIG. 31 is a perspective view of the syringe labeling fixture 402 holding a large-size syringe S. The syringe labeling fixture 402 generally comprises a flat base 410 slidably mounted atop a pair of parallel tracks 471, 472 oriented front-to-back, and a servo-drive mechanism 460 recessed beneath the base 410 for controlled-linear front-to-back actuation of the base 410. Flat base 410 supports two upstanding side brackets 421, 422. Two vertically-oriented tandem tracks 431, 432 are attached to the side brackets 421, 422, and four sled assemblies 441, 442, 443, 444 ride within the tandem tracks. Each sled assembly 441-444 supports one respective gripper 451-454 for controlled vertical motion. Two of the grippers 451, 452 are overhand grippers formed with protruding fingers configured to contact the syringes S from above, while two of the grippers 453, 454 are underhand grippers formed with opposed protruding fingers configured to contact the syringes S from below. The sled assemblies are independently pneumatically driven up or down along tandem tracks 431-434 (two of four tracks 431, 432 being shown). The pneumatic actuator assembly 481-484 (two of the four 483, 484 being show) controllably drives the four sled assemblies 441, 442, 443, 444 up or down, the overhand grippers 451, 452 lowering to contact the syringes S from above, and the underhand grippers 453, 454 raising to contact the syringes S from below. Once secure, this configuration gives each syringe S held within the grippers 451-454 two axes of controlled motion up/down and in/out. Once the syringe S (of any size) is secure between the grippers 451-454, the grippers 451-454 may all be raised or lowered in unison.

FIG. 33 is a composite cross-section illustrating how each pair of the four sled assemblies 441, 442 and 443, 444 may be connected by a rack-and-pinion mechanism to compel synchronous movement. Toothed racks 487 may be attached to each of the four sled assemblies 441, 442, 443, 444 by pins 489, and the facing racks 487 of each pair of the four sled assemblies 441,442 and 443,444 counter-driven by a pinion gear 490 rotatably mounted there between. As air pressure is introduced to pneumatic actuator assemblies 481-484 (two of the four 483, 484 being shown) the two opposing sled assemblies 443, 444 up or down, the pinion gear 490 constrains the opposed racks 487 to move the same amount, so that the overhand grippers 451, 452 lower and the underhand grippers 453, 454 raise uniformly. This self-centering mechanism synchronizes each set of grippers 451, 452 and grippers 453, 454 to always be the same distance from center. The self-centering mechanism also deals with any syringe S taper due to the independent action of each gripper set. The parallel grippers 451-454 hold the syringe S to a pre-set pressure and seek/maintain a grip on the syringe S relative to the pre-set pressure. This self-centering feature assures that the ends of the label are applied so that they match each other and that there is no over-hang, causing a possibility of the adhesive, sticking to any package material or airy item it comes in contact with. Once the syringe S (of any size) is secure between the grippers 451-454, the grippers 451-454 may all be raised or lowered in unison to vertically position the syringe S at any height relative to the flag labeler print head and despite the syringe S size. This allows die syringe labeling fixture 402 to present each syringe S parallel to the label and at the proper tangent depending on syringe S size. For example, if a 60 ml syringe S resides in the grippers 451-454 the edge closest, to the label applicator will be tangent to the vertically-fed label. Conversely, if a 0.5 ml syringe S is selected the syringe labeling fixture 402 will self-center the syringe S and slide this smaller diameter syringe toward the label along tracks 471, 472 and stop when its tangency point is next to the label. Since the syringe S diameters are finite, it becomes possible to calculate how much x, y movement of the syringe labeling fixture 402 is needed to present all the syringes to the labels at the exact tangency point.

Having explained the benefits of proper labeling irrespective of syringe-size, it may be advantageous to measure the syringe body diameter. This may, for example, serve as a check on the technician's syringe selection. This measurement should take place prior to the label application so that if the syringe size is incorrect no wasted label will take place. When implemented, the syringe size validation check becomes part of the comprehensive track-and-trace feature of the invention, the size check record being digitally recorded along with other verifications indicating that the correct syringe size was labeled.

As indicated above, syringe size is validated at syringe size/color inspection station 11B by an LVDT 1225 mounted in plate 1210. Alternately, syringe size can be validated at the syringe labeling fixture 402.

For example, syringe size can be validated with a linear variable differential transformer (LVDT) sensor 500 that is integrated into the syringe labeling fixture 402. More specifically, the syringe size sensor 500 is mounted to one of the lower grippers 453, 454.

FIG. 34 is a perspective drawing showing the syringe size sensor 500 mounted to lower gripper 453. As described above, one 421 of the two upstanding side brackets 421, 422 supports vertically-oriented tandem track 431, and sled assemblies 441, 442 ride within the tandem track 431. Lower gripper 453 is attached directly to the lower sled assembly 441. The lower sled assembly 441 is equipped with a downwardly-protruding arm 503. A lever 507 is pivotally attached on one side to fulcrum 505 located on gripper 453. The lever 507 extends to and is pivotally attached to the piston of an LVDT 509. The base of LVDT 509 is pivotally attached by yoke 511 to the base 410. The arm 503 of the lower sled assembly 441 protrudes downwardly and is pivotally attached midway along lever 507 to raise/lower it about fulcrum 505, thereby amplifying and translating the displacement of sled assembly 441 into movement of the LVDT 509 piston. The separation of the grippers 451, 453 measures syringe S size, and output of the LVDT 509 indicates syringe S size, and the separation of the grippers 451, 453 actuates the LVDT 509 to yield an accurate electrical reading of syringe size. The lever 507 is mechanically fitted to amplify the movement so that a little movement of the lower gripper 453 gives out a greater movement of the lever 507 and LVDT 509. The entire assembly conveniently fits below die mounting plate 410 out of the way, accurately measures all syringe S body diameters even ones that are only a few thousands of an inch different (as would a caliper). The gripping as well as the syringe body diameter measurement takes place prior to the label application, and if the syringe size is incorrect, no wasted label is applied. The size record is appended to the complete track-and-trace log.

As an alternate to LVDT sensor 500, syringe size can be validated by the servo-drive mechanism 460 integrated into the syringe labeling fixture 402. More specifically, the syringe size can be measured and validated by a rotary encoder 529 shown and described below with reference to FIG. 35.

The servo-drive mechanism 460 and pneumatic actuator assembly 481-484 are in communication with the local O/ESPS computer as is the flag label printer and LVDT 509, and given semi-automated placement of the syringes S within the open grippers 451-454 the station 4 automatically prints self-adhesive labels bearing information regarding the prescription such as the eventual contents of the syringe (medicine type, concentration, dosage, expiration, scheduled administration, etc.) and its intended recipient (name, room number, etc.) along with a bar code identifying a central record of this information in the O/ESPS database. The label includes a 2D barcode though other labels such as RFID may be used. Once skilled in the art will readily understand that the syringe labeling fixture 401 may also be used for placing flag labels on wire (rigid or flexible), rod, cable, power cords, tubing or on any linear surface or diameter. No change parts are required since the grippers 451-454 are pneumatic and seek their own grip on the syringes S or other products. This is also true if the products are tapered because the grippers 451-454 will close until they feel resistance, then hold the product until the label is applied. Optionally, a sensor can be employed to assist in seeking the correct tangency point relative to the label. This sensor may be any suitable movement or contact sensor element such as a Hall-effect or IR-beam sensor.

FIG. 35 is a perspective drawing showing an alternative embodiment of a syringe size sensor 520. As described above, the lower sled assembly 441 is equipped with a downwardly-protruding arm 503. A link 522 is pivotally connected to the distal end of arm 503. The other end of link 522 engages a drive pulley 523 at an offset location, such that vertical movement of lower gripper 453 on lower sled assembly 441 reciprocates drive pulley 523. Drive pulley 523 is in turn connected by belt 527 to a driven pulley 528 mounted as shown to or near bracket 421. The driven pulley 528 turns a rotary encoder 529 that is electrically connected to the local O/ESPS computer. If desired, an optional idler/tensioner pulley 526 can be mounted to impart a pre-bias against belt 527 as needed. The belt 527/pulley 528 arrangement again translates displacement of sled assembly 441 into rotary movement of the encoder 529. The separation of the grippers 451, 453 measures syringe S size, and as such output of the rotary encoder 529 yields an accurate electrical reading of syringe size. The entire assembly 520 conveniently fits below the mounting plate 410 out of the way, accurately measures all syringe S body diameters to a few thousands of an inch prior to the label application, and if the syringe size is incorrect, no wasted label is applied. The size record is appended to the complete track-and-trace log One skilled in the art will readily understand that the individual stations described above, inclusive of the syringe labeler 4 and syringe size sensors 500, 520, may be provided and used independently or as part of an integrated system. Also, it should be apparent that if the syringe size sensors 500, 520 are used the syringe size/color inspection station 11 of FIG. 15 may not be necessary.

FIGS. 32(A) and 32(B) are composite views of the syringe labeling fixture 402 illustrating how it interfaces with the label wiper L of the pressure sensitive label applicator. FIG. 32(A) shows the syringe labeling fixture 402 holding a large-size syringe S, while FIG. 32(B) is a perspective view of the syringe labeling fixture 402 holding a smaller-size syringe S. In both cases a continuous web of pressure sensitive labels is extracted in advance of the label wiper L. Depending on the known size of the cylindrical syringe S, the syringe labeling fixture 402 is articulated as described above to bring the syringe S within a fixed distance of the label wiper L regardless of syringe size. The indexing of syringe S is adjustable along two-axes as shown in FIG. 32(B) to accommodate a smaller-size syringe S, and can be adjusted for any variation in between.

Once indexed, either the label wiper L can be pressed to the syringe S, or vice versa, to press and adhere the next incremental label to the syringe S.

This way, regardless of syringe S size, each label is printed, scanned (inspected) and, if approved, securely and uniformly applied to the syringe using the above-described syringe labeling fixture 402.

FIG. 7A is an enlarged perspective view of a semi-automated syringe fill station 5 for filling the syringes S. Prior to inserting the syringe into the syringe filling station 5, the operator will have selected from the Storage facility 2 the appropriate, prepared container 104 with a valved flow restrictor (see FIG. 5) from which to dispense the proper medicine into the syringe S. The operator first inverts and then inserts the prepared container 104 into yoke 82C (see FIG. 7C III). The syringe S is then manually loaded by the operator into the syringe filling station 5, preferably with the plunger partially withdrawn from the barrel. The syringe S/plunger combination is inserted into the medicine container. Several support fixture/yoke variations are envisioned.

Figure 8:
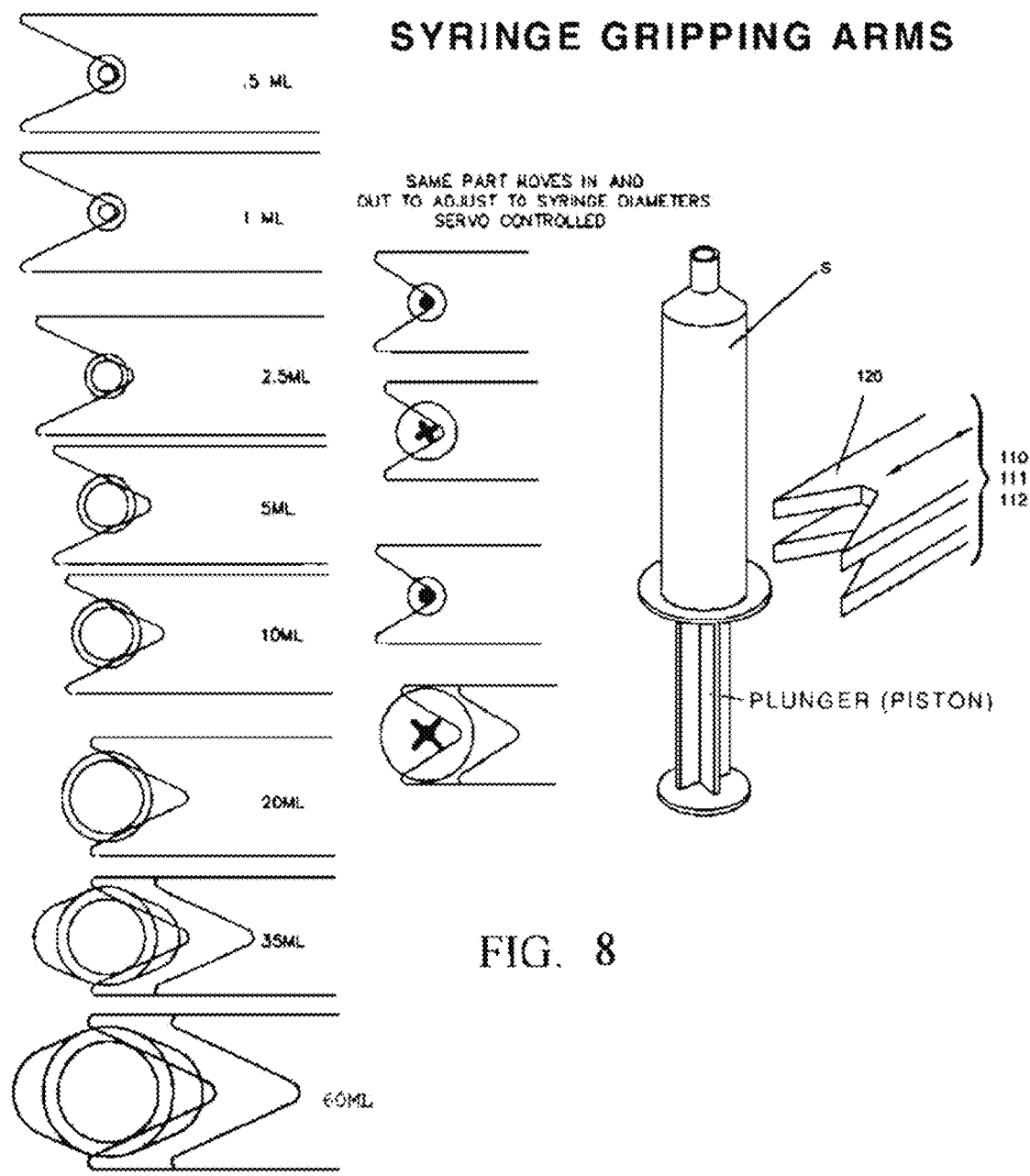
FIG. 8 is a composite view of the syringe gripping arms 110, 111 and 112 terminating in a pair of fork shaped fingers 120 that form a horizontally oriented "V" shaped opening.

As seen in FIG. 8, each arm terminates in a pair of fork shaped fingers 120 that form a horizontally oriented "V" shaped opening to engage the syringe barrel and plunger cross sections regardless of the size of these elements. Each arm is independently servo controlled and slideable in both an up-down direction and a horizontal forward-back direction to facilitate engagement with and operation of the syringe and plunger. The upper and middle arms 110, 111 grip above and below the syringe barrel flange, while the lower arm 112 grips the plunger flange. The local O/ESPS computer calculates the distance to move the lower arm 112, plunger lifting and 128 and plunger flange to extract the appropriate dose of medicine based on the prescribed dose volume V and known radius or diameter of the syringe S size retrieved. The linear travel distance H equals $V/\pi r^2$, where the radius r is stored in the database. The linear travel distance H constitutes the distance that the lower arm 112 needs to travel to pull the correct amount of medicine into the syringe S. The local O/ESPS computer then controls the movement of fill arms 110, 111, 112 and plunger lifting arm 128 in accordance with the calculated distance H, and may also account for other variables such as medicine viscosity, volume of fill, etc. to optimize either the linear travel distance H or the filling force exerted or filling time taken along that distance.

Figure 9:
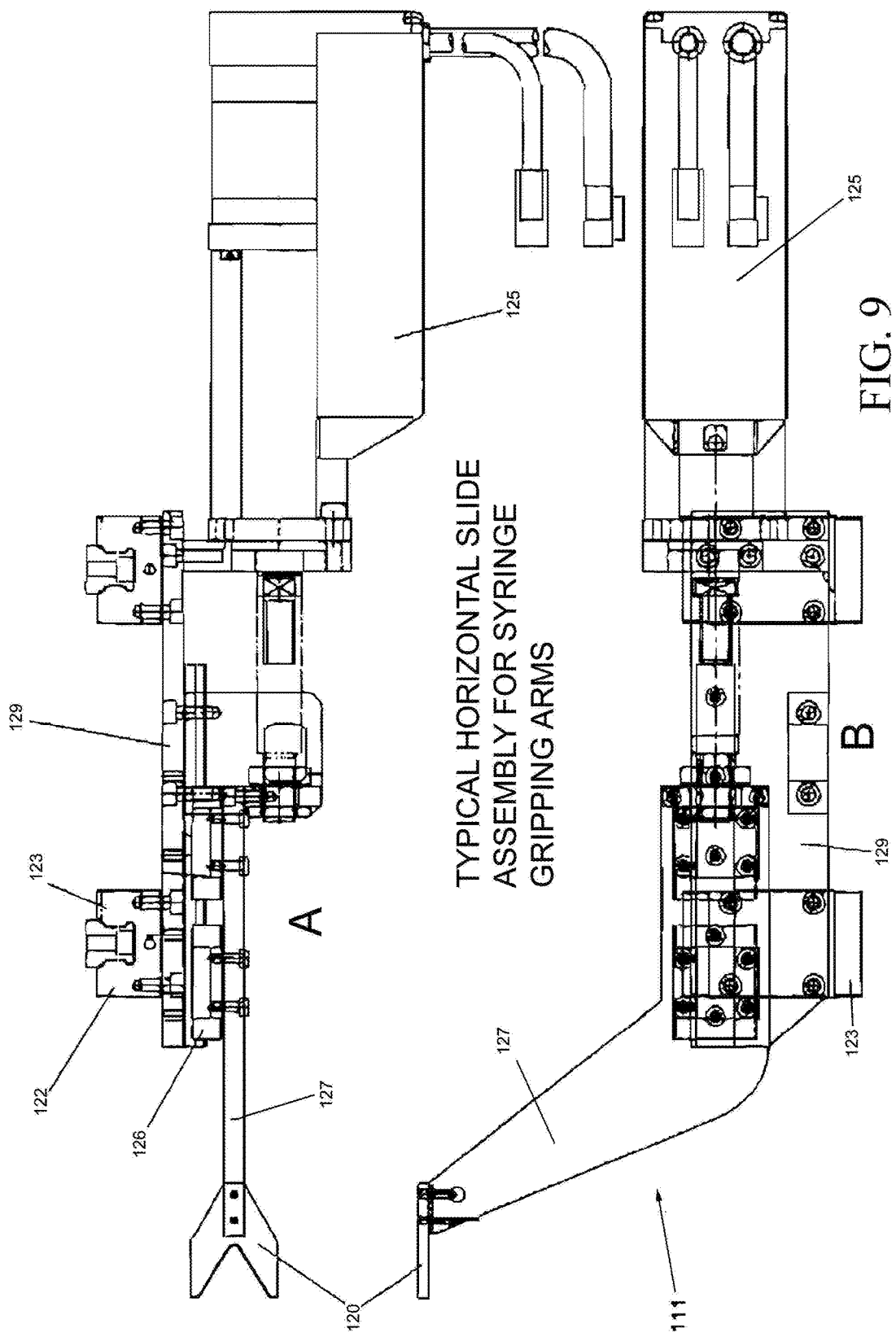
FIG. 9A is a top view that illustrates an embodiment of the syringe gripping arms 111 and its drive mechanism.
FIG. 9B is a side view of the syringe gripping arms 111 and its drive mechanism as in FIG. 9A.

With reference to FIG. 9, a preferred embodiment of the present invention provides the upper, middle and lower arms 110, 111 and 112, respectively, in a single stacked configuration each having a horizontally fixed base member 129 riding on a pair of ball slides 122 on a set of guide rails 123 vertically oriented with the housing 895 (of FIG. 7A). Vertical movement of each base member 129 on the guide rails 123 is controlled by a linear servo 124 situated below and extending into the housing 895. Each arm 110, 111, 112 is also provided with a horizontal reaching element 127 slideably mounted horizontally to each base member 129 so as to ride up or down the guide rails 123 with the base member 129 while being extendable or retractable in the horizontal to engage the syringe S. Horizontal extension and retraction of the reaching members 127 is controlled by a horizontally oriented linear servo 125 fixedly mounted to each base member 129 and engaged to the proximate reaching element 127, each which is itself mounted via a horizontally oriented ball slide assembly 126 affixed to the base member 129. The forked fingers 120 are horizontally disposed at the distal ends of the reaching elements 127. In this way the horizontal and vertical motion of each and 110, 111, 112 is individually controllable in two dimensions.

Referring back to FIG. 7A, in addition to the upper, middle and lower arms 110, 111, 112, a plunger lifting arm 128 extends upward from below to depress the plunger of the syringe S into the barrel as will be described. The plunger lifting arm 128 is controlled by a linear servo and is vertically oriented. In certain embodiments the lower arm 112 may serve both the plunger pull-down (withdraw) and plunger lift (depress) operations.

In an alternate embodiment, as shown in FIGS. 26 and 27, instead of a standard "V" shaped opening, each syringe gripping arm 110, 111 and 112 terminates with a pair of curvilinear fork-shaped fingers, the fingers still being horizontally-oriented, wherein the gap between the fingers forms an overall curved shape along the horizontal plane of the gripping arms 110, 111 and 112 and lessens towards its closed end. Optionally, in accordance with this embodiment, arms 110, 111 and 112 may be mounted on a horizontal base member of the filling station by vertical rotatable mounting elements and attached to servo motors mounted underneath the filling station base that control the motion of the arms 110, 111, 112 and additionally plunger lifting arm 128 as will be described. In this embodiment, the interface between the vertical rotating mounting elements for arms 110, 111, 112 and 128 and the base plate of the filling station is sealed to prevent any liquids or other materials spilled during the filling process or Otherwise from leaking into the interior of the filling station. The servo motors thus control vertical position and axial rotation of the vertical mounting elements and therefore the arms 110, 111, 112 and 128 mounted thereon, with plunger lifting arm requiring only the capacity to raise and lower vertically, and not to rotate. Thus, as vertical mounting elements and arms 110, 111 and 112 rotate, they close on the various portions of syringe S corresponding to their vertical orientation. Arms 110, 111 and 112 may rotate as far as possible to grasp syringe S until the curvilinear gap between the fingers matches the width of the portion of syringe S upon which it closes; thus, arms 110, 111 and 112 will rotate under control of the servo motors until syringe S is snugly positioned within the gap between the fingers. In addition, upper and middle arms 110 and 111 may rest on the same vertical mounting element spaced vertically from one another, with a clamping cylinder incorporated therebetween to control their relative vertical orientation. Clamping cylinder may pull upper arm 110 down on top of middle arm 111 to sandwich the syringe hilt or flange between them as described. Advantageously, the use of a low cost clamping cylinder eliminates a more costly servo motor to independently operate arm 110 and/or 111. In all other respects, arms 110, 111, 112 and 128 may perform the same functions as described herein.

Prior to filling, the scanner 121 at the syringe filling station 5 reads the machine readable label on the bottom surface of the container 104 to again verify that the selected container contains the correct medicine.

Once verified to be the correct, the upper arm 110 lowers to contact the upper surface of the syringe S finger flange, and the middle arm 111 raises to contact the lower surface of the syringe S finger flange. Initially, plunger lifting arm 128 pushes the syringe piston all the way up and the lower arm 112 lowers to clamp the syringe piston downward against the plunger lifting arm 128. Priming of the syringe S takes place as lower arm 112 and plunger lifting arm 128 move up and down in concert with each other to perform the syringe priming sequence. After priming is complete and with the syringe piston fully retracted, the syringe can be filled.

During fill operations the upper, middle and lower arms 110, 111 and 112 are initially in a horizontally retracted state. The lower arm 112 engages the plunger above the plunger flange in a similar manner while the lift arm 128 extends upward to engage the distal end of the plunger. The lower and lift arms 112, 128 are brought together to engage trap the plunger flange between them, and the syringe S is entirely evacuated by fully depressing the plunger within the barrel. If the syringe S is entirely evacuated (i.e. the plunger is fully depressed within the barrel), the lower arm 112 is initially dropped, withdrawing the plunger from the barrel and drawing the medicine into the syringe. As noted, in certain embodiments the syringe may have a predetermined amount of air in the barrel to pre-pressurize the container 104. In such a situation the position of the plunger (and hence the volume of air in the barrel to be injected into the container) is determined by the system based on known parameters of the medicine, the container volume and its current fill level, and the plunger is positioned accordingly prior to insertion into the container/syringe interlace by relative movement of the upper, middle, lower and lifting arms 110, 111, 112 and 128. Upon insertion of the tip in the container/syringe interface the plunger is first fully depressed by the lift arm 128 to pressurize the container and subsequently withdrawn by the lower arm 112 at a predetermined rate to fill the syringe S with desired amount of medicine without cavitation.

When the syringe is filled to the desired level, the arms 110, 111, 112 and 128 are lowered in unison and the syringe S is withdrawn from the container/syringe interface 210, 212, 214, 216 and where an elastomeric insert 225 is present it returns to it closed/sealed position. If desired, the syringe plunger may be further withdrawn from the barrel slightly by relative movement of the lower arm 112 as the terminal discharge is withdrawn to draw in any medicine left in the elastomeric insert 225 so as to avoid drippage.

FIG. 16A illustrates an integral shaker mechanism 820 in which a single-speed motor 823 operates through an electronic clutch 827 to rotate cam wheel 824. An eccentric pin 829 protruding from cam wheel 824 slidably engages a slotted block 830 as shown, and block 830 directly engages the upper end of the plate 821. When the motor 823 is activated it reciprocates plate 821, again shaking it and mixing the contents of medicine container 104 held therein.

FIG. 16B is a composite operational diagram illustrating the operation of the integral shaking mechanism 820 of FIG. 16A external of the syringe filling station 5. The plate 821 which supports the medicine container platform, syringe yoke is mounted on vertical slides 831. A slotted driven block 832 mounted on the plate 821 is engaged by eccentric pin 829. As the pin 829 rotates within the slot of block 832 the block 832 oscillates tip and down. A single position clutch is mounted to the motor so that the slotted driven block as well as the entire platform stops at the same downward position all the time. The insets at top illustrate eccentric pin 829 engaging slotted driven plate 832 at top dead center (left), 90 degrees rotation, and bottom dead center.

FIG. 17 is a perspective view of an alternative remote medication container shake station 6 (i.e. not an integral part of the filling station 5 as seen in FIG. 2) for shaking the medicine container when required. The shake station 6 comprises a motor 62 with an offset trough 64 coupled to the rotary shaft 63. The trough 64 is an elongate arched platform for seating and centering medicine containers of various sizes. An upright post 65 abuts the base of the medicine container and self-centers it, allowing tightening of restraining straps 66. The straps 66 secure the medicine container along an oblique offset axis relative to that of the shaft 63. This particular configuration makes loading of the medicine container on the trough 64 very easy as seen in FIG. 17. When the motor 62 is activated the oblique rotation of the medicine container causes a centrifugal force that keeps the container against the stop post 64. Constrained by the bands 66 and post 65 the medicine container is effectively and efficiently shaken.

Figure 10:
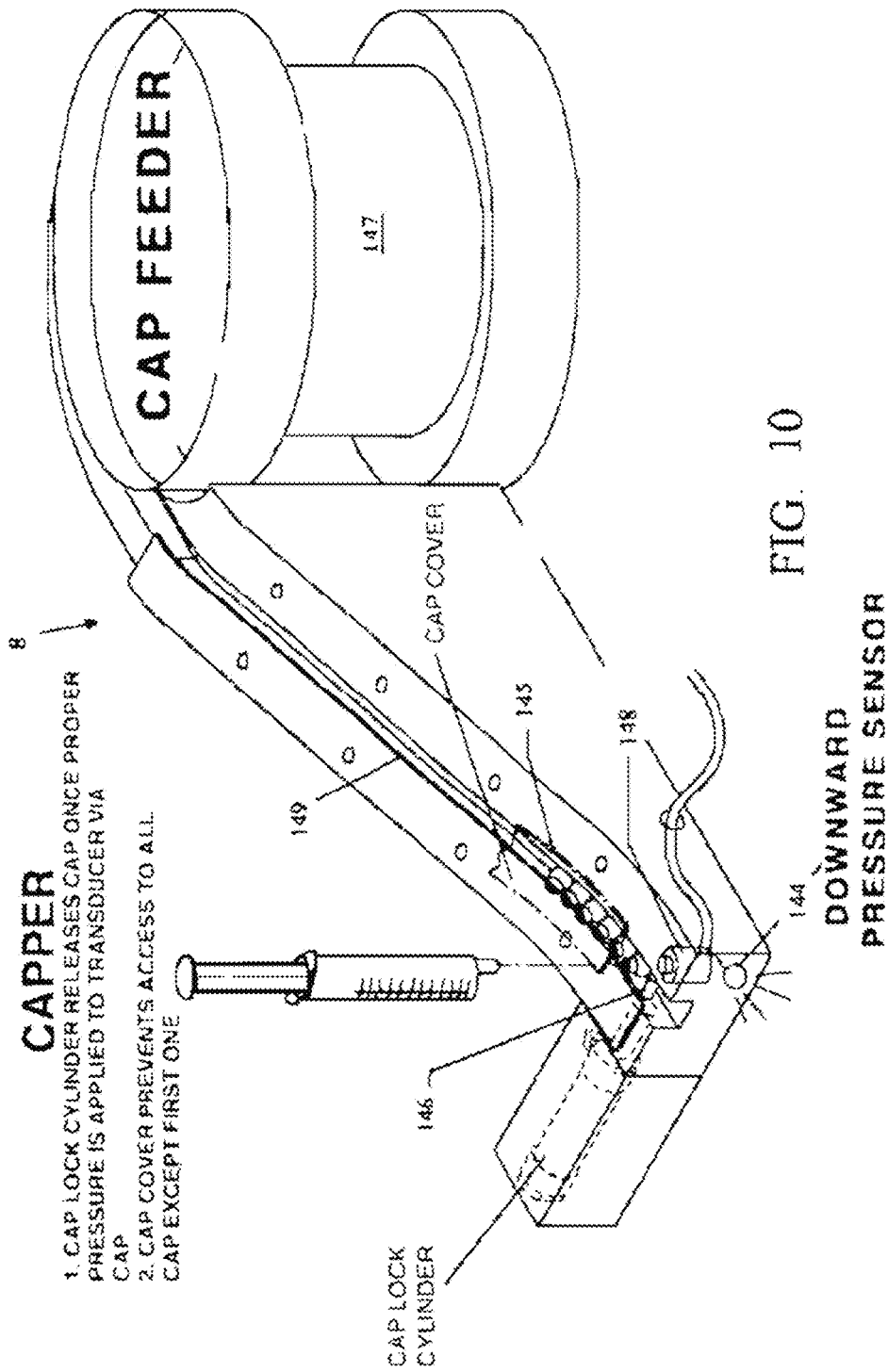
FIG. 10 is an enlarged perspective view of the semi-automated capping station 8.

The (optional) semi-automated capping station 8 (see FIG. 2) facilitates syringe cap placement on the open tip of the filled syringe S, fed from an inclined capping chute 149 (see FIG. 10). Referring back, FIG. 10 is an enlarged perspective view of the semi-automated capping station 8 with feeder bowl 147 and inclined capping chute 149. Feeder bowl 147 may be a centrifugal or vibratory bowl feeder as known in the art, sized for sorting and feeding syringe S caps single-file down inclined chute 149. A transparent plastic chute cover 145 may be provided overtop chute 149 to prevent access to all but the leading syringe S cap. It is rather common for pharmacy technicians to improperly cap filled syringes prior to administration, and this leads to leaking, contamination and other problems. A mechanism is herein provided to prevent this. When die leading syringe caps reach the bottom of chute 149 they come to bear against a cylinder rod 146 in a position directly overhead an electronic pressure transducer 148. Pressure transducer 148 is in communication with the O/ESPS central controller and registers the pressure of the syringe S terminal discharge pressing against transducer 148. A threshold pressure indicator LED 144 is mounted proximate transducer 148. To cap a syringe S the operator merely presses it down onto the leading cap until an acceptable threshold pressure is attained, and this is signaled by an LED indicator 144. At this point the cylinder rod 146 retracts allowing the operator to pull the capped syringe S out and free. The O/ESPS central controller preferably logs this in its track and trace database to provide an audit trail. This mechanism avoids any issues with improperly capped syringes.

During batch operation a series of syringes S to be filled with the same medicine may be queued and loaded in sequence by the operator for filling. When no more syringes are to be filled with the particular medicine, the local container 104 is returned to the medicine Storage facility 2 by the operator, who may retrieve another medicine and replace it in the syringe filling station 5 for the next medicine to be dispensed.

Referring back to FIG. 2, after retrieval from the syringe filling station 5 the operator places the syringe on inspection system 9 to cross check the weight and/or volume of the filled syringe against the expected weight/volume. The tare weight check is based on the known weight of the empty syringe and the volume of the prescribed medicine. The vision inspection entails an optical inspection (described above) based on the location of the syringe S plunger, the volume above the plunger and below the syringe tip, and bubble check. If the inspection station 9 determines that the syringe is filled to the correct volume and/or weight with an acceptable amount of bubbles, it will be accepted. Otherwise it will be rejected.

The labeled, filled and capped syringe is then bagged at bagger 7 for distribution to the patient, the bag itself being labeled in a similar manner as to the syringe. Bagger 7 may be any suitable commercially-available bagger with a network-capable bag printer, bag storage/dispenser, and heat seal assembly. A variety of automatic "tabletop bagger/printers" are available for this purpose.

Figure 11:
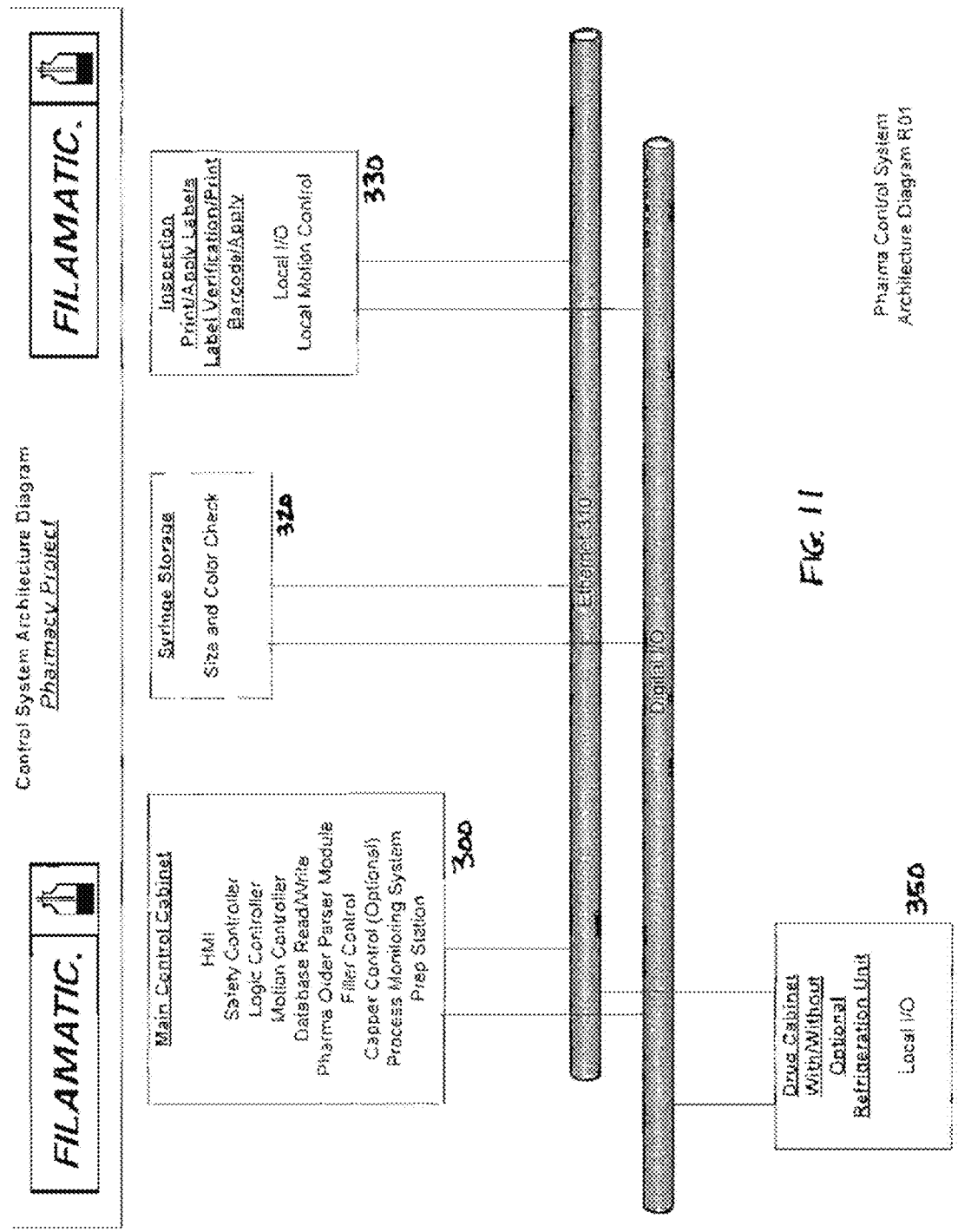
FIGS. 11 and 12 illustrate an exemplary control system architecture for the system 100 of FIGS. 2-10.
Figure 12:
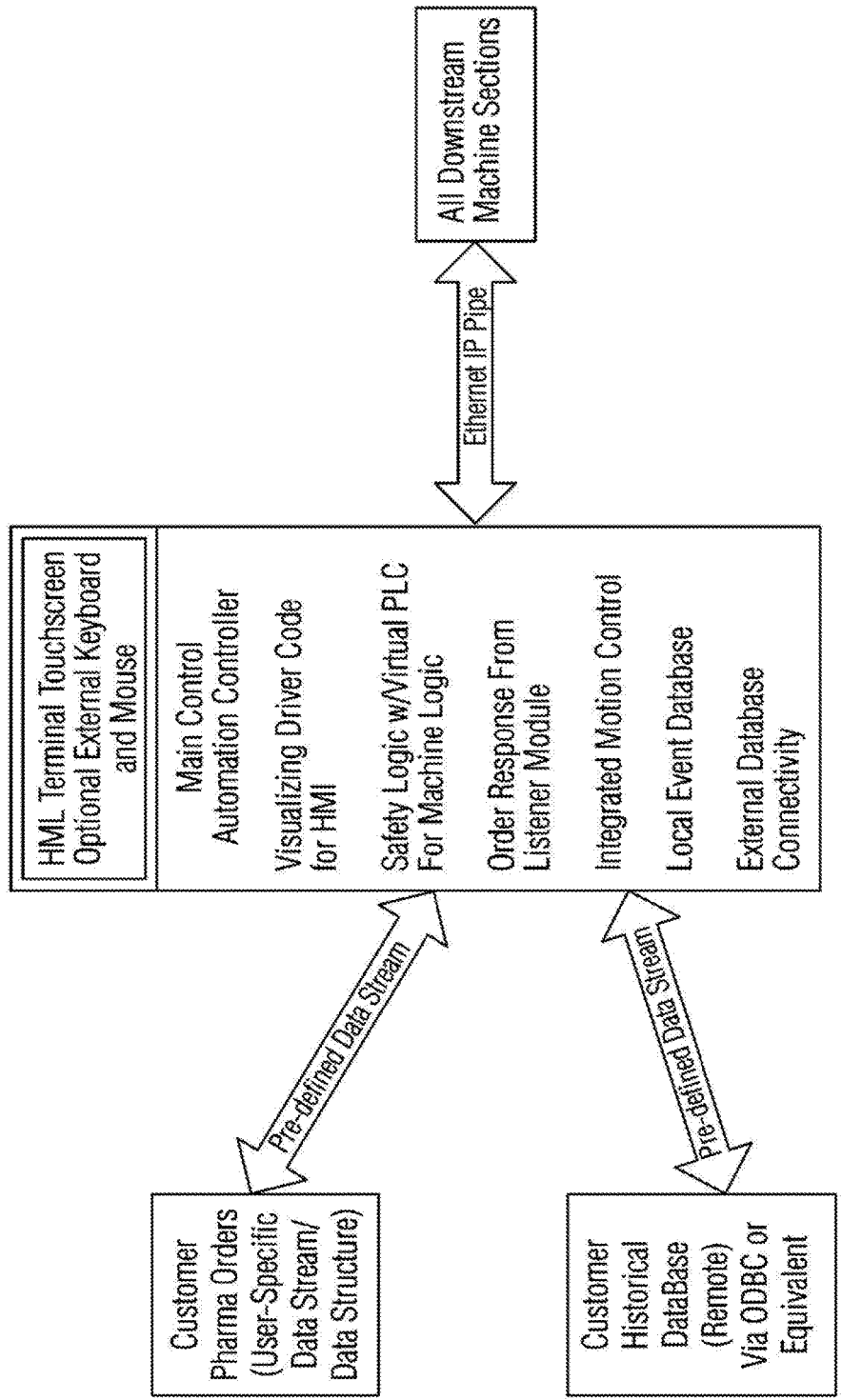

With reference to FIGS. 11 and 12, a control system architecture for the system 100 is disclosed in which a main controller 300 is provided in communication with a series of sub-controllers for one or more station steps via a communications backbone 310, in the depicted case, via Ethernet and local digital inputs and outputs. The main controller 300 is preferably a microprocessor based microcontroller or PC containing a processor core, memory, and programmable input/output peripherals. The controller contains a system safety controller, logic controller, top level motion controller and human-machine interface for interaction with a system operator. The main controller 300 further incorporates a database read/write module for interaction with a local or remote customer (patient) records database and local event database for managing downstream component operation. An order listener/parser module is provided for receiving orders from an external pharmacy/prescription entry and management system maintained by the institution. The parser can be custom formatted to discern and populate order information based on a user specified data stream and structure.

Sub-controllers are provided for all downstream machine sections such as Syringe Storage 320, Inspector/Labeler/Verifier 330, and Medicine Library 350. The sub-controllers are each provided with a local input/output system and local motion controller integrated with the main controller 300 via the communications backbone 310. The main controller orchestrates the integration and operation of the downstream machine elements as described above and controls the overall operational mode of the system 100.

The local O/ESPS Computer may incorporate fill weight/volume adjustment software. Specifically, the vision inspection station 9 (FIG. 2) is networked to the Local O/ESPS Computer and may provide weight or volume feedback to automatically adjust the amount of liquid transferred into the enteral/oral syringe at servo-operated syringe filling station 5. The software determines if a syringe has too much or too little medicine in it. Any out-of-spec syringe will be rejected and the system will automatically queue a replacement utilizing information from the previously-rejected syringe.

Figure 13:
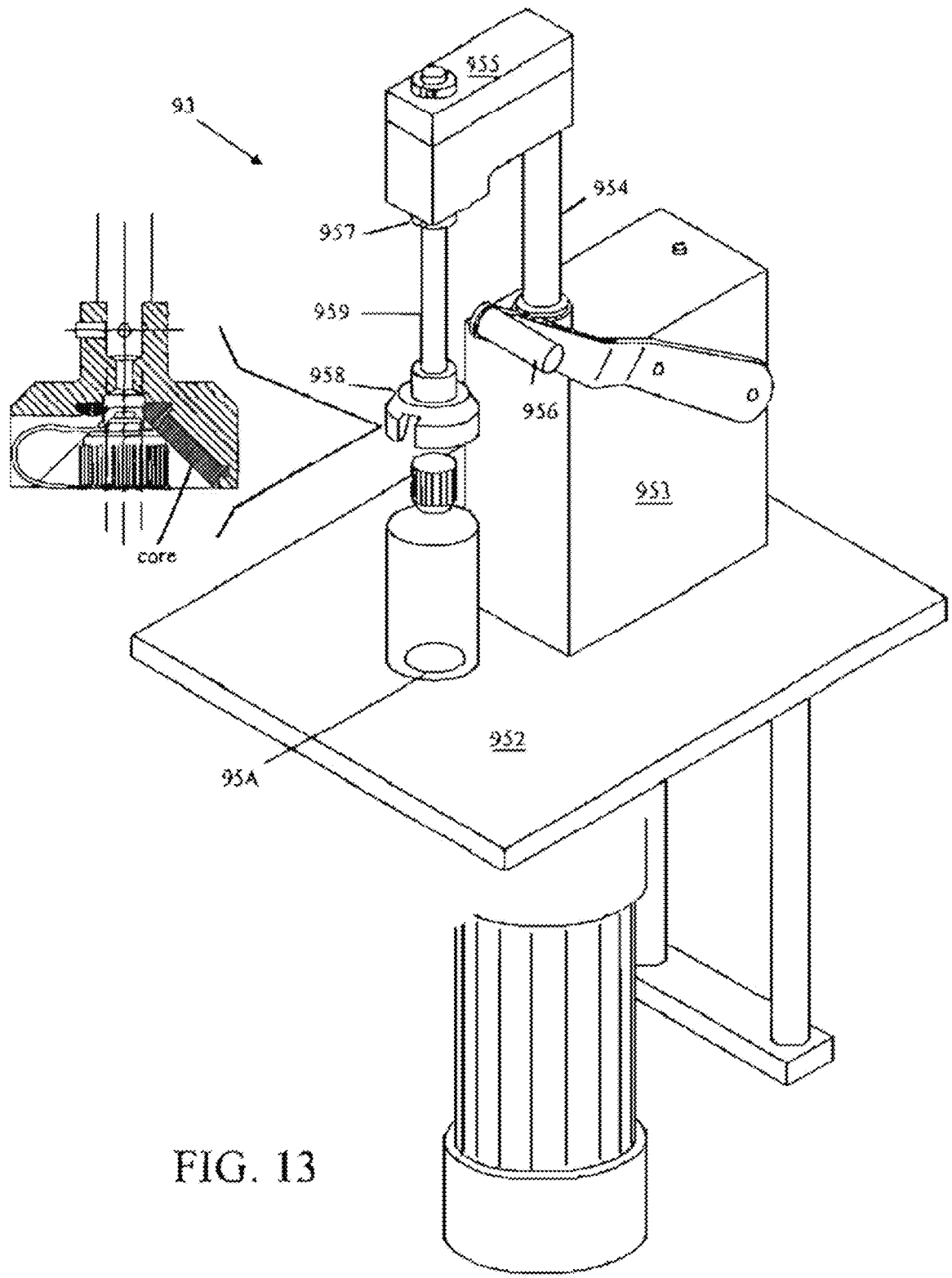
FIG. 13 is a perspective view of an exemplary capping/decapping station 93 resident at the Medication Container Orientation and Log-In Station.

FIG. 13 is a perspective view of an exemplary capping/decapping station 93, which comprises an elevated platform support surface 952 for stabilizing the medicine container. An optional container clamp (not shown) may be mounted on the support surface 952 for centering and constraining the medicine container. The container clamp may comprise a pair of opposing V-shaped clamps. An operator presses a "clamp" button and the opposing V-shaped clamps close around the container bottle. The V-shaped clamps may be mounted on low-friction slides so that any size bottle can be slid toward the center of the chuck. Although the clamps are mounted on low friction slides, they remain stationary to rotation. An articulating spindle assembly extends upward from a base 953 mounted on the support surface 952, the spindle assembly including a vertical piston 954 extendable/retractable from base 953 and a horizontal mast 955 extending from piston 954. The mast 955 contains a motor which drives a vertical spindle 959. A manual lowering arm 956 is geared to the piston 954 for piston extension/retraction from base 953, thereby allowing an operator to raise or lower spindle 959 manually. A pressure sensor 957 is mounted to the spindle 959 (or internal to the mast 955 for sensing the downward pressure. A chuck 958 is mounted at the lower end of the spindle 959. As seen in the inset (at left), the chuck 958 is preferably formed with a hard outer shell (e.g., stainless steel) and a molded plastic core placed inside, the core defined by a conical interior surface with an elastomeric inner lining. An elastomer such as polyurethane or equivalent resin can be poured around the interior of die core to form the elastomeric lining. A lateral slot enters the interior of the chuck 958. This chuck 958 is designed to fit all caps ranging from 18 mm to 38 mm in diameter. Due to its conical interior and elastomeric inner lining, downward pressure onto the container cap causes a non-slip, gripping action. The slot accommodates certain container caps which have a tethered closure feature. The tether is free to protrude and will not cause interference between the chuck 958 and cap. This capping/decapping station 93 enables die medicine caps to be loosened from their containers mechanically without the need for an operator to exert strong hand pressure. The system is capable of loosening caps as well as applying torque to seat them. In operation, the medicine container is placed on the support surface 952, and the operator centers the container either with the optional holding clamp or by hand, and if to cap a pre-labeled container/syringe interface is placed on the container. Upon moving the manual lowering arm 956 forward, the piston 954 extends from base 953, thereby a lowering spindle 959. The chuck 958 descends into contact with the container/syringe interface to tighten it, or into contact with the manufacturer cap if decapping is desired. Once the chuck 958 descends onto the cap and downward force is applied the pressure sensor 957 begins to compress and in doing so, signals the motor to start. This avoids inadvertent rotation of the elastomeric chuck 958 in advance of contacting the cap which may cause abrasion and emit particles of the elastomer in the vicinity of the work area. The scanner 95A may be mounted beneath the platform support 952 to read the medicine container's 2D barcode from beneath. Preferably, the scanner 95A is synchronized via the O/ESPS computer such that the first time it reads a particular barcode the spindle 959/motor turn in the counter-clockwise (cap removal) direction. Conversely, the second time scantier 95A reads that particular barcode Use spindle 959/motor turn in the clockwise (cap tightening) direction. The assembled medicine container and container/syringe interface can be slid out and removed.

Figure 14:
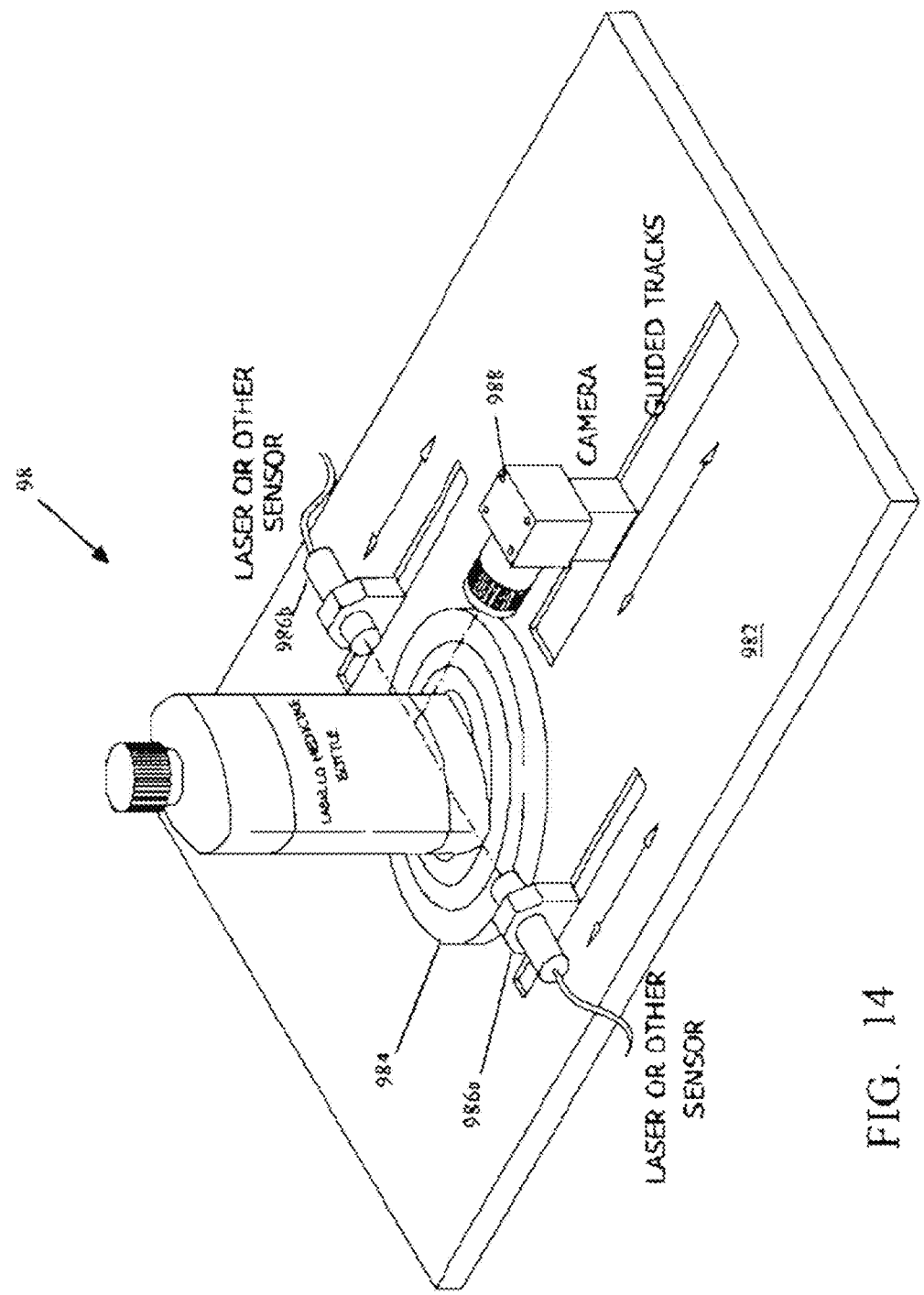
FIG. 14 is a perspective view of the optional photographing station 98 resident at the Medication Container Orientation and Log-In Station.

FIG. 14 is a perspective view of the label photographing station 98 resident at the Medication Container Orientation and Log-In Station. The label photographing station 98 is employed for the purpose of photographing the entire medicine container's label for archival purposes (to retain a record of the medication used to fill a specific prescription). In some cases, die barcode scan from scanner 95A alone will be insufficient to identify details such as medicine concentration, expiration, handling and other precautions relative to the medication. The label photographing station 98 comprises a circular table 984 rotatably seated atop a support surface 982. A camera 988 is oriented directly toward a focal point centrally atop the table 984, and a pair of opposing sensors 986a, 986b are indirectly aimed from the sides toward that same focal point. The camera 988 and sensors 986a, 986b are all mounted on a common undercarriage via struts that pass through tracks in the table 984. This allows the camera 988 and sensors 986a, 986b to translate in unison along the tracks in the table 984. The undercarriage is servo-driven (or otherwise adapted for controlled translation) under control on the O/ESPS Computer, in accordance with feedback from sensors 986a, 986b. The medicine container may be manually placed anywhere atop the table 984, and the O/ESPS Computer will drive the undercarriage until the sensors 986a, 986b align with the surface of the medicine container. The sensors 986a, 986b track the surface of the container and travel with that focal surface, along with the camera 988. This positions the camera 988 at exactly the proper focal distance regardless of container position, and maintains the optimum focal distance from label to camera 988 despite a variety of sizes and shapes of medicine containers.

Process and System Configuration Variations Specific to Contains/Syringe Interface 1. Filling a Syringe Using A standard commercially available "Baxa" cap 214 (see FIG. 5)

The standard commercially available Baxa™ cap 214 comprises a female threaded cap to lit over medication containers and is available in sizes to accommodate most medication containers. Baxa™ cap 214 enables an enteral/oral syringe to enter its center hole and withdraw an amount of liquid from the medication container while the medication container is positioned upside down. For the syringe to be removed from the medication, both syringe and medication container must be up-lighted. Once up-righted, the syringe S can be removed from the up-righted medication bottle with no leakage. If the medication bottle requires shaking at any given time, it can be done manually or in a separate shaker (FIG. 17) by closing the tethered cap and fastening the bottle into the shaker tray. The sequence of operation is as follows:

(1) Remove original cap (FIG. 18A);
    (2) The Baxa™ cap 214 is applied onto the neck of the container (FIG. 18B);
    (3) The syringe S is inserted into the Baxa™ cap 214. (FIG. 18C);
    (4) The medication container and the syringe S combination are rotated up-side-down. (FIG. 18D);
    (5) Both the medication container and the inserted syringe S are then inverted and placed into the yoke 82A (FIG. 18E) of the filling station 5 (see FIG. 7A);
    (6) The Syringe is clamped by the filler finger grippers 78 and a platform 79 (FIG. 18F) lowers to the bottom of the over turned medication bottle and applies downward pressure to the bottle as it is supported by the yoke 82 (see FIG. 7D);
    (7) Now the syringe gripping arms 110, 111 and 112 engage the syringe S plunger, prime and pull the plunger to the exact fill dose (see FIG. 7A);
    (8) Remove medication container and the syringe S combination and extract syringe S.

2. Filling An Oral/Enteral Syringe Using An OEM-Baxa™ Cap With Self Sealing Valve 216 (see FIG. 5).

As described above the standard Baxa™ cap is modified to incorporate a self-sealing valve 216 which enables an enteral/oral syringe S to enter its center hole while the Medication container is positioned upside down without leaking. The Baxa™ Cap with Self Sealing Valve 216 also allows for syringes to be removed after filling without removing the medication container from the filing station 5 (see FIG. 2 III) and repeat the filling of subsequent syringes S when a quantity of syringes are to be filled with the same medication. In the event of a scheduled shaking requirement, after a specified amount of time, the system can shake the medication without removing it from the filling station (see FIG. 16A). Frequency and strokes per minute are pre-programmed into the system. The sequence of operation is as follows:

(1) Remove original cap (FIG. 19A);
(2) Baxa™ Cap with Self Sealing Valve 216 is tightened onto the neck of the container (FIG. 19B);
(3) Medication container is turned upside down (see FIG. 19C). The neck of the container is placed into a slotted yoke 82B or the self-centering spring loaded jaws 82C (FIG. 7B). Since the neck of the container is held on center by the slotted yoke 82B, or the self-centering spring loaded jaws 82C the opening to the Baxa Cap with Self Sealing valve 216 will be properly aligned with tire syringe S and the mechanism for filling the syringe S by pulling the syringe plunger downward, (see FIG. 19C);
(4) The medication container platform 79 is lowered to securely hold the medication container in place onto either the Yoke 82A (sec FIG. 19C);
(5) If tire meditation container needs to be shaken, it is shaken at the programmed speed, duration and frequency (see FIG. 16A);
(6) The syringe S tip is inserted up, into the Baxa Cap with Self Sealing Valve opening 216;
(7) The syringe S is filled by the syringe gripping arms 110, 111 and 112 which engage the syringe S plunger, prime and pull the plunger to the exact fill dose (see FIG. 19D);
(8) The syringe is unclamped by the filler finger grippers 78 and the syringe is removed from the Medication container (FIG. 19D);
(9) If additional syringes S need to be filled with the same medication, the process is repeated;
(10) When all syringes have been filled with the medication, the platform 79 rises and the medication bottle is removed;
(11) This process continues until all syringes for that prescription production run have been filled.

3. Filling A Syringe Using A Flow Restrictor (No Valve) 210 (see FIG. 5)

If a medication container with valveless flow restrictor 210 requires shaking, this must be done either manually or with the optional free standing shaker (FIG. 17). This must be repeated every time shaking is required regardless of whether the same medication is being filled into multiple syringes. The original cap must be placed over the Medication bottle and its press-in insert, during storage, to ensure cleanliness. The sequence of operation is as follows:

(1) Remove medicine bottle cap (FIG. 20A);
(2) The valveless flow restrictor 210 is inserted into the neck of the container (FIG. 20B);
(3) The syringe S is inserted into the valveless flow restrictor 210 (FIG. 20C);
(4) The medication container and live syringe S combination are rotated up-side-down. (FIG. 20D);
(5) The medication container and syringe S combination are placed into the filling station 5 via Yoke 82B or Self-Centering jaws 820 (FIG. 20E);
(6) After filling, the medication container and syringe S combination are removed from the filling station 5;
(7) The medication container and syringe S combination are then up-righted (FIG. 20C), and the filled syringe is then removed from the medication container.

4. Filling A Syringe S Using A Flow Restrictor (With Valve) 212 (see FIG. 5).

The Self Sealing Flow Restrictor Insert 212 is pressed into the neck opening of a medication container and enables an enteral/oral syringe S to enter its center hole and withdraw an amount of liquid from the medication container while the medication container is positioned upside down. In addition, it also enables the syringe to be removed without leaking and the medication container to be shaken at the fill station 5 (FIG. 2 III), while it is positioned upside down and without leaking. The self sealing flow restrictor insert 212 also allows for syringes S to be removed after filling without removing the medication bottle and repeat the filling of subsequent syringes S in cases where a quantity of syringes S are to be filled with the same medication. In the event of a scheduled shaking requirement, after a specified amount of time, the system can shake the medication without removing it from the filling station (see FIG. 16A). Frequency and strokes per minute are pre-programmed into the system. The sequence of operation is as follows:

(1) Remove medicine bottle cap (FIG. 21A);
(2) The self sealing flow restrictor insert 212 is inserted into the neck of the container (FIG. 21B);
(3) The medication container is turned upside down (FIG. 21C);
(4) The neck of the container is placed into the Self Centering Jaws 82C or Yoke 82B (FIG. 21D) Since the neck of the container is held on center by the yoke 82B or Self Centering Jaws 82C, the opening to the self sealing flow restrictor insert 212 will be properly-aligned with the syringe S and the mechanism for filling the syringe;
(5) The medication container platform 79 is lowered to securely hold the medication container in place on the Self Centering Jaws 82C (see FIG. 21D);
(6) If the medication container needs to be shaken, it is shaken at the programmed speed, duration and frequency (see FIG. 16A) while still held in the tilling station 5;
(7) The syringe S is inserted into the self sealing flow restrictor insert 212 opening (FIG. 21E);
(8) The syringe is filled;
(9) The syringe is removed from the medication container;
(10) If additional syringes need to be filled with the same medication, tire process is repeated while the medication bottle remains held within the filler;
(11) When all syringes S have been filled with the medication, the medication container is removed;
(12) This process continues until all syringes for that prescription production run have been filled.

5. Filling An Oral/Enteral Syringe Using A Valved Self-Sealing Two Piece Cap With Common Outer Diameter 220, 221 (see FIG. 5)

As described above, the cap comprises a common outer diameter portion and either an insertable or integrally-formed self-sealing insert which enables an enteral/oral syringe S to enter its center hole while the Medication container is positioned upside down without leaking. The valved self-sealing one or two-piece cap 220, 221 also allow syringes to be removed after filling without removing the medication container from the filing station 5 (see FIG. 2 III) and repeat the filling of subsequent syringes S when a quantity of syringes are to be filled with the same medication. In the event of a scheduled shaking requirement, after a specified amount of time, the system can shake die medication without removing it from the filling station (see FIG. 16A). Frequency and strokes per minute are pre-programmed into the system. The sequence of operation is as follows.

(1) Remove original cap (FIG. 19A);
(2) Valved self-sealing one or two piece cap 220, 221 is tightened onto the neck of the container (FIG. 19B);
(3) Medication container is turned upside down (see FIG. 19C). The neck of the container is placed into a slotted yoke 82B or the self-centering spring loaded jaws 82C (FIG. 7B). Since the neck of the container is held on center by the slotted yoke 82B, or the self-centering spring loaded jaws 82C the opening to the cap 220, 221 will be properly aligned with the syringe S and the mechanism for filling the syringe S by pulling the syringe plunger downward, (see FIG. 19C);
(4) The medication container platform 79 is lowered to securely hold the medication container in place onto either the Yoke 82A (see FIG. 19C);
(5) If the medication container needs to be shaken, it is shaken at the programmed speed, duration and frequency (see FIG. 16A);
(6) The syringe S tip is inserted up, into the cap opening 220, 221;
(7) The syringe S is filled by the syringe gripping arms 110, 111 and 112 which, in concert with arm 128, engage the syringe S plunger, prime and pull the plunger to the exact fill dose (see FIG. 19D);
(8) The syringe is unclamped by the filler finger grippers 78 and the syringe is removed from the Medication container (FIG. 19D);
(9) If additional syringes S need to be filled with the same medication, the process is repeated;
(10) When all syringes have been filled with the medication, the platform 79 rises and the medication bottle is removed;
(11) This process continues until all syringes for that prescription production run have been filled.

In the future, for drug anti-counterfeiting purposes, medication containers may include 2D barcodes applied to them by the manufacturers with unique ID numbers and other data. Consequently, medication containers may be supplied to the pharmacies with a pre-applied 2D barcode providing a unique ID number and other medication-related data. When this is the case, the system does not require that a special barcode label with information on the medication be generated and attached to the base of the medicine container. The medication Container Login & Orientation Station 1 may be bypassed and/or omitted entirely, and the manufacturer's barcode on the container is utilized. A track, trace and control system is similar to the O/ESPS previously described is provided. The objective of the simplified syringe filling and labeling system is to ensure that the proper medication is filled into the syringe and that the syringe is labeled correctly. If an optional weight check or volume check station is utilized, the proper amount of fill can be verified. The system minimizes downtime as well as processing time to take and fill orders, and is easy to clean and capable of maintaining an environment free from cross contamination. The system is open and accessible and allows interaction and oversight by a human operator at multiple points in the operation. Moreover, it is modular and permits a differing and upgradeable level of operator participation (from a syringe filling device only to a semi-automated combination of labeling, filling, inspection, capping, and/or bagging functionality) based on the need of the individual institution.

It should now be apparent that the above-described system is driven by prescription orders in a just-in-time environment, manages all the various prescription containers containing the pharmaceuticals to be dispensed, as well as variously-sized enteral/oral syringes, to automatically converge them and orient, fill, label and cap each syringe and fully verify its work as it proceeds in order to avoid medication errors in the process. The pharmacy automation system for enteral/oral syringes substantially improves the pharmacist and technician productivity- and maintains an environment free from cross contamination.

In all the above-described embodiments, the entire system is modular and permits an upgradeable core based on the need of the individual institution. Optional system components such as the label photographing station 98 resident at the Medication Container Orientation and Log-In Station may be purchased and added to the system subsequent to the original purchase.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims and may be used with a variety of materials and components. This application is therefore intended to cover any variations, uses, or adaptations of the invention using its general principles. Further, this application is intended to cover such departures from the present disclosure as come within known or customary practice in the art to which this invention pertains.

The invention claimed is:

1. A system for positioning a syringe proximate to a flag labeler for labeling of said syringe, comprising:
   a programmable computer including software for controlling said system;
   a syringe positioning fixture comprising,
      a base mounted proximate to said flag labeler,
      a drive mechanism connected to said base,
      a pair of upstanding brackets attached to said base, each bracket of said pair of upstanding brackets including at least one track extending in a first direction;
      a first sled slidably mounted in a track of a bracket of said pair of upstanding brackets,
      a second sled slidably mounted in a track of a bracket of said pair of upstanding brackets,
      a first gripper attached to said first sled, and configured to contact said syringe on one side, and
      a second gripper attached to said second sled, and configured to contact said syringe on another side.

2. The system for positioning a syringe according to claim 1, wherein said first gripper and said second gripper each comprise a gripper arm and a finger protruding from said gripper arm at a right-angle.

3. The system for positioning a syringe according to claim 2, wherein a distance between the finger of said first gripper and the finger of said second gripper is adjustable to accommodate a plurality of syringe sizes.

4. The system for positioning a syringe according to claim 1, wherein a pressure between the finger of said first gripper and the finger of said second gripper is adjustable.

5. The system for positioning a syringe according to claim 1, wherein a syringe held between the finger of said first gripper and the finger of said second gripper may be articulated along two axes of controlled motion.

6. The system for positioning a syringe according to claim 1, wherein said first sled is connected to said second sled for synchronous movement.

7. The system for positioning a syringe according to claim 1, wherein said first sled is connected to said second sled by a linkage for synchronous movement.

8. The system for positioning a syringe according to claim 7, wherein said first sled includes a toothed rack, said second sled includes a toothed rack, and said linkage comprises a pinion gear engaged to the toothed racks thereof.

9. The system for positioning a syringe according to claim 8, wherein said pinion gear constrains movement of the second sled to a distance equal and opposite to movement of the first sled.

10. The system for positioning a syringe according to claim 9, wherein said linkage is configured to self-center said syringe held between the first gripper and the finger of said second gripper regardless of a shape of said syringes.

11. The system for positioning a syringe according to claim 1, further comprising at least one sensor configured to measure a diameter of said syringe.

12. The system for positioning a syringe according to claim 11, wherein said at least one sensor comprises an encoder.

13. The system for positioning a syringe according to claim 11, wherein said at least one sensor comprises a linear variable differential transformer (LVDT).

14. The system for positioning a syringe according to claim 1, wherein each bracket of said pair of upstanding brackets includes a first track oriented along said first direction and a second track parallel to said first track, said first sled being slidably mounted between said first track and said second track of said pair of upstanding brackets.

15. The system for positioning a syringe according to claim 14, wherein said second sled is slidably mounted between said first track and said second track of said pair of upstanding brackets.

16. The system for positioning a syringe according to claim 1, further comprising at least horizontal translation mechanism for X-Y positioning of a syringe.

17. The system for positioning a syringe according to claim 1, further comprising at least one scanner for analyzing a label prior to placement on the syringe.

18. The system for positioning a syringe according to claim 7, further comprising at least one scanner for analyzing a label after placement on the syringe.

19. The system for positioning a syringe according to claim 7, further comprising at least one scanner for analyzing a label before placement on the syringe.

20. The system for positioning a syringe according to claim 7, further comprising a first scanner for analyzing a label after placement on the syringe, and a second scanner for analyzing a label before placement on the syringe.

21. The system for positioning a syringe according to claim 1, further comprising a syringe filling station.

22. The system for positioning a syringe according to claim 21, wherein both said syringe filling station and said flag labeler are in communication with a common computer system.

23. The system for positioning a syringe according to claim 1, wherein said syringe positioning fixture further comprises an open-faced housing mounted on a subplate, and said subplate is removably mountable to a baseplate.

24. A syringe positioning fixture for positioning a syringe proximate to a flag labeler for labeling of said syringe, comprising:
 a base mounted proximate to said flag labeler, said base including a pair of upstanding support members including a first support member having a first upwardly-extending track, and a second support member having a second upwardly extending track parallel to said first track;
 a first gripper mounted in said first track and configured to contact said syringe on one side;
 a second gripper mounted in said second track and configured to contact said syringe on an opposing side, and
 a drive mechanism configured to drive said first gripper and said second gripper.

25. The syringe positioning fixture for positioning a syringe proximate to a flag labeler according to claim 24, wherein said first gripper and said second gripper each comprise a gripper arm and a finger protruding from said gripper arm at an angle.

26. The syringe positioning fixture for positioning a syringe proximate to a flag labeler according to claim 24, wherein said first gripper is gear-coupled to said second gripper for synchronous movement.

27. The system for positioning a syringe according to claim 1, further comprising at least horizontal translation mechanism for horizontal positioning of said syringe relative to said flag labeler.

* * * * *